(12) United States Patent
Bandi et al.

(10) Patent No.: US 10,669,305 B2
(45) Date of Patent: Jun. 2, 2020

(54) C-3 NOVEL TRITERPENONE WITH C-28 UREA DERIVATIVES AS HIV INHIBITORS

(71) Applicant: Hetero Labs Limited, Hyderabad (IN)

(72) Inventors: Parthasaradhi Reddy Bandi, Hyderabad (IN); Rathnakar Reddy Kura, Hyderabad (IN); David Krupadanam Gazula Levi, Hyderabad (IN); Panduranga Reddy Adulla, Hyderabad (IN); Bhaskar Reddy Kasireddy, Hyderabad (IN); Carl Thomas Wild, Gaithersburg, MD (US); David Eugene Martin, Shawnee, OK (US); Theodore John Nitz, Boyds, MD (US)

(73) Assignee: HETERO LABS LIMITED, Hyderabad (IN)

( * ) Notice: Subject to any disclaimer, the term of this patent is extended or adjusted under 35 U.S.C. 154(b) by 0 days.

(21) Appl. No.: 15/767,756

(22) PCT Filed: Oct. 12, 2016

(86) PCT No.: PCT/IB2016/056099
§ 371 (c)(1),
(2) Date: Apr. 12, 2018

(87) PCT Pub. No.: WO2017/064628
PCT Pub. Date: Apr. 20, 2017

(65) Prior Publication Data
US 2018/0305398 A1 Oct. 25, 2018

(30) Foreign Application Priority Data

Oct. 13, 2015 (IN) .......................... 5467/CHE/2015

(51) Int. Cl.
| | |
|---|---|
| *C07J 53/00* | (2006.01) |
| *A61K 31/00* | (2006.01) |
| *A61K 31/58* | (2006.01) |
| *C07J 63/00* | (2006.01) |
| *A61P 31/18* | (2006.01) |

(52) U.S. Cl.
CPC ............ *C07J 53/002* (2013.01); *A61K 31/00* (2013.01); *A61K 31/58* (2013.01); *A61P 31/18* (2018.01); *C07J 63/008* (2013.01)

(58) Field of Classification Search
CPC ....... C07J 53/002; C07J 63/008; A61K 31/58; A61K 31/00
See application file for complete search history.

(56) References Cited

U.S. PATENT DOCUMENTS

| 6,221,400 B1 * | 4/2001 | Liversidge ............. A61K 9/146 424/489 |
| 2006/0205697 A1 | 9/2006 | Robinson et al. |

FOREIGN PATENT DOCUMENTS

WO WO 2009/082819 * 7/2009

OTHER PUBLICATIONS

Interanational Search Report for International Applicaton No. PCT/IB2016/056099, International Filing Date Oct. 12, 2016, dated Jan. 31, 2017, 4 pages.
Written Opinion for International Application No. PCT/IB2016/056099, International Filing Date Oct. 12, 2016, dated Jan. 31, 2017, 7 pages.

* cited by examiner

Primary Examiner — Sahar Javanmard
(74) Attorney, Agent, or Firm — Cantor Colburn LLP

(57) ABSTRACT

The present invention relates to C-3 novel triterpenone with C-28 urea derivatives of formula (I); or pharmaceutically acceptable salts, pharmaceutically acceptable solvates, pharmaceutically acceptable hydrates, tautomers, stereoisomers, prodrugs, compositions or combination thereof, wherein $R_1$, $R_2$, $R_3$, W, J and X are as defined herein. The present invention also relates to pharmaceutical compositions comprising compounds of formula (I) useful for the treatment of viral diseases and particularly HIV mediated diseases.

Formula (I)

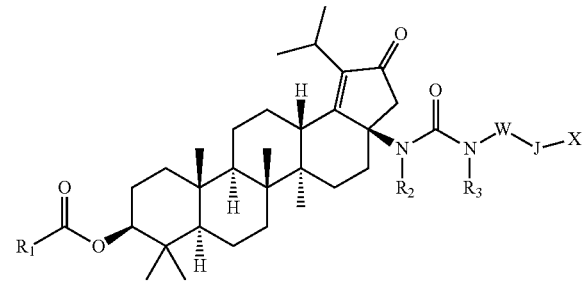

11 Claims, No Drawings

C-3 NOVEL TRITERPENONE WITH C-28 UREA DERIVATIVES AS HIV INHIBITORS

This application claims the benefit of Indian provisional application no 5467-CHE-2015 filed on 13 Oct. 2015 which is hereby incorporated by reference in its entirety.

FIELD OF THE INVENTION

The present invention relates to C-3 novel triterpenone with C-28 urea derivatives and related compounds, compositions useful for therapeutic treatment of viral diseases and particularly HIV mediated diseases.

BACKGROUND OF THE INVENTION

The Human Immunodeficiency Virus (HIV) has now been established as the causative agent of the Acquired Immunodeficiency Syndrome (AIDS) for over 20 years (Science 1983, 220, 868-871; N. Eng. J. Med. 1984, 311, 1292-1297). AIDS is characterized by the destruction of the immune system, particularly of CD4+T-cells. HIV is a retrovirus, and the HIV life cycle encompasses several crucial steps, starting from the attachment of the virus to the host cell membrane and finishing with the release of progeny virons from the cell.

The natural compound betulinic acid, isolated from Syzygium clavifolium and several other plant species was found to possess anti-HIV activity. Chemical modifications were undertaken by several research groups in an attempt to identify potent anti-HIV agents by making semi-synthetic analogs of betulinic acid, leading to the discovery of Bevirimat as a compound with a novel mechanism of action (J. Nat. Prod. 1994, 57(2): 243-7; J. Med. Chem. 1996, 39(5), 1016). Further studies shown that Bevirimat acts by disrupting Gag processing (Proc. Natl. Acad. Sci. USA 2003, 100 (23):13555-60; Antimicrob. Agents. Chemother. 2001, 45(4), 1225-30; J. Virol. 2004, 78(2): 922-9; J. Biol. Chem. 2005, 280(51): 42149-55; J. Virol. 2006, 80(12): 5716-22) and to be a first-in-class maturation inhibitor with a potent activity against HIV-1. Bevirimat went up to phase 2 clinical trials, in clinic despite optimal plasma concentrations, not all patients given bevirimat have a robust viral load reduction. It was reported that non-respondant patients had more frequent base line Gag polymorphisms near the capsid SP-1 cleavage site than responders. (HIV gag polymorphism determines treatment response to bevirimat. XVII international HIV drug resistance work shop Jun. 10-14, 2008, Sitges, Spain).

Encouraged by these developments, medicinal chemists started exploring betulinic acid derivatives and related compounds intensively for their therapeutic activities. For example, WO 2014/105926 disclosed novel betulinic acid proline derivatives as HIV inhibitors; WO 2013/160810 disclosed novel betulinic acid derivatives as HIV inhibitors; WO 2011/007230 describes preparation of lupeol-type triterpene derivatives as antiviral agents; WO 2014/093941 describers pharmaceutical compositions of betulin derivatives; WO 2009/082819 describes preparation of 17-amino lupane derivatives as anti-HIV agents; WO 2013/020245 describes carbonyl derivatives of betulin; WO 2009/082818 describes preparation of C21-keto lupane derivatives for the treatment of HIV Infections; WO 2011/100308 describes preparation of betulin derivatives for treatment of HIV-1; WO 2013/090664 describes preparation of betulin derivatives for the treatment of HIV; WO 2013/117137 describes lupane triterpenoids derivatives and pharmaceutical use thereof; WO 2013/091144 describes preparation of propenoate derivatives of betulin useful for the treatment of HIV.

Some additional references disclose betulinic acid related compounds. For example, WO 2013/090683 describes preparation of betulin propenoate derivatives for the treatment of HIV; WO 2013/020246 describes preparation of methylene derivatives of betulin useful for the treatment of HIV; WO 2010/132334 describes C3,28-Disubstituted betulinic acid derivatives as Anti-HIV agents; US 2011/0152229 describes betulinic acid derivatives as anti-HIV agents; WO 2008/057420 describes extended triterpene derivatives as antiretroviral agents; WO 2013/123019 describes C-3 cycloalkenyl triterpenoids with HIV maturation inhibitory activity; WO 2007/141392 describes compositions comprising betulonic acid; WO 2007/141391 describes betulin derived compounds useful as antiprotozoal agents; WO 2007/141390 describes preparation of betulin derived compounds as antiviral agents; WO 2007/141389 describes preparation of betulin derived compounds as antibacterial agents.

Given the fact of the world wide epidemic level of AIDS, there is a strong continued need for new effective drugs for treatment of HIV infected patients, disease conditions and/or disorders mediated by HIV by discovering new compounds with novel structures and/or mechanism of action(s).

SUMMARY OF THE INVENTION

The present invention relates to the compounds of the formula (I):

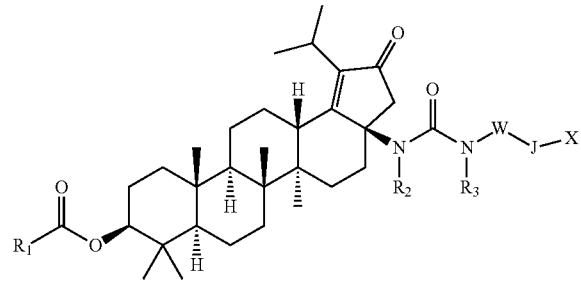

Formula (I)

wherein, $R_1$ is

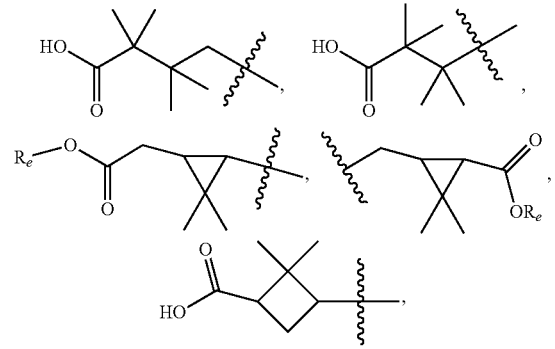

-continued

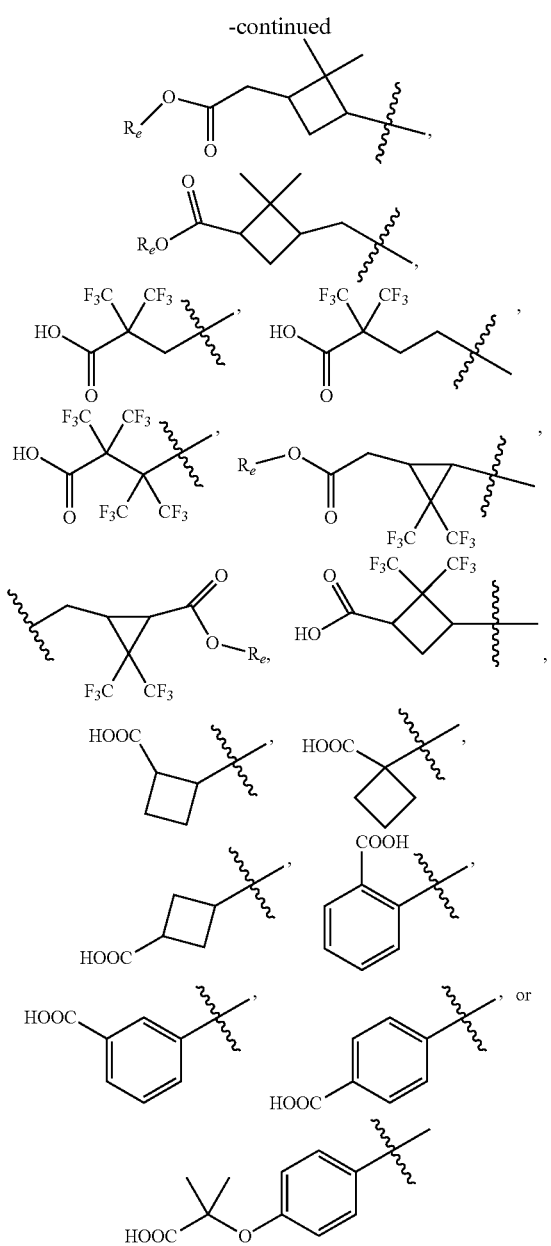

(wherein R_e is hydrogen, substituted or unsubstituted alkyl, or substituted or unsubstituted cycloalkyl);

$R_2$ is hydrogen or substituted or unsubstituted alkyl;

$R_3$ is hydrogen, substituted or unsubstituted alkyl, substituted or unsubstituted amino alkyl, substituted or unsubstituted alkoxylalkoxy, substituted or unsubstituted alkoxylalkyl, substituted or unsubstituted arylalkyl, substituted or unsubstituted cycloalkylalkyl, substituted or unsubstituted heterocyclylalkyl or substituted or unsubstituted heteroarylalkyl; wherein the substituents are alkyl, halo or hydroxyl;

W is $(CR_aR_b)_n$;

$R_a$ and $R_b$ are independently hydrogen or substituted or unsubstituted alkyl, or $R_a$ and $R_b$ are taken together with the carbon to which they are attached to form 3-6 membered cycloalkyl;

W and $R_3$ are taken together with the nitrogen to which they are attached to form substituted or unsubstituted 4-10 membered heterocyclyl; wherein the substituents are alkyl, halo or hydroxy;

J is absent, $(CR_cR_d)_{1-2}$ or $NR_g$;

$R_c$ and $R_d$ are independently hydrogen or $R_c$ and $R_d$ are taken together with the carbon to which they are attached to form 3-6 membered cycloalkyl;

$R_g$ is hydrogen or substituted or unsubstituted alkyl;

$R_3$ and $R_g$ are taken together with the nitrogen atoms to which they are attached to form substituted or unsubstituted 4-10 membered heterocyclyl; wherein the substituents are alkyl, halo or hydroxy;

X is absent, substituted or unsubstituted alkyl, substituted or unsubstituted cycloalkyl, substituted or unsubstituted aryl, substituted or unsubstituted heterocyclyl or substituted or unsubstituted heteroaryl; wherein the substituent is one or more $R_f$;

$R_f$ is independently halogen, hydroxy, alkyl, alkoxy, aryl, —O-heterocyclyl, —O— aminoalkyl or aminoalkyl; and 'n' is 1 to 4;

or pharmaceutically acceptable salts, pharmaceutically acceptable solvates, pharmaceutically acceptable hydrates, tautomers, stereoisomers, ester prodrugs, or combination thereof.

Pharmaceutically acceptable salts of the compounds of the formula (I) are also contemplated. Likewise, pharmaceutically acceptable solvates, including hydrates, of the compounds of the formula (I) are contemplated.

It should be understood that the formula (I) structurally encompasses all stereoisomers, including enantiomers, diastereomers, racemates, and combinations thereof which may be contemplated from the chemical structure of the genus described herein.

It should be understood that the formula (I) structurally encompasses all tautomers.

Also contemplated are prodrugs of the compounds of the formula (I), including ester prodrugs.

According to one embodiment, there is provided a compound of formula (I), wherein $R_1$ is

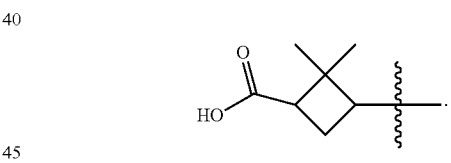

According to yet another embodiment, there is provided a compound of formula (I), wherein $R_3$ is hydrogen.

According to yet another embodiment, there is provided a compound of formula (I), wherein $R_3$ is aminoalkyl; In particular aminoalkyl is N-methylethanamine or N,N-dimethylethanamine.

According to yet another embodiment, there is provided a compound of formula (I), wherein $R_3$ is heterocyclylalkyl; In particular heterocyclylalkyl is 1-ethylpyrrolidine or 1-ethylpiperidine.

According to yet another embodiment, there is provided a compound of formula (I), wherein "W" is $(CR_aR_b)_{1-4}$.

According to preceeding embodiment $R_a$ and $R_b$ are hydrogen, alkyl (preferably methyl) or $R_a$ and $R_b$ are taken together with the carbon to which they are attached to form 3-6 membered cycloalkyl (preferably cyclopropyl).

According to yet another embodiment, there is provided a compound of formula (I), wherein "J" is absent or —$NR_g$; wherein $R_g$ is hydrogen or alkyl.

According to yet another embodiment $R_3$ and $R_g$ are taken together with the nitrogen atoms to which they are attached to form substituted or unsubstituted 4-10 membered heterocyclyl; in particular heterocyclyl is piperazine.

According to yet another embodiment, there is provided a compound of formula (I), wherein "X" is substituted or unsubstituted aryl (preferably phenyl).

According to yet another embodiment, there is provided a compound of formula (I), wherein "X" is substituted or unsubstituted heteroaryl (preferably imidazole or triazole).

According to yet another embodiment, there is provided a compound of formula (I), wherein "X" is substituted or unsubstituted heterocyclyl (preferably pyrrolidine).

According to yet another embodiment, there is provided a compound of formula (I), wherein $R_f$ is alkyl (methyl), halo (chloro), amino alkyl (dimethylethanamine).

Accordingly, another aspect of the present invention provides compounds of formula (IA):

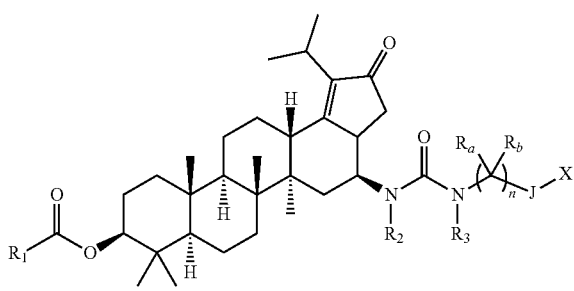

Formula (IA)

wherein, $R_1$, $R_2$, $R_3$, $R_a$, $R_b$, J, X and n are same as defined above or pharmaceutically acceptable salts, pharmaceutically acceptable solvates, pharmaceutically acceptable hydrates, tautomers, stereoisomers, prodrugs, or combination thereof.

Accordingly, another aspect of the present invention provides compounds of formula (IB):

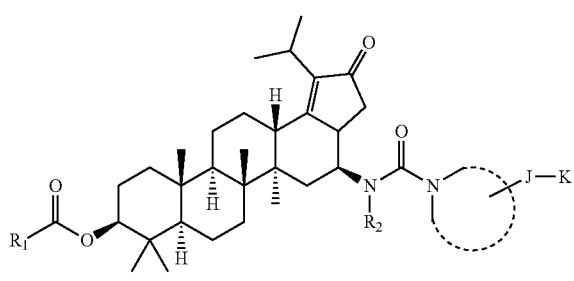

Formula (IB)

wherein, $R_1$, $R_2$, J and X are same as defined above and

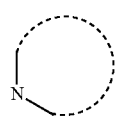

is substituted or unsubstituted 4-7 membered heterocyclyl or pharmaceutically acceptable salts, pharmaceutically acceptable solvates, pharmaceutically acceptable hydrates, tautomers, stereoisomers, prodrugs, or combination thereof.

In a further embodiment, there is provided a method for treating mammals infected with a virus, especially wherein said virus is HIV, comprising administering to said mammal an antiviral effective amount of a compound which is selected from the group of compounds of formula (I), and one or more pharmaceutically acceptable carriers, excipients or diluents. Optionally, the compound of formula (I) can be administered in combination with an antiviral effective amount of another AIDS treatment agent selected from the group consisting of: (a) an AIDS antiviral agent or (b) an anti-infective agent.

Another embodiment of the present invention is a pharmaceutical composition comprising one or more compounds of formula (I), and one or more pharmaceutically acceptable carriers, excipients, and/or diluents; and optionally in combination with another AIDS treatment agent selected from the group consisting of: AIDS antiviral agent or anti-infective agent.

In another embodiment of the present invention there is provided one or more methods for preparation of the compounds of formula (I).

In one further embodiment, the present invention also encompasses the method(s) of preparation of intermediates used in the preparation of compound of formula (I).

Below are the representative compounds, which are illustrative in nature only and are not intended to limit to the scope of the invention (Nomenclature has been generated from ChemBioDraw Ultra 13.0 version):

(1R,3S)-3-(((((3aR,5aR,5bR,7aR,9S,11aR,11bR,13aS)-3a-(3-(4-chlorobenzyl)-3-(2-(di methylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride (Example 1), (1R,3S)-3-(((((3aR,5aR,5bR,7aR,9S,11aR,11bR,13aS)-3a-((S)-2-(1-(2-(dimethyl amino)ethyl)-5-phenyl-1H-imidazol-2-yl)pyrrolidine-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 2), (1R,3S)-3-(((((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl) oxy) carbonyl)-2,2-dimethylcyclobutane-1-carboxylic acid (Example 3), (1R,3S)-3-(((((3aR,5aR,5bR,7aR,9S,11aR,11bR,13aS)-3a-(3-(1-(4-chlorophenyl) cyclopropyl) ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Example 4), (1R,3S)-3-(((((3aR,5aR,5bR,7aR,9S,11aR,11bR,13aS)-3a-(3-(2-(4-chlorophenyl) propan-2-yl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 5), (1R,3S)-3-(((((3aR,5aR,5bR,7aR,9S,11aR,11bR,13aS)-3a-(3-((1-(4-chlorophenyl) cyclopropyl)methyl)-3-(2-(dimethylamino)ethyl)ureido)-1-isopropyl-5a,5b,8,8,11a-penta methyl-2-oxo-3,3a,4,5,5a,5b,6,7,7a,8,9,10,11,11a, 11b,12,13,13a-octadecahydro-2H-cyclo penta[a]chrysen-9-yl)oxy)carbonyl)-2,2-dimethylcyclobutane-1-carboxylic acid (Example 6), (1R,3S)-3-((((3aR,5aR,5bR,7aR,9S,11aR,11bR,13aS)-3a-(3-(4-chlorobenzyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 7), (1R,3S)-3-((((3aR,5aR,5bR,7aR,9S,11aR,11bR,13aS)-1-isopropyl-3a-((1R,3S,5S)-3-(3-isopropyl-5-methyl-4H-1,2,4-triazol-4-yl)-8-azabicyclo[3.2.1]octane-8-carboxamido)-5a,5b,8,8,11a-pentamethyl-2-oxo-3,3a,4,5,5a,5b,6,7,7a,8,9,10,11,11a,11b,12,13,13a-octadeca hydro-2H-cyclopenta[a]chrysen-9-yl)oxy)carbonyl)-2,2-dimethylcyclobutane-1-carboxylic acid (Example 8), (1R,3S)-3-((((3aR,5aR,5bR,7aR,9S,11aR,11bR,13aS)-3a-(3-(4-chlorobenzyl)-3-(2-(pyrrolidin-1-yl)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Example 9), (1R,3S)-3-((((3aR,5aR,5bR,7aR,9S,11aR,11bR,13aS)-1-isopropyl-5a,5b,8,8,11a-pentamethyl-2-oxo-3a-(3-(2-(5-phenyl-1H-imidazol-2-yl)propan-2-yl)ureido)-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Example 10), (1R,3S)-3-((((3aR,5aR,5bR,7aR,9S,11aR,11bR,13aS)-3a-(3-(4-chlorobenzyl)-3-(2-(piperidin-1-yl)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid hydrochloride (Example 11), (1R,3S)-3-((((3aR,5aR,5bR,7aR,9S,11aR,11bR,13aS)-1-isopropyl-3a-(4-(2-(3-iso propyl-5-methyl-4H-1,2,4-triazol-4-yl)ethyl)piperazine-1-carboxamido)-5a,5b,8,8,11a-penta methyl-2-oxo-3,3a,4,5,5a,5b,6,7,7a,8,9,10,11,11a,11b,12,13,13a-octadecahydro-2H-cyclo penta[a] chrysen-9-yl)oxy)carbonyl)-2,2-dimethylcyclobutane-1-carboxylic acid (Example 12), and (1R,3S)-3-((((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Example 13), or pharmaceutically acceptable salts, pharmaceutically acceptable solvates, pharmaceutically acceptable hydrates, tautomers, stereoisomers, prodrugs are also contemplated.

In further yet another embodiment, the compounds of formula (I) structurally encompasses all stereoisomers, enantiomers and diastereomers, and pharmaceutically acceptable salts that may be contemplated from the chemical structure of the general formula (I) described herein.

The absolute configuration at an asymmetric atom is specified by either R or S. Resolved compounds whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 5%, in particularly less than 2% or 1% of the other isomers. Thus when a compound of formula (I) is for instance specified as (R), this means that the compound is substantially free of (S) isomer; when the compound of formula (I) is for instance specified as E, this means that the compound is free of the Z isomer; when the compound of formula (I) is for instance specified as cis isomer, this means that the compound is free of the trans isomer.

In further yet another embodiment, the prodrugs of present invention are the compounds of formula (I) and its pharmaceutically acceptable salts, stereosiomers, solvates thereof containing an hydroxyl group; wherein hydrogen atom of the hydroxyl group are replaced with (C1-C6)alkanoyloxymethyl, 1-((C1-C6)alkanoyloxy)ethyl, 1-methyl-1-((C1-C6)alkanoyloxy)ethyl, (C1-C6)alkoxycarbonyloxymethyl, N—(C1-C6)alkoxycarbonyl aminomethyl, succinoyl, (C1-C6)alkanoyl, α-amino(C1-C4)alkyl, α-amino(C1-C4)alkylene-aryl, arylacyl and α-aminoacyl, where each α-aminoacyl group is independently selected from the naturally occurring L-amino acids, or glycosyl (the radical resulting from the removal of a hydroxyl group of the hemiacetal form of a carbohydrate).

In further yet another embodiment, the prodrugs of present invention are the compounds of formula (I) and its pharmaceutically acceptable salts, stereosiomers, solvates thereof containing an amine group; wherein one or more hydrogen atoms of the amine group is replaced with (C1-C6)alkylcarbonyl, (C1-C6)alkoxycarbonyl, aminocarbonyl, (C3-C6)cycloalkylcarbonyl, benzylcarbonyl and the like.

The present invention also provides a pharmaceutical composition that includes at least one compound as described herein and at least one pharmaceutically acceptable excipient (such as a pharmaceutically acceptable carrier or diluent). Specifically, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in a therapeutically effective amount to cure that infection, specifically in the form of a pharmaceutical composition.

In another aspect, the present invention relates to combinations comprising a compound of the formula (I) and a second therapeutic agent that is an anti-HIV agent, an anti-HCV agent or anti-TB agents.

In another aspect, the present invention relates to combinations comprising a compound of the formula (I) and one or more second anti-HIV agents selected from the group consisting of Protease inhibitors, Integrase inhibitors, Nucleoside Reverse Transcriptase inhibitors, Non-Nucleoside Reverse Transcriptase Inhibitors, Fusion/Entry inhibitors, Pharmacokinetic enhancers, and combinations thereof.

In another aspect, the present invention relates to pharmaceutical compositions comprising the compound of formula (I) and one or more second anti-HIV agents and their pharmaceutically acceptable salts and stereoisomers thereof.

The present invention relates to methods of treatment of HIV infection, AIDS, and AIDS-related conditions by administering to a subject a compound of formula (I) and one or more second therapeutic agents selected from the group consisting of Protease inhibitors, Integrase inhibitors, Nucleoside Reverse Transcriptase inhibitors, Non-Nucleoside Reverse Transcriptase Inhibitors, Fusion/Entry inhibitors, Pharmacokinetic enhancers, and combinations thereof.

In another aspect, the present invention relates to combinations comprising a compound of the formula (I) and one or more second anti-HIV agents wherein the second anti-HIV agent is Abacavir, Didanosine, Emtricitabine, Lamivudine, Stavudine, Tenofovir disoproxil Fumarate, Tenofovir Alafenamide Fumarate, Zidovudine, Efavirenz, Etravirine, Nevirapine, Rilpivirine, Atazanavir, Darunavir, Fosamprenavir, Indinavir, Nelfinavir, Ritonavir, Cobicistat, Saquinavir, Tipranavir, Enfuvirtide, Maraviroc, Fosetemsavir, Dolutegravir, Elvitegravir, Raltegravir, Bictegravir, Cobetagravir or a combination thereof.

Also provided herein are processes for preparing compounds described herein.

The invention provides a method for preventing; ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as persistent generalized lymphadenopathy, fever and weight loss, or a retroviral infection genetically related to AIDS.

Anti HIV inhibitory potential of the compounds of present invention may be demonstrated by any one or more methodologies known in the art, such as by using the assays described in Mossman T, December 1983, *Journal of immunological methods*, 65 (1-2), 55-63 and *SPC Cole, cancer chemotherapy and Pharmacology*, 1986, 17, 259-263.

DETAILED DESCRIPTION OF THE INVENTION

The present invention provides substituted C-3 novel triterpenone with C-28 urea derivatives and related compounds, which may be used as antiviral particularly as anti-HIV compounds and processes for the synthesis of these compounds. Pharmaceutically acceptable salts, pharmaceutically acceptable solvates, enantiomers, diastereomers of the derivatives, together with pharmaceutically acceptable carriers, excipients or diluents, which can be used for the treatment of diseases, condition and/or disorders mediated by viral infections, are also provided.

The following definitions apply to the terms as used herein:

The terms "halogen" or "halo" includes fluorine, chlorine, bromine, or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), isobutyl, n-butyl, n-pentyl, and 1,1-dimethylethyl (t-butyl).

The term "amino" refers to —$NH_2$.

The term "alkoxy" refers to a straight or branched hydrocarbon chain with oxygen radical consisting carbon and hydrogen atoms, containing saturation or unsaturation, having from one to eight carbon atoms, and which is attached through oxygen atom to the rest of the molecule by a single bond, e.g., methyloxy, ethyloxy, n-propyloxy, 1-methylethyloxy (isopropyloxy), n-butyloxy, n-pentyloxy, and 1,1-dimethylethyloxy (t-butyloxy).

The term "alkoxylalkoxy" refers to a straight or branched hydrocarbon chain with oxygen radical consisting carbon atom, hydrogen atom and alkoxy groups, containing saturation or unsaturation, having from one to eight carbon atoms, and which is attached through oxygen atom to the rest of the molecule by a single bond, e.g., 2-(methyloxy) ethyloxy, 2-(ethyloxy)ethyloxy, 2-(n-propyloxy)ethyloxy, and 3-(isopropyloxy)butyloxy.

The term "alkoxylalkyl" refers to an alkyl group, as defined above wherein one or more of the alkyl group's hydrogen atom has been replaced with an alkoxy group as defined above.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronapththyl, adamantyl and norbornyl groups, bridged cyclic groups and spirobicyclic groups, e.g., spiro (4,4) non-2-yl.

The term "cycloalkylalkyl" refers to an alkyl group, as defined above wherein one or more of the alkyl group's hydrogen atom has been replaced with an cycloalklyl group as defined above.

The term "amino acid(s)" refers to a straight or branched hydrocarbon chain containing an amine group, a carboxylic acid group, and a side-chain that is specific to each amino acid and which is attached through the nitrogen atom of the amine group to the rest of the molecule by a single bond, e.g., alanine, valine, isoleucine, leucine, phenylalanine, or tyrosine.

The term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluoro chloromethyl, dichloro fluoromethyl, difluoroethyl, difluoropropyl and the like.

The term "aminoalkyl" refers to an amino group as defined above in which one, two or three hydrogen atoms are substituted with alkyl group. Examples of aminoalkyl include but not limited to —$CH_2NH_2$, $(CH_3)NH$, —$(CH_2)_3NH_2$ or $(CH_3)_2N(CH_2)_2$.

The term "aryl" refers to an aromatic radical having from 6 to 14 carbon atoms such as phenyl, naphthyl, tetrahydronapthyl, indanyl, and biphenyl.

The term 'hydroxy' refers to —OH group.

The terms "heterocyclyl" and "heterocyclic ring" refer to a saturated 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; Examples of such heterocyclic ring radicals include, but are not limited to, tetrahydroisouinolyl, piperidinyl, piperazinyl, azapanyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, morpholinyl, octahydroindolyl, octahydroisoindolyl, decahydroisoquinolyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl. The heterocyclic ring radical may be attached to the main structure at any heteroatom or carbon atom that results in the creation of a stable structure.

The term "heteroaryl" refers to an aromatic heterocyclic ring radical. The heteroaryl ring radical may be attached to the main structure at any heteroatom or carbon atom that results in the creation of a stable structure. Examples of such heteroaryl ring include, but are not limited to imidazolyl, pyrazolyl, pyrrolyl, 1H-pyrrolo[2,3-b]pyridinyl, tetrazoyl, pyrimidinyl, pyridazinyl, oxazolyl, oxazolinyl, oxazolidinyl, triazolyl, isoxazolyl, isoxasolidinyl, thiazolyl, thiazolinyl, thiazolidinyl, isothiazolyl, quinuclidinyl, isothiazolidinyl, indolyl, isoindolyl, indolinyl, isoindolinyl, quinolyl, isoquinolyl, benzimidazolyl, thiadiazolyl, benzothiazolyl, benzooxazolyl, furyl, The term "arylalkyl" refers to an alkyl group, as defined above, wherein one or more of the alkyl group's hydrogen atom has been replaced with an aryl group as defined above. Examples of arylalkyl group include, but are not limited to benzyl, benzhydryl, 1-phenylethyl, 2-phenylethyl, 3-phenylpropyl, 2-phenylpropyl, 1-naphthylmethyl, 2-naphthylmethyl. An arylalkyl group can be unsubstituted or substituted with one or more suitable groups.

The term "heteroarylalkyl" refers to a heteroaryl ring radical as defined above directly bonded to an alkyl group as defined above. The heteroarylalkyl radical may be attached to the main structure at any carbon atom in the alkyl group that results in the creation of a stable structure.

The term "heteroalkylalkyl" refers to an alkyl group, as defined above wherein one or more of the alkyl group's hydrogen atom has been replaced with an heterocyclyl group as defined above. Examples of heterocyclylalkyl include but not limited to 1-ethylpyrrolidine or 1-ethylpiperidine "Substituted" refers to 1-3 substituents on the same position or on different positions with the same groups or different groups. Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, haloalkyl, substituted or unsubstituted alkoxy, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring.

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The term "subject" includes mammals (especially humans) and other animals, such as domestic animals (e.g., household pets including cats and dogs) and non-domestic animals (such as wildlife).

The term "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

The compounds of the present invention may form salts. Non-limiting examples of pharmaceutically acceptable salts forming part of this invention include salts derived from inorganic bases, salts of organic bases, salts of chiral bases, salts of natural amino acids and salts of non-natural amino acids. Certain compounds of the present invention are capable of existing in stereo isomeric forms (e.g., diastereomers, enantiomers, racemates, and combinations thereof). With respect to the overall compounds described by the formula (I), the present invention extends to these stereo isomeric forms and to mixtures thereof. To the extent prior art teaches synthesis or separation of particular stereoisomers, the different stereo isomeric forms of the present invention may be separated from one another by the methods known in the art, or a given isomer may be obtained by stereospecific or asymmetric synthesis. Tautomeric forms and mixtures of compounds described herein are also contemplated.

Pharmaceutically acceptable solvates includes hydrates and other solvents of crystallization (such as alcohols). The compounds of the present invention may form solvates with low molecular weight solvents by methods known in the art.

Pharmaceutical Compositions

The pharmaceutical compositions provided in the present invention include at least one compound described herein and at least one pharmaceutically acceptable excipient (such as a pharmaceutically acceptable carrier or diluent). Specifically, the contemplated pharmaceutical compositions include a compound(s) described herein in an amount sufficient to treat viral infection in a subject.

The compound of the present invention may be associated with a pharmaceutically acceptable excipient (such as a carrier or a diluent) or be diluted by a carrier, or enclosed within a carrier which can be in the form of a capsule, sachet, or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick-, sustained-, or delayed-release of the active ingredient after administration to the subject by employing procedures known in the art.

The pharmaceutical compositions described herein may be prepared, e.g., as described in *Remington: The Science and Practice of Pharmacy*, 20$^{th}$ Ed., 2003 (Lippincott Williams & Wilkins). For example, the active compound can be mixed with a carrier, or diluted by a carrier, or enclosed within a carrier, which may be in the form of an ampule, capsule, or sachet. When the carrier serves as a diluent, it may be a solid, semi-solid, or liquid material that acts as a vehicle, excipient, or medium for the active compound.

The pharmaceutical compositions may be, for example, capsules, tablets, aerosols, solutions, suspensions, liquids, gels, or products for topical application.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is specifically suitable.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Exemplary carriers for tablets, dragees, or capsules include lactose, cornstarch, and/or potato starch. A syrup or elixir can be used in cases where a sweetened vehicle can be employed.

A typical tablet that may be prepared by conventional tableting techniques.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, specifically aqueous solutions with the active compound dissolved in polyhydroxylated castor oil.

Methods of Treatment

The present invention provides compounds and pharmaceutical compositions thereof that are useful in the treatment of diseases, conditions and/or disorders mediated by viral infections. The connection between therapeutic effect and antiviral is illustrated. For example, PCT publication Nos. WO 01/07646, WO 01/65957, or WO 03/037908; US publication Nos. U.S. Pat. No. 4,598,095 or US 2002/0068757; EP publication Nos. EP 0989862 or EP 0724650; *Bioorganic & Medicinal Chemistry Letters*, 16, (6), 1712-1715, 2006; and references cited therein, all of which are incorporated herein by reference in their entirety and for the purpose stated.

The present invention further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV, HCV, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

The compounds of the present invention can obtain more advantageous effects than additive effects in the prevention or treatment of the above diseases when using suitably in combination with the available drugs. Also, the administration dose can be decreased in comparison with administration of either drug alone, or adverse effects of co administrated drugs other than antiviral can be avoided or declined.

Methods of Preparation

The compounds described herein may be prepared by techniques known in the art. In addition, the compounds described herein may be prepared by following the reaction sequence as depicted in Scheme-1 and 2. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereoisomers of the compounds in these schemes, unless otherwise specified, are also encompassed within the scope of this invention.

In a further aspect, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, C, $^{13}$C, $^{14}$C, $^{13}$N, $^{15}$O, $^{15}$O, $^{17}$O, $^{18}$O, $^{32}$P, $^{33}$P, $^{35}$S, $^{18}$F, $^{36}$Cl, $^{123}$I and $^{125}$I. Particular isotopes are —CD$_3$ or —C(D$_2$)-. Isotopically labeled compounds of the present inventions can generally be prepared by following procedures analogous to those disclosed in the Schemes and/or in the Examples herein below, by substituting an isotopically labeled reagent for a non-isotopically labeled reagent.

Compounds of the present invention can be synthesized from naturally occurring Betulin or Betulinic acid. Key intermediates required for synthesizing analogues are either commercially available, or can be prepared by the methods published in the literature. For example, the key intermediates in the present invention were prepared by modifying the procedures published in *Journal of organic chemistry* 2010, 75, 1285-1288; *Journal of organic chemistry* 2000, 65, 3934-3940; *Tetrahedron: asymmetry* 2008, 19, 302-308; or *Tetrahedron: asymmetry* 2003, 14, 217-223.

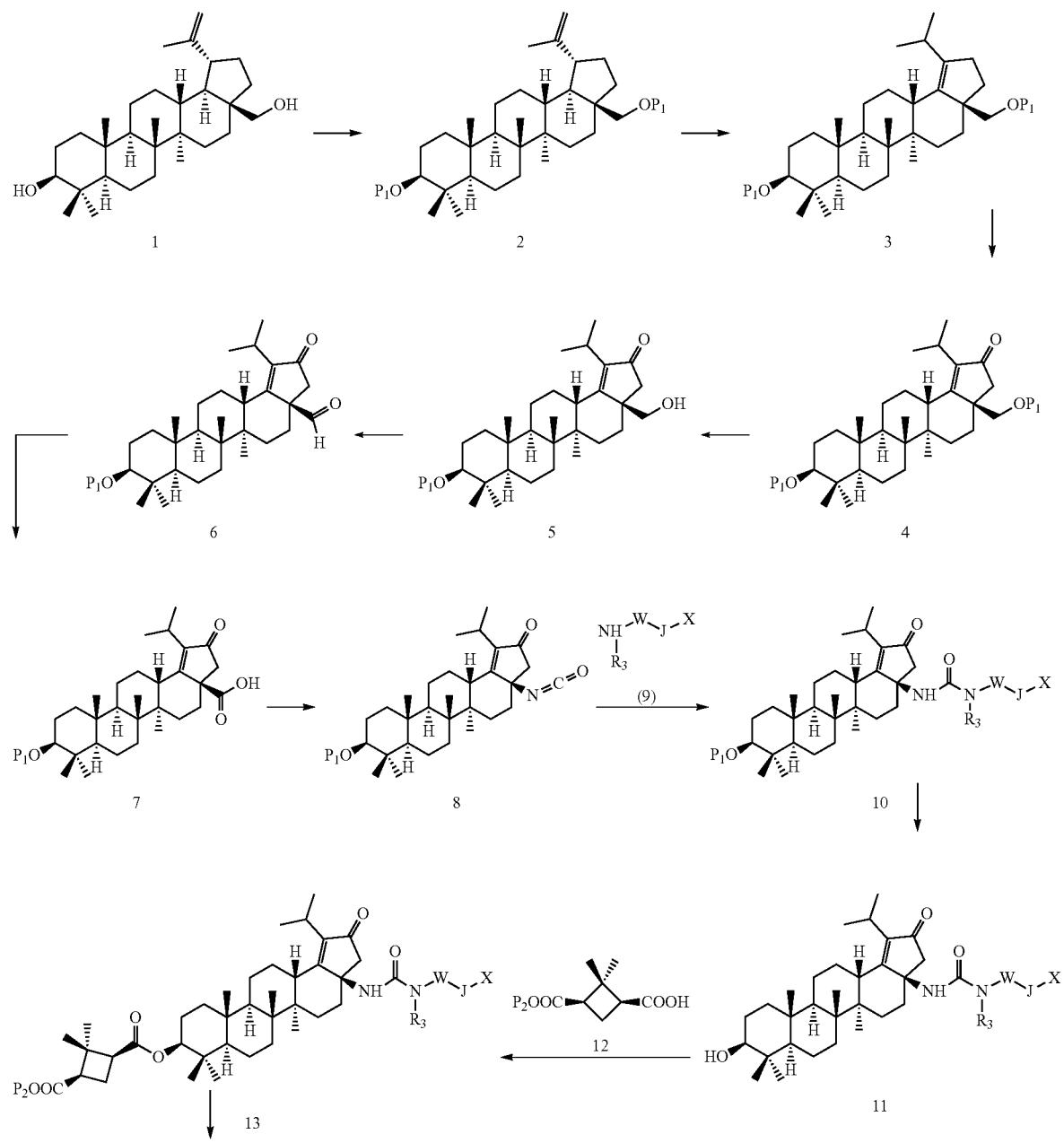

Scheme-1

-continued

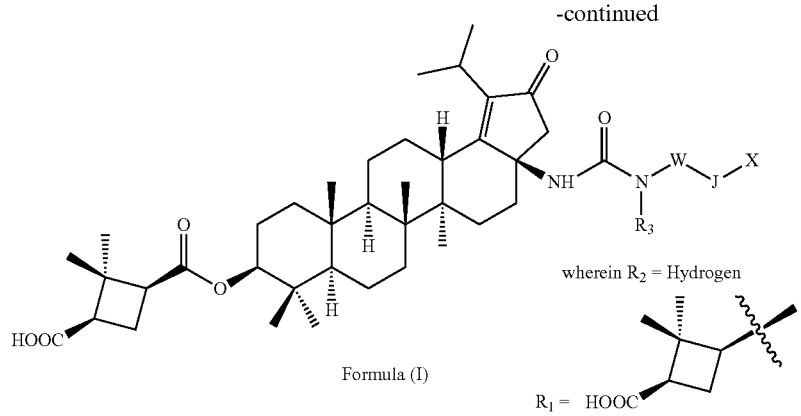

Formula (I)

wherein $R_2$ = Hydrogen $R_1$ = HOOC⟨...⟩

The compounds of formula (I) (wherein, $R_3$, W, J and X are same as defined above) can be prepared as described in Scheme-1 ($P_1$ is a protecting group such as acetyl or the like and $P_2$ is a protecting group such as benzyl or the like). The C-3 & C-28 di hydroxy compounds of formula (1) can be protected in different ways like
(a) With a suitable ester forming reagent such as anhydride with or without addition of a base or a catalyst under heating conditions or
(b) with a suitable ester forming reagents such as anhydrides or acid halides or mixed anhydrides in the presence of a base such as triethylamine (TEA) or N,N-diisopropylethylamine (DIPEA) or pyridine or the like in a solvent such as dichloromethane (DCM) or tetrahydrofuran (THF) or toluene or the like with or without addition of a catalyst such as 4-(Dimethylamino)pyridine (DMAP) under heating conditions or the like to give the C-3 & C-28 di hydroxy protected compounds of formula (2).

The C-3 & C-28 di hydroxy protected compounds of formula (2) containing the terminal double bond can be transferred to the internal double bond of compounds of formula (3) in the presence of hydrogen bromide (HBr) in acetic acid (AcOH), acetic acid (AcOH) and acetic anhydride ($Ac_2O$) in a solvent such as toluene or benzene or the like. The internal double bond of compounds of formula (3) can be converted to the enone compounds of formula (4) in the presence of reagents such as sodium dichromate dihydrate ($Na_2Cr_2O_7.2H_2O$), sodium acetate (NaOAc), acetic acid (AcOH) and acetic anhydride ($Ac_2O$) in a solvent such as toluene or benzene or the like. The enone compounds of formula (4) can be selectively deprotected at C-28 to give the C-28 hydroxy compounds of formula (5) in the presence of a base such as potassium hydroxide (KOH) or the like in the combination of solvents such as toluene:ethanol (EtOH) (1:1) or the like or with a reagent like Aluminium isopropoxide [$Al(OCH(CH_3)_2)_3$] in a solvent such as 2-propanol or the like. The C-28 hydroxy compounds of formula (5) can be converted to the C-28 aldehyde compounds of formula (6) in the presence of an oxidizing agent such as pyridinium chlorochromate (PCC) or pyridinium dichromate (PDC) or Dess-Martin periodinane (DMP) or Swern oxidation conditions in a solvent such as dichloromethane (DCM) or the like. The C-28 aldehyde compounds of formula (6) can be converted to the C-28 acid compounds of formula (7) in the presence of a oxidizing agent such as sodium chlorite ($NaClO_2$) or the like in the presence of a scavenger such as 2-methyl-2-butene or the like in the presence of a buffer such as sodium dihydrogen phosphate monohydrate ($NaH_2PO_4.H_2O$) or the like in the combination of solvents such as tert-butanol (t-BuOH), tetrahydrofuran (THF) and water ($H_2O$).

The C-28 acid compounds of formula (7) can be converted to the C-28 isocyanate compounds of formula (8) in the presence of a reagent such as diphenyl phosphoryl azide (DPPA) or the like in the presence of a base such as triethylamine (TEA) or N,N-Diisopropylethylamine (DIPEA) or the like in a solvent such as toluene or benzene or the like. The C-28 isocyanate compounds of formula (8) can be reacted with the amine of compounds of formula (9) in the presence of a base such as triethylamine (TEA) or N,N-Diisopropylethylamine (DIPEA) or the like in a solvent such as toluene or tetrahydrofuran (THF) or the like to give the C-28 ureas of compounds of formula (10). The C-3 protecting group of compounds of formula (10) can be deprotected to the C-3 hydroxy compounds of formula (11) in the presence of a inorganic base such as sodium hydroxide (NaOH) or potassium hydroxide (KOH) or lithium hydroxide (LiOH) or the like in the combination of solvents such as methanol (MeOH):tetrahydrofuran (THF):water ($H_2O$) (4:2:1) or the like.

The C-3 hydroxy compounds of formula (11) can be reacted with the acid of compounds of formula (12) to give the ester of compounds of formula (13) in different ways like
 a) Alcohol (11) and Acid (12) coupling with a reagent like 2,4,6-trichlorobenzoyl chloride in the presence of a base such as triethylamine (TEA) or N,N-Diisopropylethylamine (DIPEA) or the like and a catalyst such as 4-(Dimethylamino)pyridine (DMAP) in a solvent such as or dichloromethane (DCM) or Tetrahydrofuran (THF) or the like.
 b) Alcohol (11) and Acid (12) coupling in the presence of a coupling reagent such as 1-ethyl-3-(3-dimethylaminopropyl)carbodiimide (EDCI) or the like and a catalyst such as 4-(Dimethylamino)pyridine (DMAP) or the like in a solvent such as dichloromethane (DCM) or N,N-dimethylformamide (DMF) or the like.

The ester group in compounds of formula (13) can be deprotected to the corresponding acid of compounds of formula (I) in different ways like
 a) Ester group can be hydrolyzed in the presence of a aqueous solution of a inorganic base such as sodium hydroxide (NaOH) or potassium hydroxide (KOH) or the like in the combination of solvents such as tetrahydrofuran (THF) and methanol (MeOH) (1:1) or the like or b) Ester group can be deprotected in the presence of a catalyst such as palladium on carbon (10% Pd/C) and hydrogen source such as ammonium formate (HCOONH$_4$) or hydrogen gas (H$_2$) or the like in a solvent such as ethyl acetate (EtOAc) or methanol (MeOH) or combination of ethyl acetate (EtOAc) and methanol (MeOH) (1:1) or the like.

base such as triethylamine (TEA) or N,N-Diisopropylethylamine (DIPEA) or the like and a catalyst such as 4-(Dimethylamino)pyridine (DMAP) in a solvent such as dichloromethane (DCM) or Tetrahydrofuran (THF) or the like.

b) Alcohol (14) and Acid (12) coupling in the presence of a coupling reagent such as 1-ethyl-3-(3-dimethylam-

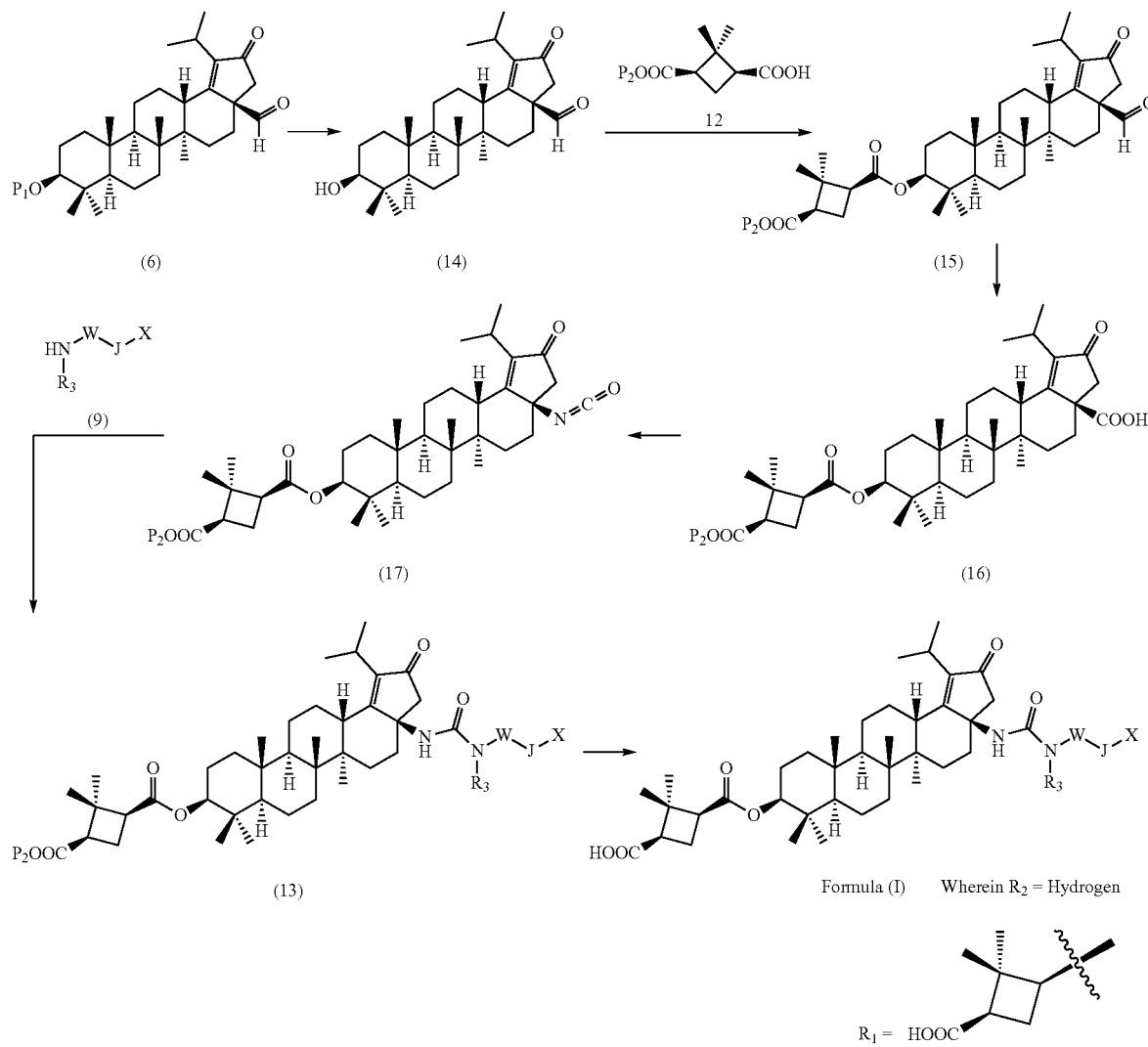

Scheme-2

The compounds of formula (I) (wherein, R$_3$, W, J and X are same as defined above) can be prepared as described in Scheme-2 (P$_1$ is a protecting group such as acetyl or the like and P$_2$ is a protecting group such as benzyl or the like).

The protecting group at C-3 of compounds of formula (6) can be deprotected to the C-3 hydroxy compounds of formula (14) with a reagent like zirconium tetrachloride (ZrCl$_4$) in combination of solvents such as methanol (MeOH) and dichloromethane (DCM) or the like.

The C-3 hydroxy compound of formula (14) can be coupled with the acid of compounds of formula (12) to give the ester of compounds of formula (15) in different ways like a) Alcohol (14) and Acid (12) coupling with a reagent like 2,4,6-trichlorobenzoyl chloride in the presence of a inopropyl)carbodiimide (EDCI) or the like and a catalyst such as 4-(Dimethylamino)pyridine (DMAP) or the like in a solvent such as dichloromethane (DCM) or N,N-dimethylformamide (DMF) or the like.

The C-28 aldehyde compounds of formula (15) can be converted to the C-28 acid compounds of formula (16) in the presence of a oxidizing agent such as sodium chlorite (NaClO$_2$) or the like in the presence of a scavenger such as 2-methyl-2-butene or the like in the presence of a buffer such as sodium dihydrogen phosphate (NaH$_2$PO$_4$) or the like in the combination of solvents such as tert-butanol (t-BuOH), tetrahydrofuran (THF) and water (H$_2$O).

The C-28 acid compounds of formula (16) can be converted to the C-28 isocyanate compounds of formula (17) in the presence of a reagent such as diphenyl phosphoryl azide (DPPA) or the like in the presence of a base such as triethylamine (TEA) or N,N-Diisopropylethylamine (DIPEA) or the like in a solvent such as toluene or benzene or the like. The C-28 isocyanate compounds of formula (17) can be reacted with the amine of compounds of formula (9) in the presence of a base such as triethylamine (TEA), or N,N-Diisopropylethylamine (DIPEA) or the like in a solvent such as toluene or tetrahydrofuran (THF) or the like to give the C-28 ureas of compounds of formula (13).

The ester group in compounds of formula (13) can be deprotected to the corresponding acid of compounds of formula (I) in different ways as depicted in scheme-1. The abbreviations used in the entire specification may be summarized herein below with their particular meaning: $NaBH_4$ (sodium borohydride); $NaClO_2$ (sodium chlorite); DIPEA (N,N-Diisopropylethylamine); ° C. (degree Celsius); δ (delta); ppm (parts per million); % (percentage); DMSO-$d_6$ (Deuterated DMSO); d (doublet); dd (Doublet of doublet); EtOH (Ethanol); EtOAc (Ethyl acetate); g or gr (gram); H or $H_2$ (Hydrogen); HCl (Hydrochloric acid); h or hrs (hour(s)); Hz (Hertz); HPLC (High-performance liquid chromatography); mmol(s) (millimole(s)); M (Molar); N (Normality); ml (milliliter); mg(s) (milligram(s)); m (multiplet); MHz (Megahertz); ESI-MS (Electron spray Ionization Mass spectra); min (Minutes); mM (millimolar); NaOH (Sodium hydroxide); $N_2$ (Nitrogen); NMR (Nuclear magnetic resonance spectroscopy); s (singlet); TEA (Triethylamine); TLC (Thin Layer Chromatography); THF (Tetrahydrofuran); tert (Tertiary); TFA/$CF_3COOH$ (Trifluoro acetic acid); t (Triplet); IC (Inhibitory concentration), nm or nM (Nano molar); pH (Pouvoir hydrogen); $(Boc)_2O$ (Di-tert-butyl dicarbonate); DCM (dichloromethane); DMF (N,N-dimethylformamide); DMAP (4-(Dimethylamino)pyridine); eq (equivalent); Ltr or L (Liter); $CDCl_3$ (Deuterated chloroform); J (Coupling constant); $J_{AB}$ (Coupling constant); $NaH_2PO_4$ (Sodium dihydrogen phosphate); $NaH_2PO_4.H_2O$ (Sodium dihydrogen phosphate monohydrate); AcOH (Acetic acid); $NaCNBH_3$ (Sodium cyanoborohydride); ABq (AB quartet); MTBE (Methyl tert-butyl ether); HBr (Hydrogen bromide); $Ac_2O$ (Acetic anhydride); $NaHCO_3$ (Sodium bicarbonate); $Na_2SO_4$ (Sodium sulphate); KOH (Potassium hydroxide); MeOH (methanol); EDCI (1-Ethyl-3-(3-dimethylaminopropyl)carbodiimide); br.s. (broad singlet); DPPA (Diphenyl phosphoryl azide).

EXPERIMENTAL

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and examples may be further implemented as disclosed by variously altering the following examples, substituents, reagents, or conditions.

Intermediates

Intermediate-1: Synthesis of (3aR,5aR,5bR,7aR,9S, 11aR,11bR,13aS)-3a-isocyanato-1-isopropyl-5a, 5b,8,8,11a-pentamethyl-2-oxo-3,3a,4,5,5a,5b,6,7,7a, 8,9,10,11,11a,11b,12,13,13a-octadeca hydro-2H-cyclopenta[a]chrysen-9-yl acetate

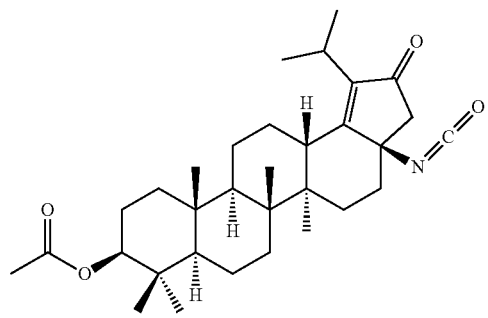

Step 1: ((1R,3aS,5aR,5bR,7aR,9S,11aR,11bR,13aR, 13bR)-9-acetoxy-5a,5b,8,8,11a-pentamethyl-1-(prop-1-en-2-yl)icosahydro-3aH-cyclopenta[a]chrysen-3a-yl)methyl acetate

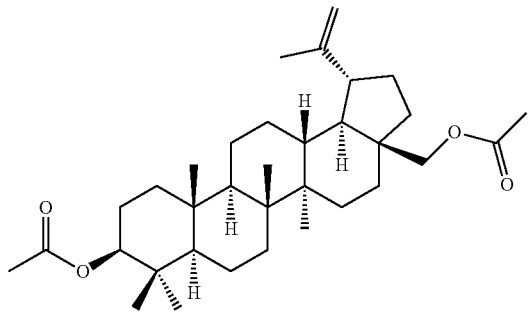

A mixture of (1R,3aS,5aR,5bR,7aR,9S,11aR,11bR,13aR, 13bR)-3a-(hydroxymethyl)-5a,5b,8,8,11a-pentamethyl-1-(prop-1-en-2-yl)icosahydro-1H-cyclopenta[a]chrysen-9-ol (250 g, 0.568 mol, 1.0 eq) and acetic anhydride (2.23 Ltr) were stirred at 140° C. for about 1.5 h. After completion of the reaction (monitored by TLC), the reaction mixture was cooled down to room temperature and then stirred at 0° C. for 30 minutes. The obtained solid was filtered, washed with water (2×1000 ml) and dried under vacuum to obtain the desired product (264 g, 88.7% yield) as an off-white solid. $^1$H NMR (300 MHz, $CDCl_3$): δ ppm 4.68 (s, 1H), 4.58 (s, 1H), 4.50-4.43 (m, 1H), 4.25 (d, J=10.8 Hz, 1H), 3.85 (d, J=11.1 Hz, 1H), 2.50-2.40 (m, 1H), 2.07 (s, 3H), 2.04 (s, 3H), 2.0-0.94 (m, 23H), 1.68 (s, 3H), 1.03 (s, 3H), 0.96 (s, 3H), 0.88-0.75 (m, 10H).

Step 2: ((3aS,5aR,5bR,7aR,9S,11aR,11bR,13aS)-9-acetoxy-1-isopropyl-5a,5b,8,8,11a-pentamethyl-2,3,4,5,5a,5b,6,7,7a,8,9,10,11,11a,11b,12,13,13a-octadecahydro-3aH-cyclopenta[a]chrysen-3a-yl)methyl acetate

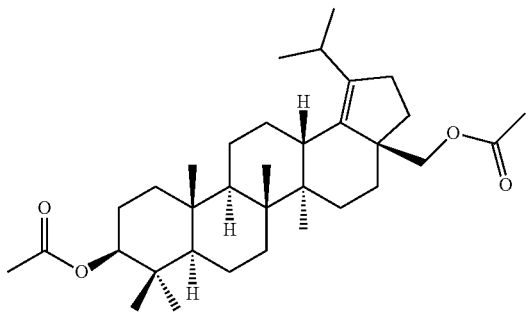

HBr in acetic acid (528 ml, 33%), was added to a suspension of ((1R,3aS,5aR,5bR,7aR,9S,11aR,11bR,13aR,13bR)-9-acetoxy-5a,5b,8,8,11a-pentamethyl-1-(prop-1-en-2-yl)icosahydro-3aH-cyclopenta[a]chrysen-3a-yl)methyl acetate (step 1, 264 g, 0.501 mol, 1.0 eq) in toluene (528 ml), Ac$_2$O (528 ml) and acetic acid (528 ml) previously heated at 106° C. The reaction mixture was stirred and heated at this temperature for about 1.5 h. After cooling down to room temperature, the mixture was quenched with sodium acetate (324 g). The resulting reaction mixture was evaporated to dryness. The residue was taken up in CH$_2$Cl$_2$ and the organic phase was washed with water. The organic layer was dried over sodium sulfate and evaporated under reduced pressure. The residue was recrystallized over ethanol and CH$_2$Cl$_2$ gave the desired product (175 g, 66.3% yield) as an off-white solid. $^1$H NMR (300 MHz, CDCl$_3$): δ ppm 4.52-4.45 (m, 1H), 4.03 (d, J=10.8 Hz, 1H), 3.98 (d, J=10.8 Hz, 1H), 3.19-3.08 (m, 1H), 2.46-2.38 (m, 1H), 2.28-2.22 (m, 2H), 2.04 (s, 3H), 2.03 (s, 3H), 2.0-1.83 (m, 2H), 1.78-1.61 (m, 6H), 1.57-1.44 (m, 3H), 1.43-1.08 (m, 8H), 1.06 (s, 3H), 1.02-0.88 (m, 12H), 0.84 (s, 3H), 0.83 (s, 3H), 0.78 (m, 1H).

Step 3: ((3aR,5aR,5bR,7aR,9S,11aR,11bR,13aS)-9-acetoxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysen-3a-yl)methyl acetate

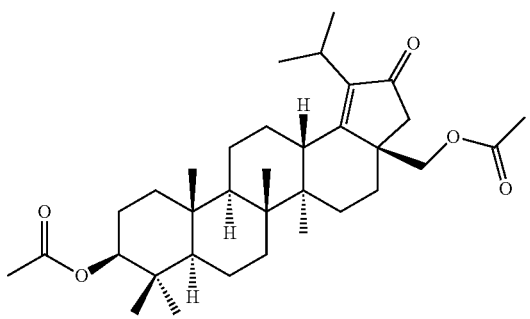

To a stirred solution of ((3aS,5aR,5bR,7aR,9S,11aR,11bR,13aS)-9-acetoxy-1-isopropyl-5a,5b,8,8,11a-pentamethyl-2,3,4,5,5a,5b,6,7,7a,8,9,10,11,11a,11b,12,13,13a-octadecahydro-3aH-cyclopenta[a]chrysen-3a-yl)methyl acetate (step 2, 130 g, 247.14 mmol, 1.0 eq) in Toluene (1669 ml) was added AcOH (2210 ml), Ac$_2$O (536 ml), sodium dichromate dihydrate (88.44 g, 296.80 mmol, 1.2 eq) and sodium acetate (115.88 g, 1413.2 mmol, 5.7 eq). The reaction mixture was stirred and heated at 60° C. for overnight. TLC indicated starting material was consumed and the desired product was observed. After cooling down, the reaction mixture diluted with water (750 ml) and extracted with ethyl acetate (500 ml). The organic phase was washed successively with water (2×500 ml), saturated solution of sodium carbonate (500 ml) and brine solution (500 ml). The organic layer was dried over sodium sulfate, filtered and concentrated under reduced pressure to afford a sticky oil. The sticky oil was triturated with methanol (1000 ml) and stirred at 0° C. for about 1 h. The precipitates formed were collected by filtration and dried under vacuum to obtain the desired product (80 g, 60% yield) as a white solid. $^1$H NMR (300 MHz, CDCl$_3$): δ ppm 4.48 (dd, J=10.2, 6.0 Hz, 1H), 4.33 (d, J=10.8 Hz, 1H), 4.05 (d, J=11.1 Hz, 1H), 3.22-3.12 (m, 1H), 2.86 (dd, J=12.3, 3.3 Hz, 1H), 2.38 (d, J=18.3 Hz, 1H), 2.05 (s, 3H), 1.99 (s, 3H), 1.93-0.75 (m, 40H).

Step 4: (3aR,5aR,5bR,7aR,9S,11aR,11bR,13aS)-3a-(hydroxymethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

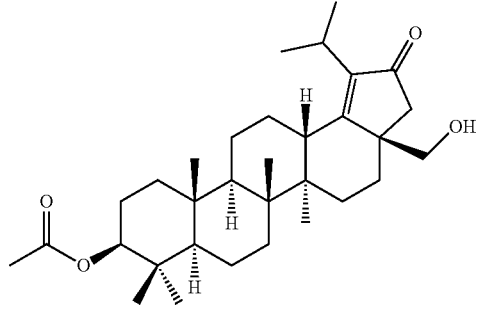

To a stirred solution of ((3aR,5aR,5bR,7aR,9S,11aR,11bR,13aS)-9-acetoxy-1-isopropyl-5a,5b,8,8,11a-pentamethyl-2-oxo2,3,4,5,5a,5b,6,7,7a,8,9,10,11,11a,11b,12,13,13a-octadecahydro-3aH-cyclopenta[a]chrysen-3a-yl)methyl acetate (step 3, 80 g, 148.09 mmol, 1.0 eq) in a mixture of ethanol (2.28 L):toluene (2.28 L) (1:1) was added potassium hydroxide (9.9 g, 172.50 mmol, 1.197 eq). The reaction mixture was stirred vigorously at room temperature for about 1 h. After completion of the reaction monitored by TLC, the reaction mixture was neutralized with aqueous 1N HCl and evaporated to dryness. The obtained residue was taken up in water and a small amount of acetone. The precipitates formed were collected by filtration, washed with water and dried in vacuo to obtain the desired product (66 g, 89.5% yield) as a white solid. $^1$H NMR (300 MHz, CDCl$_3$): δ ppm 4.49 (dd, J=10.2, 5.7 Hz, 1H), 3.73 (d, J=10.8 Hz, 1H), 3.66 (d, J=10.8 Hz, 1H), 3.25-3.14 (m, 1H), 2.78 (dd, J=12.3, 3.0 Hz, 1H), 2.44 (d, J=18.6 Hz, 1H), 2.05 (s, 3H), 2.02-1.28 (m, 16H), 1.24-1.17 (m, 7H), 1.13 (s, 3H), 1.12-0.97 (m, 1H), 0.94 (s, 3H), 0.92 (s, 3H), 0.86 (s, 3H), 0.85 (s, 3H), 0.80 (m, 1H).

Step 5: (3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

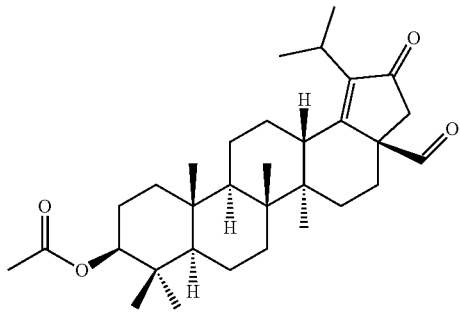

To a stirred solution of (3aR,5aR,5bR,7aR,9S,11aR,11bR,13aS)-3a-(hydroxymethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 4, 66 g, 132.22 mmol, 1.0 eq) in $CH_2Cl_2$ (3.88 Ltr) at room temperature was added pyridinium chlorochromate (85.2 g, 396.66 mmol, 3.0 eq) and silicagel (100-200 mesh) (84.3 g). The reaction mixture was stirred at room temperature for about 1 h. After completion of the reaction monitored by TLC, the reaction mixture was diluted with water (500 ml) and extracted with $CH_2Cl_2$. The combined organic extracts were washed with water (2×500 ml) and saturated sodium bicarbonate solution (500 ml). The organic layer was dried over sodium sulfate and evaporated under reduced pressure. The residue was stirred with ethanol (250 ml) at room temperature for about 30 minutes. The precipitates formed were collected by filtration and dried under vacuum to obtain the desired product (52 g, 79.1% yield) as a white solid. $^1$H NMR (300 MHz, $CDCl_3$): δ ppm 9.31 (s, 1H), 4.48 (dd, J=10.5, 6.0 Hz, 1H), 3.32-3.18 (m, 1H), 2.59-2.52 (m, 1H), 2.43-2.33 (m, 2H), 2.10-2.0 (m, 2H), 2.05 (s, 3H), 1.97-1.08 (m, 21H), 1.03 (s, 3H), 0.94 (s, 3H), 0.90 (s, 3H), 0.84 (s, 6H), 0.79 (m, 1H).

Step 6: Synthesis of (3aR,5aR,5bR,7aR,9S,11aR,11bR,13aS)-9-acetoxy-1-isopropyl-5a, 5b,8,8,11a-pentamethyl-2-oxo-2,3,4,5,5a,5b,6,7,7a,8,9,10,11,11a,11b,12,13,13a-octadecahydro-3aH-cyclopenta[a]chrysene-3a-carboxylic acid

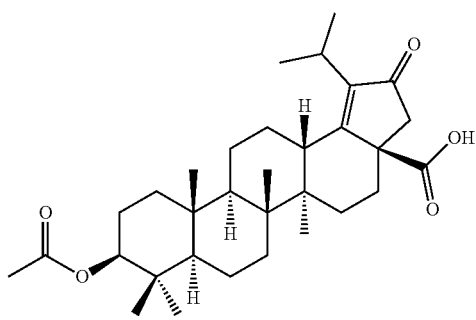

To an ice-cooled solution of (3aR,5aR,5bR,7aR,9S,11aR,11bR,13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 5, 15.0 g, 30.24 mmol, 1.0 eq) in t-butanol (1500 ml), THF (280 ml) and 2-methyl 2-butene (8 ml) was added slowly a solution of $NaClO_2$ (32.84 g, 362.9 mmol, 12.0 eq) and $NaH_2PO_4 \cdot H_2O$ (41.73 g, 302.4 mmol, 10.0 eq) in water (34 ml) about 15 minutes. After stirring at 0° C. for about 10 minutes, the reaction mixture was warmed to room temperature and stirred for about another 30 minutes. TLC indicated starting material was consumed and the desired product was observed. The reaction mixture was diluted with water (100 ml) and extracted with ethyl acetate (3×250 ml). The combined organic extracts were washed with water (100 ml), dried over sodium sulfate, filtered and evaporated under reduced pressure. The residue was treated with n-hexane (150 ml), solid formed was collected by filtration and dried under vacuum to obtain the desired product (15.0 g, 97% yield) as a white solid. $^1$H NMR (300 MHz, $CDCl_3$): δ ppm 4.52-4.45 (m, 1H), 3.27-3.18 (m, 1H), 2.78-2.73 (m, 1H), 2.58 (d, J=18.6 Hz, 1H), 2.50-2.43 (m, 1H), 2.18 (d, J=18.9 Hz, 1H), 2.05 (s, 3H), 2.02-1.97 (m, 1H), 1.97-1.82 (m, 3H), 1.78-1.0 (m, 18H), 1.05 (s, 3H), 0.94 (s, 3H), 0.91 (s, 3H), 0.85 (s, 3H), 0.84 (s, 3H), 0.82-0.79 (m, 1H).

Step 7: Synthesis of (3aR,5aR,5bR,7aR,9S,11aR,11bR,13aS)-3a-isocyanato-1-isopropyl-5a,5b,8,8,11a-pentamethyl-2-oxo-3,3a,4,5,5a,5b,6,7,7a,8,9,10,11,11a,11b,12,13,13a-octadeca hydro-2H-cyclopenta[a]chrysen-9-yl acetate

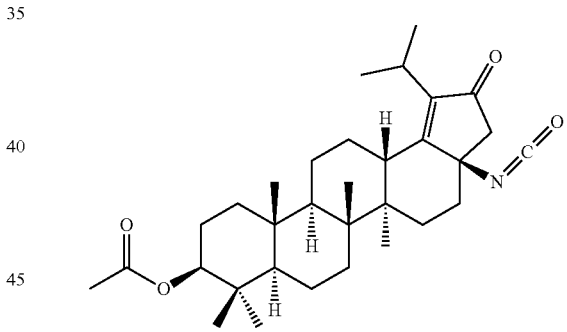

To a stirred solution of (3aR,5aR,5bR,7aR,9S,11aR,11bR,13aS)-9-acetoxy-1-isopropyl-5a,5b,8,8,11a-pentamethyl-2-oxo-2,3,4,5,5a,5b,6,7,7a,8,9,10,11,11a,11b,12,13,13a-octadeca hydro-3aH-cyclopenta[a]chrysene-3a-carboxylic acid (step 6, 15.0 g, 29.29 mmol, 1.0 eq) in toluene (150 ml) was added triethylamine (3.549 g, 35.15 mmol, 1.2 eq) and DPPA (9.66 g, 35.15 mmol, 1.2 eq). The reaction mixture was stirred at room temperature for about 3 hours. TLC indicated starting material was consumed and the desired product was observed. The reaction mixture was concentrated to dryness. The residue was purified by silicagel column chromatography by using 60% ethyl acetate:hexane as an eluent to obtain the desired product (11.0 g, 73.76% yield) as a white solid. $^1$H NMR (300 MHz, $CDCl_3$): δ ppm 4.49 (dd, J=9.9, 6.0 Hz, 1H), 3.18-3.10 (m, 1H), 3.01 (dd, 1H), 2.59 (d, J=18.6 Hz, 1H), 2.42 (d, J=18.6 Hz, 1H), 2.18-2.10 (m, 1H), 2.05 (s, 3H), 2.02-1.65 (m, 6H), 1.58-1.25 (m, 9H), 1.25-1.02 (m, 10H), 0.94 (s, 3H), 0.91 (s, 3H), 0.86 (s, 6H), 0.82-0.78 (m, 1H).

Intermediate-2: Synthesis of 1-benzyl 3-((3aR,5aR, 5bR,7aR,9S,11aR,11bR,13aS)-3a-isocyanato-1-isopropyl-5a,5b,8,8,11a-pentamethyl-2-oxo3,3a,4,5,5a, 5b,6,7,7a,8,9,10,11,11a,11b,12,13,13a-octadecahydro-2H-cyclopenta[a]chrysen-9-yl) (1R, 3S)-2,2-dimethylcyclobutane-1,3-dicarboxylate

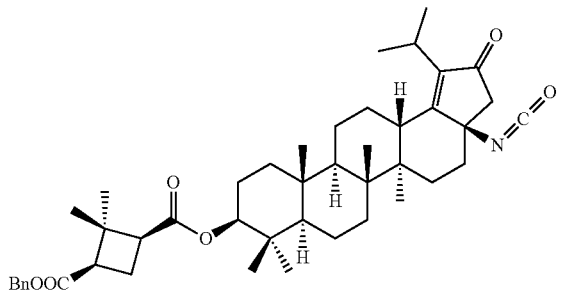

Step 1: (3aR,5aR,5bR,7aR,9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b,12,13, 13a-octadecahydro-3aH-cyclopenta[a]chrysene-3a-carbaldehyde

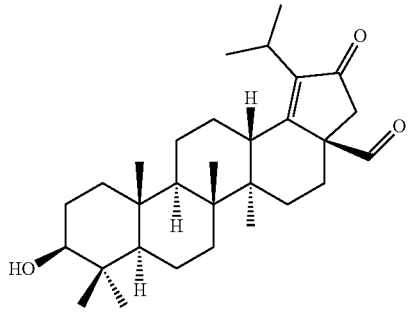

To a stirred solution of (3aR,5aR,5bR,7aR,9S,11aR,11bR, 13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadeca hydro-2H-cyclopenta[a]chrysen-9-yl acetate (Intermediate-1, step 5, 24.0 g, 48.38 mmol, 1.0 eq) in methanol (96 ml) and DCM (246 ml) was added Zirconium tetrachloride (12.89 g, 58.06 mmol, 1.19 eq) in portions. The reaction was warmed to approximately 45-55° C. and stirred for 36 h. After completion of the reaction monitored by TLC, the reaction was then treated with water (4 ml) and heated at 45-55° C. for 30 minutes. The reaction mixture was cooled to room temperature and evaporated under vacuum at 40° C. to 60 ml. Dichloromethane (180 ml) was added and the reaction was treated with 1N HCl (96 ml), mixed thoroughly and the layers were allowed to separate. Afterwards, the upper aqueous layer was washed with dichloromethane (16 ml). Next, the combined organic layer was washed with 1N HCl (96 ml) and evaporated under vacuum (at bath temp of 40° C.) to approximately 54 ml. Acetonitrile (190 ml) was added and the reaction was warmed to 60° C., thus forming a clear solution. Next was slowly added, 3N HCl (4 ml), which resulted in precipitate formation, reaction mixture was heated at 60° C. until dimethyl acetal hydrolysis was complete, followed by addition of water (220 ml). The reaction was allowed to cool to 10° C. and then the mixture was filtered and the resultant solid was rinsed with CH₃CN/ H₂O (1:1, 96 ml). The solid was then slurryed in 200 ml of heptane at 85-100° C. for about 3 h. The slurry was then cooled to room temperature, filtered and dried under vacuum at 40° C. to give the title compound (20.0 g) as a white solid.

Step 2: Synthesis of 1-benzyl 3-((3aR,5aR,5bR, 7aR,9S,11aR,11bR,13aS)-3a-formyl-1-isopropyl-5a, 5b,8,8,11a-pentamethyl-2-oxo-3,3a,4,5,5a,5b,6,7,7a, 8,9,10,11,11a, b,12,13,13a-octadecahydro-2H-cyclopenta[a]chrysen-9-yl) (1R,3S)-2,2-dimethylcyclobutane-1,3-dicarboxylate

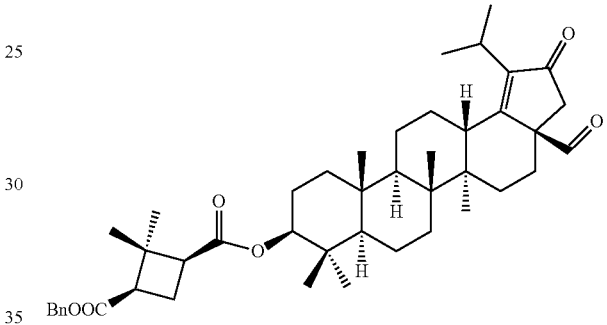

To a stirred solution of (3aR,5aR,5bR,7aR,9S,11aR,11bR, 13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysene-3a-carbaldehyde (step 1, 20.0 g, 44.05 mmol, 1.0 eq) and (1S,3R)-3-((benzyloxy)carbonyl)-2,2-dimethylcyclobutane-1-carboxyli-cacid (prepared as described in WO/2011/007230 A2, 17.31 g, 66.07 mmol, 1.5 eq) in DCM (400 ml) at 0° C. were added triethylamine (29.23 ml, 220.26 mmol, 5.0 eq), DMAP (2.68 g, 22.02 mmol, 0.5 eq) and 2,4,6-trichlorobenzoyl chloride (14.75 ml, 110.13 mmol, 2.5 eq). The reaction mixture was flushed with nitrogen and allowed to stir at room temperature for overnight. TLC indicated starting material was consumed and the desired product was observed. The reaction mixture was diluted with water (500 ml) and extracted with DCM (2×500 ml). The combined organic extracts were dried over Na₂SO₄, filtered and evaporated under reduced pressure. The residue was purified by silicagel column chromatography by using 10% MeOH:DCM as an eluent to obtain the desired product (25.0 g, 81.3% yield) as a white solid. $^1$H NMR (300 MHz, CDCl₃): δ ppm 9.31 (s, 1H), 7.37-7.32 (m, 5H), 5.15, 5.09 (ABq, $J_{AB}$=12.3 Hz, 2H), 4.45 (dd, J=11.4, 4.8 Hz, 1H), 3.31-3.20 (m, 1H), 2.86-2.73 (m, 2H), 2.70-2.61 (m, 1H), 2.59-2.52 (m, 1H), 2.37 (d, J=18.9 Hz, 2H), 2.09-1.99 (m, 3H), 1.99-1.80 (m, 2H), 1.78-1.64 (m, 3H), 1.63-1.35 (m, 7H), 1.32 (s, 3H), 1.32-1.20 (m, 8H), 1.20-1.15 (m, 1H), 1.03 (s, 3H), 0.96 (s, 3H), 0.94 (s, 3H), 0.90 (s, 3H), 0.85 (s, 3H), 0.84 (s, 3H), 0.83-0.77 (m, 1H).

Step 3: Synthesis of (3aR,5aR,5bR,7aR,9S,11aR, 11bR,13aS)-9-(((1S,3R)-3-((benzyloxy) carbonyl)-2, 2-dimethylcyclobutane-1-carbonyl)oxy)-1-isopropyl-5a,5b,8,8,11a-pentamethyl-2-oxo-2,3,4,5,5a,5b,6,7, 7a,8,9,10,11,11a,11b,12,13,13a-octadecahydro-3aH-cyclopenta[a]chrysene-3a-carboxylic acid

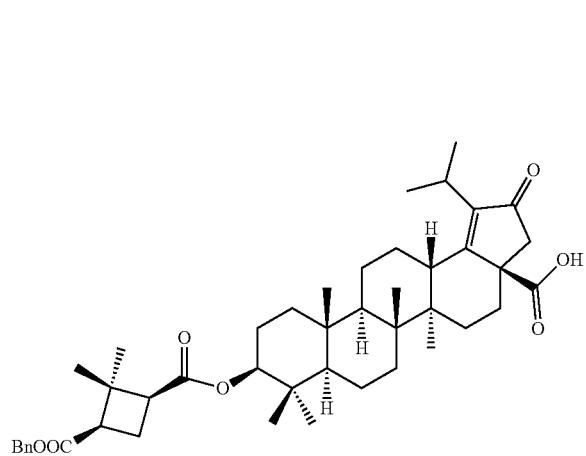

To an ice cooled solution of 1-benzyl 3-((3aR,5aR,5bR, 7aR,9S,11aR,11bR,13aS)-3a-formyl-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclo butane-1,3-dicarboxylate (step 2, 25.0 g, 35.81 mmol, 1.0 eq) in t-butanol (522 ml), THF (250 ml) and 2-methyl 2-butene (16.75 ml) was added slowly a solution of NaClO$_2$ (38.68 g, 429.79 mmol, 12.0 eq) and NaH$_2$PO$_4$ (42.62 g, 358.16 mmol, 10.0 eq) in water (250 ml) over 15 minutes. After stirring at 0° C. for about 10 minutes, the reaction mixture was warmed to room temperature and stirred for another 30 minutes. TLC indicated starting material was consumed and the desired product was observed. The reaction mixture was diluted with water (300 ml) and extracted with ethyl acetate (3×500 ml). The combined organic extracts were washed with water (300 ml), dried over sodium sulfate, filtered and evaporated under reduced pressure. The residue was triturated with acetonitrile (150 ml), precipitates formed were collected by filtration and dried under vacuum to obtain the desired product (22.0 g, 86.2% yield) as a white solid. $^1$H NMR (300 MHz, CDCl$_3$): δ ppm 7.35 (m, 5H), 5.15, 5.10 (ABq, J$_{AB}$=12.6 Hz, 2H), 4.45 (dd, J=11.1, 4.5 Hz, 1H), 3.26-3.16 (m, 1H), 2.86-2.71 (m, 3H), 2.70-2.54 (m, 2H), 2.52-2.43 (m, 1H), 2.19 (d, J=18.9 Hz, 1H), 2.09-1.98 (m, 2H), 1.98-1.82 (m, 2H), 1.80-1.65 (m, 2H), 1.64-1.43 (m, 5H), 1.43-1.36 (m, 2H), 1.34 (s, 3H), 1.33-1.18 (m, 9H), 1.16-1.09 (m, 1H), 1.05 (s, 3H), 0.96 (s, 3H), 0.94 (s, 3H), 0.91 (s, 3H), 0.85 (s, 3H), 0.84 (s, 3H), 0.83-0.78 (m, 1H).

Step 4: Synthesis of 1-benzyl 3-((3aR,5aR,5bR, 7aR,9S,11aR,11bR,13aS)-3a-isocyanato-1-isopropyl-5a,5b,8,8,11a-pentamethyl-2-oxo-3,3a,4,5,5a,5b, 6,7,7a,8,9,10,11,11b,12,13,13a-octadecahydro-2H-cyclopenta[a]chrysen-9-yl) (1R,3S)-2,2-dimethylcyclobutane-1,3-dicarboxylate

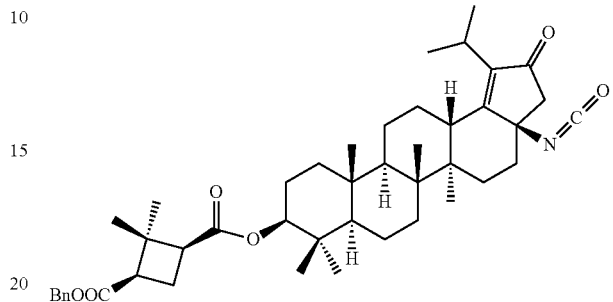

To a stirred solution of (3aR,5aR,5bR,7aR,9S,11aR,11bR, 13aS)-9-(((1S,3R)-3-((benzyloxy)carbonyl)-2,2-dimethyl-cyclobutane-1-carbonyl)oxy)-1-isopropyl-5a,5b,8,8,11a-pentamethyl-2-oxo-2,3,4,5,5a,5b,6,7,7a,8,9,10,11,11a,11b, 12,13,13a-octadecahydro-3aH-cyclopenta[a]chrysene-3a-carboxylic acid (step 3, 5.0 g, 6.993 mmol, 1.0 eq) in toluene (50 ml) was added triethylamine (1.17 ml, 8.39 mmol, 1.2 eq) followed by diphenyl phosphoryl azide (1.81 ml, 8.39 mmol, 1.2 eq). The reaction mixture was stirred at room temperature for about 4 hours. TLC indicated starting material was consumed and the desired product was observed. The reaction mixture was concentrated to dryness. The residue was purified by silicagel column chromatography by using 0-20% ethyl acetate in hexane gradient. The fractions containing the expected product were combined and concentrated under reduced pressure to obtain the desired product (3.0 g, 60.25% yield) as a white solid. $^1$H NMR (300 MHz, CDCl$_3$): δ ppm 7.37-7.32 (m, 5H), 5.13, 5.08 (ABq, J$_{AB}$=12.3 Hz, 2H), 4.43 (dd, J=11.1, 4.5 Hz, 1H), 3.25-3.09 (m, 1H), 2.85-2.71 (m, 2H), 2.69-2.40 (m, 3H), 2.16-1.80 (m, 5H), 1.77-1.45 (m, 8H), 1.43-1.26 (m, 7H), 1.25-1.14 (m, 8H), 1.03 (s, 3H), 0.94 (s, 3H), 0.90 (s, 3H), 0.89 (s, 3H), 0.83 (s, 3H), 0.82 (s, 3H), 0.81-0.75 (m, 1H); ESI-MS: m/z 734.43 (M+Na)$^+$.

Intermediate-3: Synthesis of N-(4-chlorobenzyl)-N$^2$, N$^2$-dimethylethane-1,2-diamine

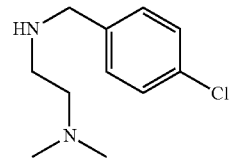

To a stirred solution of 4-chlorobenzaldehyde (15.0 g, 107.14 mmol, 1.0 eq) in methanol (250 ml) at 0° C. was added N$^1$,N$^1$-dimethylethane-1,2-diamine (11.65 ml, 107.14 mmol, 1.0 eq) and sodium borohydride (3.85 g, 107.14 mmol, 1.0 eq). The reaction mixture was allowed to stir at room temperature for about 16 hours. After completion of the reaction (monitored by TLC), the reaction mixture was cooled to 0° C., quenched with saturated ammonium chloride solution (20 ml) and extracted with ethyl acetate (3×200 ml). The combined organic extracts were washed with water (100 ml), dried over sodium sulfate, filtered and evaporated under reduced pressure to obtain the desired product (15.0 g, 66% yield) as a colourless liquid. ¹H NMR (300 MHz, DMSO-d₆): δ ppm 7.32-7.23 (m, 4H), 3.76 (s, 2H), 2.66 (t, J=6.3 Hz, 2H), 2.41 (t, J=6.3 Hz, 2H), 2.19 (s, 6H); ESI-MS: m/z 213.08 (M+H)⁺.

Intermediate 4: Synthesis of
1-(4-chlorophenyl)cyclopropan-1-amine

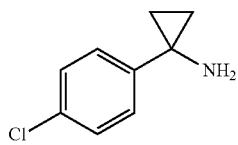 [SMILES: NC1(c2ccc(Cl)cc2)CC1]

Step 1: Synthesis of
1-(4-chlorophenyl)cyclopropane-1-carbonitrile

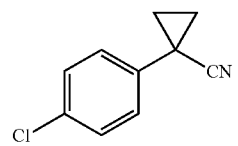 [SMILES: N#CC1(c2ccc(Cl)cc2)CC1]

A suspension of 55% sodium hydride (25.27 g, 1052.9 mmol, 5.3 eq) and THF (200 ml) under nitrogen atmosphere was heated to 40° C. and a solution of 2-(4-chlorophenyl) acetonitrile (30.0 g, 198.67 mmol, 1.0 eq) in THF (50 ml) was added dropwise over 30 minutes. The mixture was stirred at 40° C. for about 30 minutes and a solution of 1,2-dibromoethane (74.3 g, 397.35 mmol, 2.0 eq) in THF (50 ml) was added dropwise over 30 minutes. The reaction mixture was stirred at 40° C. for about 1 hour. TLC indicated starting material was consumed and the desired product was observed. The reaction mixture was cooled to 0° C., quenched with ice water (250 ml) and extracted with ethyl acetate (3×400 ml). The combined organic extracts were washed with brine solution (400 ml), dried over sodium sulfate, filtered and evaporated under reduced pressure to obtain the desired product (30.0 g) as a semi solid, which is used as such for next step without further purification. ¹H NMR (300 MHz, CDCl₃): δ ppm 7.33 (d, J=8.7 Hz, 2H), 7.24 (d, J=8.7 Hz, 2H), 1.78-1.71 (m, 2H), 1.42-1.35 (m, 2H).

Step 2: Synthesis of
1-(4-chlorophenyl)cyclopropane-1-carboxylic acid

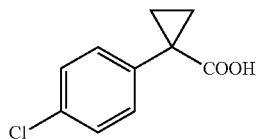 [SMILES: O=C(O)C1(c2ccc(Cl)cc2)CC1]

A stirred solution of 1-(4-chlorophenyl)cyclopropane-1-carbonitrile (step 1, 30.0 g, 169.49 mmol, 1.0 eq), sodium hydroxide (20.3 g, 508.47 mmol, 3.0 eq), diethylene glycol (120 ml) and water (35.4 ml) was refluxed for about 18 hours. TLC indicated starting material was consumed and the desired product was observed. The reaction mixture was poured into water (1800 ml) and acidified to pH~4.0 with concentrated HCl (54 ml). The generated crystals were collected by filtration and dried under vacuum to obtain the desired product (30.0 g, 90.3% yield) as a pale-brown colour solid. ¹H NMR (300 MHz, DMSO-d₆): δ ppm 12.40 (br.s., 1H), 7.34 (m, 4H), 1.48-1.42 (m, 2H), 1.16-1.10 (m, 2H).

Step 3: Synthesis of 4-methoxybenzyl
(1-(4-chlorophenyl)cyclopropyl)carbamate

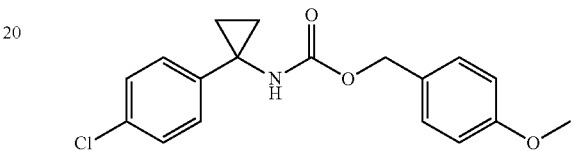

To a stirred solution of 1-(4-chlorophenyl)cyclopropane-1-carboxylic acid (step 2, 20.0 g, 102.04 mmol, 1.0 eq) in 1,2-dichloroethane (200 ml) under nitrogen atmosphere was added TEA (16.4 g, 163.26 mmol, 1.6 eq) followed by DPPA (44.7 g, 163.26 mmol, 1.6 eq). After 15 minutes stirring at room temperature, the solution was heated to reflux for about 1.5 hours. After which it was converted completely to the isocyanate by TLC, 4-methoxybenzyl alcohol (22.5 g, 163.26 mmol, 1.6 eq) was added and refluxing was continued for about 4 hours. TLC indicated starting material was consumed and the desired product was observed. The reaction mixture was evaporated under reduced pressure and the residue was purified by silicagel column chromatography by using 10% EtOAc:hexane as an eluent to obtain the desired product (25.0 g, 74% yield) as a white solid. ¹H NMR (300 MHz, CDCl₃): δ ppm 7.31-7.15 (m, 6H), 6.88 (d, J=8.1 Hz, 2H), 5.41 (s, 1H), 5.01 (s, 2H), 3.81 (s, 3H), 1.30-1.13 (m, 4H); ESI-MS: m/z 354.12 (M+Na)⁺.

Step 4: Synthesis of
1-(4-chlorophenyl)cyclopropan-1-amine

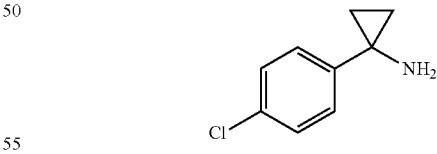

To a stirred solution of 4-methoxybenzyl (1-(4-chlorophenyl)cyclopropyl)carbamate (step 3, 25.0 g, 75.52 mmol, 1.0 eq) in DCM (200 ml) was added TFA (50 ml). The reaction mixture was stirred at room temperature for overnight. TLC indicated starting material was consumed and the desired product was observed. The reaction mixture was evaporated under reduced pressure, cooled to 0° C., pH adjusted to 8.0 with 5% NaHCO₃ solution and extracted with DCM (3×250 ml). The combined organic extracts were washed with water (250 ml), dried over sodium sulfate, filtered and evaporated under reduced pressure. The residue was purified by silicagel column chromatography by using 10% MeOH in DCM as an eluent to obtain the compound as a brown color liquid. To this liquid compound, methanol (100 ml) was added and stirred at room temperature for about 1 hour. The solid formed was removed by filtration and the filtrate was evaporated under reduced pressure to obtain the desired product (7.0 g, 55.5% yield) as colourless oil. $^1$H NMR (300 MHz, DMSO-$d_6$): δ ppm 7.35-7.26 (m, 4H), 2.33 (br.s., 2H), 1.0-0.94 (m, 2H), 0.92-0.86 (m, 2H); ESI-MS: m/z 168.01 (M+H)$^+$.

Intermediate-5: Synthesis of 2-(4-chlorophenyl)propan-2-amine

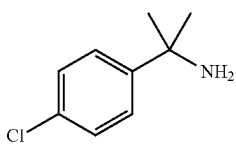

Step 1: Synthesis of 2-(4-chlorophenyl)-2-methylpropanenitrile

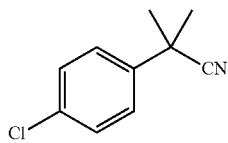

A suspension of 60% sodium hydride (22.8 g, 596.0 mmol, 3.0 eq) and THF (300 ml) was heated to 40° C. and a solution of 2-(4-chlorophenyl)acetonitrile (30.0 g, 198.6 mmol, 1.0 eq) in THF (100 ml) was added dropwise over about 30 minutes. The reaction mixture was stirred at 40° C. for about 30 minutes and a solution of methyl iodide (38.1 ml, 596.0 mmol, 3.0 eq) in THF (80 ml) was added dropwise over 30 minutes. The reaction mixture was stirred at 40° C. for about 1 hour. TLC indicated starting material was consumed and the desired product was observed. The reaction mixture was cooled to 0° C., quenched with ice water (250 ml) and extracted with ethyl acetate (3×400 ml). The combined organic extracts were washed with brine solution (400 ml), dried over sodium sulfate, filtered and evaporated under reduced pressure to obtain the desired product (30.0 g) as colourless oil. $^1$H NMR (300 MHz, CDCl$_3$): δ ppm 7.43-7.34 (m, 4H), 1.71 (s, 6H).

Step 2: Synthesis of 2-(4-chlorophenyl)-2-methylpropanoic acid

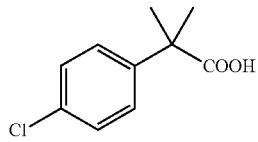

A stirred solution of 2-(4-chlorophenyl)-2-methylpropanenitrile (step 1, 30.0 g, 163.0 mmol, 1.0 eq), sodium hydroxide (19.5 g, 489.1 mmol, 3.0 eq), diethylene glycol (120 ml) and water (35 ml) was refluxed for about 18 hours. The reaction mixture was cooled to 0° C., acidified with 0.5N HCl (1200 ml) to pH 3-4. The generated crystals were collected by filtration and dried under vacuum to obtain the desired product (25.0 g, 77% yield) as a pale-brown color solid. $^1$H NMR (300 MHz, DMSO-$d_6$): δ ppm 12.44 (br.s., 1H), 7.41-7.34 (m, 4H), 1.46 (s, 6H).

Step 3: Synthesis of 4-methoxybenzyl (2-(4-chlorophenyl)propan-2-yl)carbamate

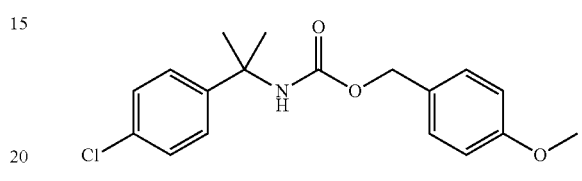

To a stirred solution of 2-(4-chlorophenyl)-2-methylpropanoic acid (step 2, 20.0 g, 101 mmol, 1.0 eq) in 1,2-dichloroethane (200 ml) was added TEA (16.32 g, 161.6 mmol, 1.6 eq) followed by DPPA (44.4 g, 161.6 mmol, 1.6 eq). After about 15 minutes stirring at room temperature, the solution was heated to reflux for about 1.5 hours. After which it was converted completely to the isocyanate by TLC, 4-methoxybenzyl alcohol (23.6 g, 171.7 mmol, 1.7 eq) was added and refluxing was continued for about 4 hours. TLC indicated starting material was consumed and the desired product was observed. The reaction mixture was evaporated under reduced pressure and the residue was purified by silicagel column chromatography by using 10% EtOAc:hexane as an eluent to obtain the desired product (22.0 g, 65.0% yield) as a white solid. $^1$H NMR (300 MHz, CDCl$_3$): δ ppm 7.37-7.20 (m, 6H), 6.95-6.82 (m, 2H), 4.93 (s, 2H), 3.81 (s, 3H), 1.62 (s, 6H).

Step 4: Synthesis of 2-(4-chlorophenyl)propan-2-amine

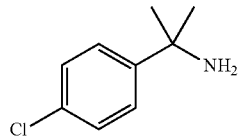

To a stirred solution of 4-methoxybenzyl (2-(4-chlorophenyl)propan-2-yl)carbamate (step 3, 22.0 g, 66.0 mmol, 1.0 eq) in DCM (200 ml) at 0° C. was added TFA (20 ml). The reaction mixture was allowed to stir at room temperature for overnight. TLC indicated starting material was consumed and the desired product was observed. The reaction mixture was evaporated under reduced pressure, cooled to 0° C., diluted with water (50 ml), pH adjusted to 10.0 with 2N NaOH solution and extracted with DCM (3×300 ml). The combined organic extracts were washed with water (300 ml), dried over sodium sulfate, filtered and evaporated under reduced pressure. The residue was treated with methanol (100 ml) and the solid formed was removed by filtration and the filtrate was evaporated under reduced pressure to obtain the desired product (10.04 g, 90% yield) as colourless oil. $^1$H NMR (300 MHz, CDCl$_3$): δ ppm 7.44 (d, J=8.7 Hz, 2H), 7.28 (d, J=8.4 Hz, 2H), 1.49 (s, 6H).

Intermediate-6: N$^1$-((1-(4-chlorophenyl)cyclopropyl)methyl)-N2,N2-dimethylethane-1,2-diamine

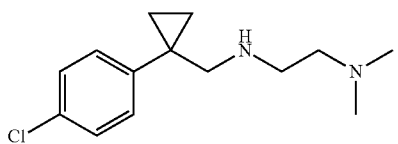 [SMILES: CN(C)CCNCC1(c2ccc(Cl)cc2)CC1]

Step 1: Synthesis of (1-(4-chlorophenyl)cyclopropyl)methanol

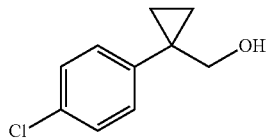 [SMILES: OCC1(c2ccc(Cl)cc2)CC1]

To a stirred solution of 1-(4-chlorophenyl)cyclopropane-1-carboxylic acid (Example 4-step 2, 10 g, 51.02 mmol, 1.0 eq) in THF (150 ml) at 0° C. under nitrogen was added borane dimethyl sulfide (51 ml, 102.04 mmol, 2.0 eq, 2.0M in THF). The reaction mixture was allowed to stir at room temperature for overnight. TLC indicated starting material was consumed and the desired product was observed. The reaction mixture was cooled to 0° C., quenched with saturated ammonium chloride solution (50 ml), diluted with water (100 ml) and extracted with EtOAc (3×200 ml). The combined organic extracts were washed with water (100 ml) and brine solution (50 ml). The organic layer was dried over Na$_2$SO$_4$, filtered and evaporated under reduced pressure to obtain the desired product (8.0 g) as colourless oil. $^1$H NMR (300 MHz, CDCl$_3$): δ ppm 7.36-7.27 (m, 4H), 3.65 (s, 2H), 0.86 (m, 4H).

Step 2: Synthesis of 1-(4-chlorophenyl)cyclopropane-1-carbaldehyde

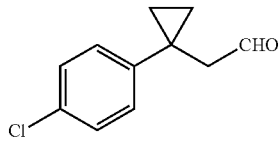 [SMILES: O=CCC1(c2ccc(Cl)cc2)CC1]

To a stirred solution of (1-(4-chlorophenyl)cyclopropyl)methanol (step 1, 5.0 g, 27.374 mmol, 1.0 eq) in DCM (300 ml) was added pyridinium chlorochromate (17.7 g, 82.122 mmol, 3.0 eq) and silicagel (17.7 g). The reaction mixture was stirred at room temperature for about 1 hour. TLC indicated starting material was consumed and the desired product was observed. The reaction mixture was quenched with water (50 ml), filtered and was washed with DCM (50 ml). The organic layer was separated and the aqueous layer was extracted with DCM (2×50 ml). The combined organic extracts were washed with saturated sodium bicarbonate solution (25 ml) and brine solution (20 ml). The organic layer was dried over Na$_2$SO$_4$, filtered and evaporated under reduced pressure. The residue was purified by silicagel column chromatography by using 10-20% ethyl acetate in hexane gradient. The fractions containing the expected product were combined and concentrated under reduced pressure to give the desired product (4.2 g, 85% yield) as colourless oil.

Step 3: Synthesis of N$^1$-((1-(4-chlorophenyl)cyclopropyl)methyl)-N$^2$,N$^2$-dimethylethane-1,2-diamine

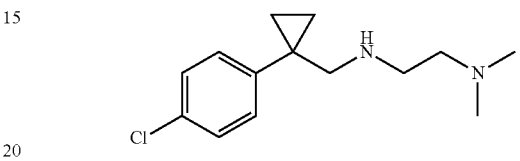

To a stirred solution of 1-(4-chlorophenyl)cyclopropane-1-carbaldehyde (step 2, 1.0 g, 7.113 mmol, 1.0 eq) in methanol (10 ml) at 0° C. was added N$^1$,N$^1$-dimethylethane-1,2-diamine (0.627 g, 7.113 mmol, 1.0 eq). The reaction mixture was stirred at room temperature for about 15 minutes, then NaBH$_4$ (0.269 g, 7.113 mmol, 1.0 eq) was added and stirred at room temperature for about 16 hours. TLC indicated starting material was consumed and the desired product was observed. The reaction mixture was evaporated under reduced pressure, cooled to 0° C., quenched with saturated ammonium chloride solution (10 ml) and extracted with ethyl acetate (3×50 ml). The combined organic extracts were washed with water (50 ml), dried over Na$_2$SO$_4$, filtered and evaporated under reduced pressure. The residue was purified by silicagel column chromatography by using 8% MeOH in DCM as an eluent to obtain the desired product (1.0 g, 55.8% yield) as a liquid. $^1$H NMR (300 MHz, CDCl$_3$): δ ppm 7.30-7.22 (m, 4H), 2.77 (s, 2H), 2.65 (t, J=6.6 Hz, 2H), 2.33 (t, J=6.3 Hz, 2H), 2.15 (s, 6H), 0.86-0.77 (m, 4H).

Intermediate-7: Synthesis of N-(4-chlorobenzyl)-2-(pyrrolidin-1-yl)ethan-1-amine

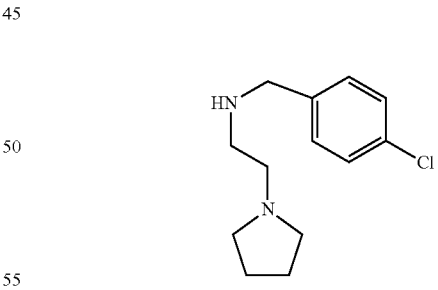

To a stirred solution of 2-(pyrrolidin-1-yl)ethan-1-amine (2.0 g, 17.51 mmol, 1.0 eq) in methanol (100 ml) at 0° C. was added 4-chlorobenzaldehyde (2.46 g, 17.51 mmol, 1.0 eq) and sodium borohydride (0.630 g, 17.51 mmol, 1.0 eq). The reaction mixture was allowed to stir at room temperature for overnight. TLC indicated starting material was consumed and the desired product was observed. The reaction mixture was cooled to 0° C. and quenched with saturated ammonium chloride solution. The organic phase was evaporated under reduced pressure and aqueous layer was extracted with DCM (3×200 ml). The combined organic extracts were dried over Na₂SO₄, filtered and evaporated under reduced pressure to obtain the desired product (3.57 g, 85.36% yield) as a colour less liquid. ¹H NMR (300 MHz, CDCl₃): δ ppm 7.31-7.23 (m, 4H), 3.77 (s, 2H), 2.71 (t, J=6.0 Hz, 2H), 2.61 (t, J=6.0 Hz, 2H), 2.52-2.45 (m, 4H), 1.79-1.73 (m, 4H); ESI-MS: m/z 239.17 (M+H)⁺.

Intermediate-8: 2-(5-phenyl-1H-imidazol-2-yl)propan-2-amine

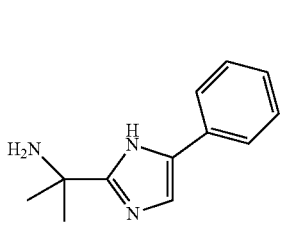

Step 1: 2-oxo-2-phenylethyl 2-((tert-butoxycarbonyl)amino)-2-methylpropanoate

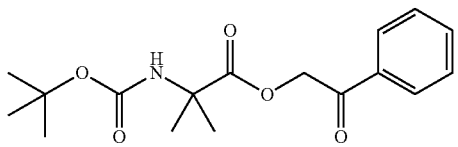 [SMILES: CC(C)(C)OC(=O)NC(C)(C)C(=O)OCC(=O)c1ccccc1]

To a stirred solution of 2-((tert-butoxycarbonyl)amino)-2-methylpropanoic acid (13.7 g, 67.48 mmol, 1.0 eq) in DCM (137 ml) at 0° C. was added DIPEA (37.31 ml, 289.22 mmol, 3.0 eq) followed by 2-bromo-1-phenylethan-1-one (16.11 g, 80.95 mmol, 1.2 eq). The reaction mixture was stirred at room temperature for overnight. TLC indicated starting material was consumed and the desired product was observed. The reaction mixture was washed with water and brine solution. The combined organic layer was dried over Na₂SO₄, filtered and evaporated under reduced pressure. The residue was purified by silicagel column chromatography to obtain the desired product (20 g, yield: 92.33%) as a yellow solid. ESI-MS: m/z 344.03 (M+Na)⁺.

Step 2: tert-butyl (2-(5-phenyl-1H-imidazol-2-yl)propan-2-yl)carbamate

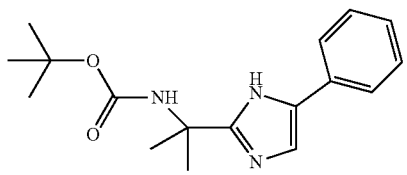 [SMILES: CC(C)(C)OC(=O)NC(C)(C)c1ncc(-c2ccccc2)[nH]1]

To a stirred solution of 2-oxo-2-phenylethyl 2-((tert-butoxycarbonyl)amino)-2-methylpropanoate (step 1, 20.0 g, 74.08 mmol, 1.0 eq) in toluene (200 ml) was added ammonium acetate (33.61 g, 436.0 mmol, 7.0 eq). The reaction mixture was heated at 90° C. for overnight. TLC indicated starting material was consumed and the desired product was observed. The reaction mixture was diluted with water and extracted with ethyl acetate. The combined organic layer was dried over sodium sulfate, filtered and evaporated under reduced pressure. The residue was purified by silicagel column chromatography to obtain the desired product (18.75 g) as a yellow solid.

Step 3: 2-(5-phenyl-1H-imidazol-2-yl)propan-2-amine

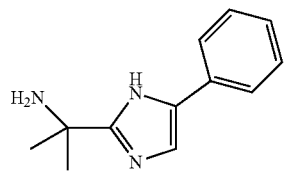

To a tert-butyl (2-(5-phenyl-1H-imidazol-2-yl)propan-2-yl)carbamate (step 2, 18.75 g, 62.29 mmol, 1.0 eq) in RB flask at 0° C. was added HCl in 1,4-dioxane (187 ml). The reaction mixture was stirred at room temperature for overnight. TLC indicated starting material was consumed and the desired product was observed. The reaction mixture was evaporated under reduced pressure, diluted with water, cooled to 0° C., pH adjusted to 8.0 with saturated sodium bicarbonate solution and extracted with DCM. The combined organic extracts were washed with water, dried over Na₂SO₄, filtered and evaporated under reduced pressure to obtain the desired product (9.0 g) as an off-white solid.

Intermediate-9: N-(4-chlorobenzyl)-2-(piperidin-1-yl)ethan-1-amine

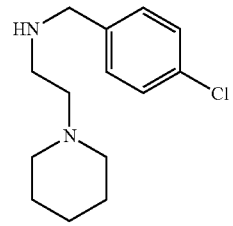 [SMILES: Clc1ccc(CNCCN2CCCCC2)cc1]

Step 1: Synthesis of tert-butyl (2-hydroxyethyl)carbamate

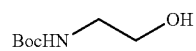

To a stirred solution of 2-aminoethan-1-ol (20.0 g, 327.0 mmol, 1.0 eq) in 1,4-dioxane (500 ml) was added saturated sodium bicarbonate solution (260 ml) and (Boc)₂O (100 ml, 491 mmol, 1.5 eq). The reaction mixture was stirred at room temperature for about 14 hours. TLC indicated starting material was consumed and the desired product was observed. The reaction mixture was evaporated under reduced pressure, diluted with water (300 ml) and extracted with DCM (2×300 ml). The combined organic extracts were dried over sodium sulfate, filtered and evaporated under reduced pressure to obtain the desired product (40 g, 76% yield) as an oil, which is used as such for next step without further purification. $^1$H NMR (300 MHz, CDCl$_3$): δ ppm 4.94 (br.s., 1H), 3.75-3.68 (m, 2H), 3.33-3.25 (m, 2H), 2.36 (s, 1H), 1.45 (s, 9H); ESI-MS: m/z 184.0 (M+Na)$^+$.

Step 2: Synthesis of 2-((tert-butoxycarbonyl)amino)ethyl 4-methylbenzenesulfonate

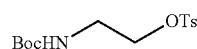

To a stirred solution of tert-butyl (2-hydroxyethyl)carbamate (step 1, 25.0 g, 155.0 mmol, 1.0 eq) in DCM (250 ml) was added triethyl amine (46.9 g, 465.0 mmol, 3.0 eq) and DMAP (1.89 g, 15.5 mmol, 0.1 eq). The reaction mixture was stirred at room temperature for 10 minutes and then para-Toluenesulfonylchloride (32.4 g, 170.0 mmol, 1.1 eq) was added at 0° C. The reaction mixture was stirred at room temperature for about 14 hours. TLC indicated starting material was consumed and the desired product was observed. The reaction mixture was diluted with water (250 ml) and extracted with DCM (2×250 ml). The combined organic extracts were dried over sodium sulfate, filtered and evaporated under reduced pressure. The residue was purified by silicagel column chromatography by using 20% EtOAc in hexane as an eluent to obtain the desired product (15.0 g, 30.7% yield) as a white solid. $^1$H NMR (300 MHz, CDCl$_3$): δ ppm 7.79 (d, J=8.1 Hz, 2H), 7.35 (d, J=8.1 Hz, 2H), 4.86 (s, 1H), 4.06 (t, J=4.8 Hz, 2H), 3.38 (t, J=5.1 Hz, 2H), 2.45 (s, 3H), 1.40 (s, 9H); ESI-MS: m/z 338.08 (M+Na)$^+$.

Step 3: Synthesis of tert-butyl (2-(piperidin-1-yl)ethyl)carbamate

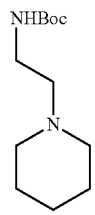

To a stirred solution of 2-((tert-butoxycarbonyl)amino) ethyl 4-methylbenzene sulfonate (step 2, 10.0 g, 31.7 mmol, 1.0 eq) in CH$_3$CN (250 ml) was added piperidine (3.2 g, 38.0 mmol, 1.2 eq) and potassium carbonate (17.11 g, 124.0 mmol, 4.0 eq). The reaction mixture was heated to reflux for about 14 hours. TLC indicated starting material was consumed and the desired product was observed. The reaction mixture was evaporated under reduced pressure, diluted with water (100 ml) and extracted with DCM (3×50 ml). The combined organic extracts were dried over sodium sulfate, filtered and evaporated under reduced pressure. The residue was purified by silicagel column chromatography by using 5% MeOH in DCM as an eluent to obtain the desired product (6.0 g, 85% yield) as a white solid. $^1$H NMR (300 MHz, CDCl$_3$): δ ppm 6.13 (br.s., 1H), 3.68-3.56 (m, 2H), 3.10-3.0 (m, 6H), 2.02 (m, 4H), 1.70-1.50 (m, 2H), 1.44 (s, 9H); ESI-MS: m/z 229.19 (M+H)$^+$.

Step 4: Synthesis of 2-(piperidin-1-yl)ethan-1-amine

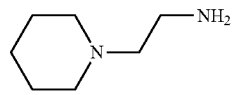

To a stirred solution of tert-butyl (2-(piperidin-1-yl)ethyl) carbamate (step 3, 6.0 g, 48.0 mmol, 1.0 eq) in DCM (60 ml) was added TFA (12 ml). The reaction mixture was stirred at room temperature for about 14 hours. TLC indicated starting material was consumed and the desired product was observed. The reaction mixture was evaporated under reduced pressure, cooled to 0° C., pH adjusted to 10.0 with 1N NaOH aqueous solution and extracted with DCM (3×100 ml). The combined organic extracts were washed with water (50 ml), dried over sodium sulfate, filtered and evaporated under reduced pressure to obtain the desired product (3.34 g, 98% yield) as a brown color liquid.

Step 5: Synthesis of N-(4-chlorobenzyl)-2-(piperidin-1-yl)ethan-1-amine

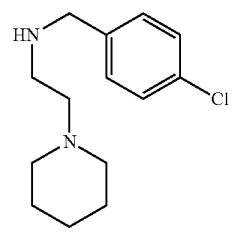 [SMILES: Clc1ccc(CNCCN2CCCCC2)cc1]

To a stirred solution of 2-(piperidin-1-yl)ethan-1-amine (step 4, 2.5 g, 19.0 mmol, 1.0 eq) in methanol (30 ml) was added 4-chlorobenzaldehyde (2.66 g, 19.0 mmol, 1.0 eq). The reaction mixture was stirred at room temperature for about 30 minutes, then sodium borohydride (0.718 g, 19.0 mmol, 1.0 eq) was added and stirred at same temperature for about 14 hours. TLC indicated starting material was consumed and the desired product was observed. The reaction mixture was evaporated under reduced pressure, cooled to 0° C., pH adjusted to 10.0 with 1N NaOH aqueous solution and extracted with DCM (3×25 ml). The combined organic extracts were dried over Na$_2$SO$_4$, filtered and evaporated under reduced pressure. The residue was purified by silicagel column chromatography by using 10% MeOH in DCM as an eluent to obtain the desired product (1.0 g, 20% yield) as a brown color liquid. $^1$H NMR (300 MHz, CDCl$_3$): δ ppm 7.30-7.23 (m, 5H), 3.76 (s, 2H), 2.66 (t, J=6.3 Hz, 2H), 2.43 (t, J=6.3 Hz, 2H), 2.38-2.28 (m, 4H), 1.58-1.50 (m, 4H), 1.47-1.42 (m, 2H).

Intermediate-10: 1-(2-(3-isopropyl-5-methyl-4H-1,2,4-triazol-4-yl)ethyl)piperazine

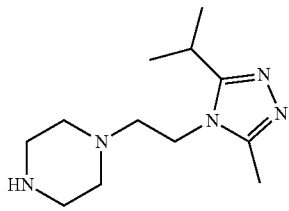 [SMILES: Cc1nnc(C(C)C)n1CCN1CCNCC1]

Step 1: Synthesis of
2-(4-benzylpiperazin-1-yl)ethan-1-ol

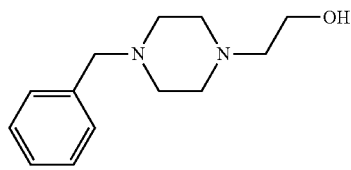 [SMILES: OCCN1CCN(Cc2ccccc2)CC1]

To a stirred solution of 2-(piperazin-1-yl)ethan-1-ol (5.0 g, 38.46 mmol, 1.0 eq) in CH$_3$CN (75 mL) at 0° C. was added triethylamine (15.98 mL, 115.38 mmol, 3.0 eq) and benzyl bromide (5.59 mL, 46.15 mmol, 1.2 eq). The reaction mixture was allowed to stir at room temperature for overnight. TLC indicated starting material was consumed and the desired product was observed. The reaction mixture was diluted with water and extracted with CH$_2$Cl$_2$. The combined organic layers were washed with water, brine solution, dried over Na$_2$SO$_4$, filtered and evaporated under reduced pressure to obtain the desired product (7.0 g, 82.0% yield). $^1$H NMR (300 MHz, CDCl$_3$): δ ppm 7.32-7.25 (m, 5H), 3.60 (t, J=5.1 Hz, 2H), 3.51 (s, 2H), 2.91 (br.s., 1H), 2.57-2.50 (m, 10H); ESI-MS: m/z 221.61 (M+H)$^+$.

Step 2: Synthesis of
2-(4-benzylpiperazin-1-yl)acetaldehyde

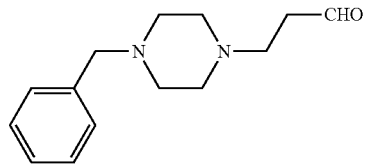 [SMILES: O=CCCN1CCN(Cc2ccccc2)CC1]

To a stirred solution of 2-(4-benzylpiperazin-1-yl)ethan-1-ol (step 1, 7.0 g, 31.81 mmol, 1.0 eq) in DCM (140 mL) at 0° C. was added Dess-Martin periodinane (20.23 g, 47.71 mmol, 1.5 eq). The reaction mixture was allowed to stir at room temperature for overnight. TLC indicated starting material was consumed and the desired product was observed. The reaction mixture was quenched with saturated NaHCO$_3$ solution and extracted with CH$_2$Cl$_2$. The combined organic layers were washed with water, brine solution, dried over Na$_2$SO$_4$, filtered and evaporated under reduced pressure. The crude residue (6.2 g, 89.0% yield) was used as such for next step without further purification. $^1$H NMR (300 MHz, CDCl$_3$): δ ppm 9.70 (s, 1H), 7.35-7.25 (m, 5H), 3.60-2.45 (m, 4H), 2.60-2.50 (m, 8H).

Step 3: Synthesis of
(Z)-2-(4-benzylpiperazin-1-yl)acetaldehyde oxime

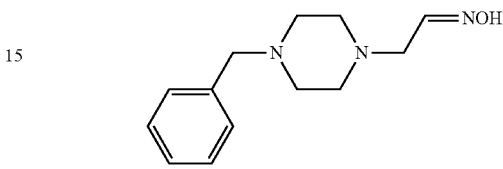

To a stirred solution of 2-(4-benzylpiperazin-1-yl)acetaldehyde (step 2, 6.2 g, 28.44 mmol, 1.0 eq) in EtOH (70 mL) was added Hydroxylamine hydrochloride (3.79 g, 48.34 mmol, 1.7 eq). The reaction mixture was heated to 50° C. then aqueous Na$_2$CO$_3$ solution (1.6 g in 1.5 ml water) was slowly added and refluxed for about 3 hours. TLC indicated starting material was consumed and the desired product was observed. The reaction mixture was diluted with water (200 ml) and extracted with CH$_2$Cl$_2$ (2×100 ml). The combined organic layers were washed with water, brine solution, dried over Na$_2$SO$_4$, filtered and evaporated under reduced pressure to obtain the desired product (6.0 g, 90.0% yield). $^1$H NMR (300 MHz, CDCl$_3$): δ ppm 7.32-7.29 (m, 5H), 6.86 (t, J=4.2 Hz, 1H), 3.49 (s, 2H), 3.34 (d, J=4.2 Hz, 1H), 3.13 (d, J=4.2 Hz, 1H), 2.57-2.42 (m, 8H).

Step 4: Synthesis of
2-(4-benzylpiperazin-1-yl)ethan-1-amine

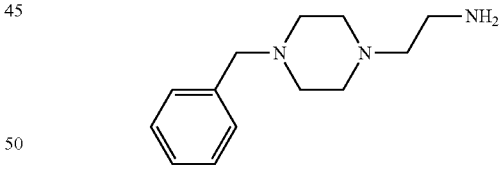

To a stirred solution of (Z)-2-(4-benzylpiperazin-1-yl)acetaldehyde oxime (step 3, 6.0 g, 25.75 mmol, 1.0 eq) in MeOH (31 mL) was added Raney Ni (1.4 g, 25.75 mmol, 1.0 eq) and Methanolic ammonia solution (63 ml). The reaction mixture was stirred under hydrogen atmosphere (balloon pressure) at room temperature for overnight. TLC indicated starting material was consumed and the desired product was observed. The reaction mixture was filtered through a pad of celite and washed with methanol (50 ml). The filtrate was evaporated under reduced pressure to obtain the desired product (4.5 g, 70.0% yield); 1H NMR (300 MHz, CDCl$_3$): δ ppm 7.31-7.22 (m, 5H), 3.43 (s, 2H) and 2.70-2.20 (m, 12H); ESI-MS: m/z 220.20 (M+H)$^+$.

Step 5: Synthesis of N-(2-(4-benzylpiperazin-1-yl)ethyl)isobutyramide

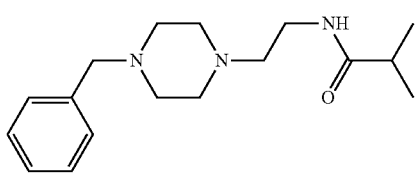 [SMILES: CC(C)C(=O)NCCN1CCN(Cc2ccccc2)CC1]

To a stirred solution of 2-(4-benzylpiperazin-1-yl)ethan-1-amine (step 4, 4.5 g, 20.54 mmol, 1.2 eq) in $CH_2Cl_2$ (58 ml) at 0° C. was added triethylamine (8.5 mL, 61.64 mmol, 3.0 eq) and Isobutyrylchloride (2.1 mL, 20.54 mmol, 1.0 eq). The reaction mixture was allowed to stir at room temperature for overnight. TLC indicated starting material was consumed and the desired product was observed. The reaction mixture was washed with water (2×50 ml), organic layer was dried over $Na_2SO_4$, filtered and evaporated under reduced pressure. The crude residue was purified by column chromatography by using 2% methanol:dichloromethane as an eluent to obtain the desired product (4.0 g. 67.0% yield). $^1H$ NMR (300 MHz, $CDCl_3$): δ ppm 7.66-7.59 (m, 1H), 7.34-7.23 (m, 5H), 3.43 (s, 2H), 3.16-3.08 (m, 3H), 2.36-2.29 (m, 10H), 1.05 (d, J=6.9 Hz, 3H), 0.96 (d, J=6.9 Hz, 3H); ESI-MS: m/z 312.13 $(M+Na)^+$.

Step 6: Synthesis of (E)-N'-acetyl-N-(2-(4-benzylpiperazin-1-yl)ethyl)isobutyro hydrazonamide

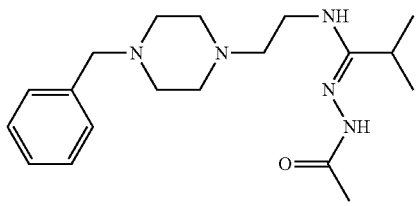 [SMILES: CC(=O)N/N=C(/NCCN1CCN(Cc2ccccc2)CC1)C(C)C]

To a stirred solution of $PCl_5$ (3.68 g, 18.0 mmol, 1.3 eq) in $CH_2Cl_2$ (60 mL) at 0° C. was slowly added N-(2-(4-benzylpiperazin-1-yl)ethyl)isobutyramide (step 5, 4.0 g, 13.84 mmol, 1.0 eq) dissolved in $CH_2Cl_2$ (30 ml). The reaction mixture was stirred at 0° C. for about 20 minutes and at room temperature for about 2 hours. A freshly prepared solution of acetic hydrazide [prepared by adding tert-amyl alcohol (15.7 ml) and $CH_3CN$ (40 ml) to acetic hydrazide (2.25 g, 30.44 mmol, 2.2 eq) and the total clear solution was concentrated to ¼ volume at 40° C. under vacuum] was added to the reaction mixture and stirred at room temperature for overnight. The reaction mixture was cooled to 0° C., basified with 10N aqueous NaOH solution to pH~9-10 and extracted with $CH_2Cl_2$ (2×100 ml). The combined organic layers were dried over $Na_2SO_4$, filtered and evaporated under reduced pressure to obtain the desired product (crude 4.5 g). $^1H$ NMR (300 MHz, $CDCl_3$): δ ppm 7.30 (m, 5H), 3.87 (t, J=6.9 Hz, 2H), 3.52 (s, 2H), 2.99-2.90 (m, 1H), 2.60-2.50 (m, 10H), 2.43 (s, 3H), 1.38 (d, J=6.9 Hz, 3H), 1.15 (d, J=6.9 Hz, 3H); ES-MS: m/z 346.10 $(M+H)^+$.

Step 7: Synthesis of 1-benzyl-4-(2-(3-isopropyl-5-methyl-4H-1,2,4-triazol-4-yl)ethyl) piperazine

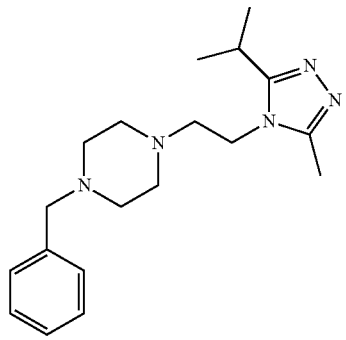 [SMILES: Cc1nnc(C(C)C)n1CCN1CCN(Cc2ccccc2)CC1]

To a stirred solution of (E)-$N^1$-acetyl-N-(2-(4-benzylpiperazin-1-yl)ethyl)isobutyro hydrazonamide (step 6, 4.5 g, 13.04 mmol, 1.0 eq) in tert-Amyl alcohol (20 ml) was added acetic acid (1.5 ml, 26.08 mmol, 2.0 eq). The reaction mixture was heated to reflux for about 3 hours. TLC indicated starting material was consumed and the desired product was observed. The reaction mixture was cooled to 0° C., basified with aqueous 2N NaOH to pH~10 and the two layers were separated. The aqueous layer was extracted with EtOAc (2×100 ml). The combined organic layers were dried over $Na_2SO_4$, filtered and evaporated under reduced pressure. The crude residue was purified by column chromatography by using 2% methanol:dichloromethane as an eluent to give the desired product (2.0 g, 47.0% yield). $^1H$ NMR (300 MHz, $CDCl_3$): δ ppm 7.31-7.27 (m, 5H), 3.87 (t, J=6.9 Hz, 2H), 3.51 (s, 2H), 2.99-2.90 (m, 1H), 2.60-2.40 (m, 10H), 2.43 (s, 3H), 1.38 (d, J=6.9 Hz, 6H); ESI-MS: m/z 328.19 $(M+H)^+$.

Step 8: Synthesis of 1-(2-(3-isopropyl-5-methyl-4H-1,2,4-triazol-4-yl)ethyl)piperazine

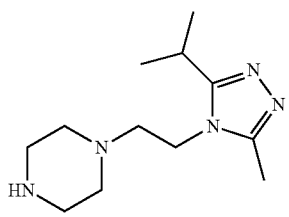 [SMILES: Cc1nnc(C(C)C)n1CCN1CCNCC1]

To a solution of 10% Pd/C (catalytic amount) in EtOAc (33 ml) was added a solution of 1-benzyl-4-(2-(3-isopropyl-5-methyl-4H-1,2,4-triazol-4-yl)ethyl)piperazine (step 7, 2.0 g, 6.11 mmol, 1.0 eq) in MeOH (50 ml) and para-Toluenesulfonic acid (1.16 g, 6.11 mmol, 1.0 eq). The reaction mixture was hydrogenated at 60 psi for overnight. TLC indicated starting material was consumed and the desired product was observed. The reaction mixture was filtered through celite and washed with EtOAc:methanol (1:4, 50 ml). The filtrate was evaporated under reduced pressure to obtain the desired product (1.1 g, 78.0% yield); ESI-MS: m/z 238.18 $(M+H)^+$.

Intermediate-11:
(S)-1-(pyrrolidin-2-ylmethyl)pyrrolidine
2,2,2-trifluoroacetate

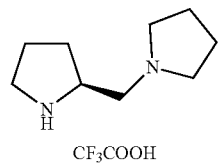

CF₃COOH

Step 1: tert-butyl
(S)-2-formylpyrrolidine-1-carboxylate

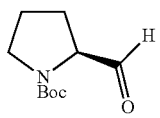 [SMILES: CC(C)(C)OC(=O)N1CCC[C@H]1C=O]

To a stirred solution of oxalyl chloride (2.50 ml, 28.68 mmol, 1.2 eq) in DCM (125 ml) at −78° C. was added DMSO (3.39 ml, 47.74 mmol, 2.0 eq). The reaction mixture was stirred at same temperature for 45 minutes, tert-butyl (S)-2-(hydroxymethyl)pyrrolidine-1-carboxylate (4.8 g, 23.88 mmol, 1.0 eq) in DCM (25 ml) was added and stirred at same temperature for 1 h. N,N-Diisopropylethylamine (16.64 ml, 95.52 mmol, 4.0 eq) was added and the reaction mixture was slowly warmed to room temperature and stirred for 30 minutes. Reaction mixture was neutralized with 0.5N HCl (20 ml), water (20 ml) was added and extracted with DCM (3×25 ml). The organic layer was dried over Na₂SO₄, filtered and evaporated under reduced pressure to obtain the titled compound (4.6 g) as a pale yellow color liquid. ¹H NMR (300 MHz, CDCl₃): δ ppm 9.46 (d, J=2.7 Hz, 1H), 4.22-4.03 (m, 1H), 3.59-3.40 (m, 2H), 2.22-1.80 (m, 4H), 1.43 (s, 9H); ESI-MS: m/z 222.06 (M+Na)⁺.

Step 2: tert-butyl (S)-2-(pyrrolidin-1-ylmethyl)pyrrolidine-1-carboxylate

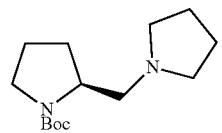 [SMILES: CC(C)(C)OC(=O)N1CCC[C@H]1CN1CCCC1]

To a stirred solution of tert-butyl (S)-2-formylpyrrolidine-1-carboxylate (step 1, 4.6 g, 23.08 mmol, 1.0 eq) in DCM (100 ml) was added pyrrolidine (1.806 g, 25.39 mmol, 1.1 eq), acetic acid (2.77 g, 46.17 mmol, 2.0 eq) and molecular sieves (5.0 g). The reaction mixture was stirred at room temperature for 10 minutes, then sodium triacetoxyborohydride (14.67 g, 69.26 mmol, 3.0 eq) was added and stirred at room temperature for 14 h. The reaction mixture was cooled to 0° C., pH adjusted to around 10 with 1N NaOH. The organic layer was separated and aqueous layer was extracted with DCM (2×30 ml). The combined organic layer was dried over Na₂SO₄, filtered and evaporated under reduced pressure. The residue was purified by silicagel column chromatography by using 10% methanol in dichloromethane as an eluent to obtain the titled compound (5.5 g, 90% yield over 2 steps) as a pale yellow color liquid. ¹H NMR (300 MHz, CDCl₃): δ ppm 4.02-3.85 (m, 1H), 3.40-3.12 (m, 3H), 3.10-2.60 (m, 5H), 2.0-1.80 (m, 8H), 1.46 (s, 9H); ESI-MS: m/z 255.15 (M+H)⁺.

Step 3: (S)-1-(pyrrolidin-2-ylmethyl)pyrrolidine 2,2,2-trifluoroacetate

CF₃COOH

To a stirred solution of tert-butyl (S)-2-(pyrrolidin-1-ylmethyl)pyrrolidine-1-carboxylate (step 2, 5.5 g, 21.62 mmol, 1.0 eq) in DCM (40 ml) was added trifluoroacetic acid (10 ml). The reaction mixture was stirred at room temperature for 14 h. After completion of the reaction monitored by TLC, the reaction mixture was evaporated under reduced pressure to obtain the titled compound (crude wt: 5.8 g) as a light brown solid.

EXAMPLES

Example 1: Preparation of (1R,3S)-3-((((3aR,5aR, 5bR,7aR,9S,11aR,11bR,13aS)-3a-(3-(4-chlorobenzyl)-3-(2-(dimethylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride

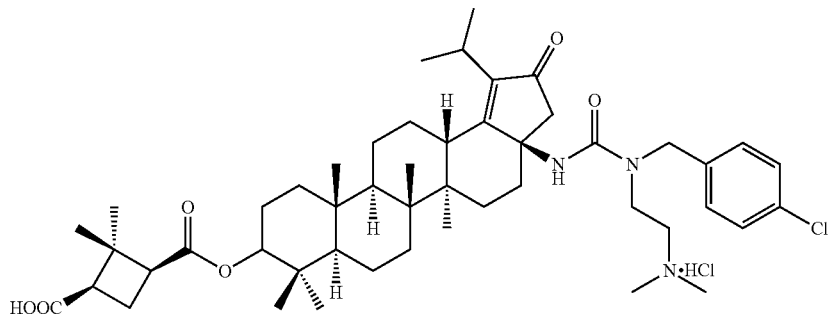

47

Step 1: Synthesis of (3aR,5aR,5bR,7aR,9S,11aR, 11bR,13aS)-3a-(3-(4-chlorobenzyl)-3-(2-(dimethyl- amino)ethyl)ureido)-1-isopropyl-5a,5b,8,8,11a-pen- tamethyl-2-oxo-3,3a,4,5,5a,5b,6,7,7a,8,9,10,11,11a, 11b,12,13,13a-octadecahydro-2H-cyclopenta[a] chrysen-9-yl acetate

48

Step 2: Synthesis of 1-(4-chlorobenzyl)-1-(2-(dim- ethylamino)ethyl)-3-((3aR,5aR,5bR,7aR,9S,11aR, 11bR,13aS)-9-hydroxy-1-isopropyl-5a, 5b,8,8,11a- pentamethyl-2-oxo-2,3,4,5,5a,5b,6,7,7a,8,9,10,11, 11a,11b,12,13,13a-octadecahydro-3aH-cyclopenta[a] chrysen-3a-yl)urea

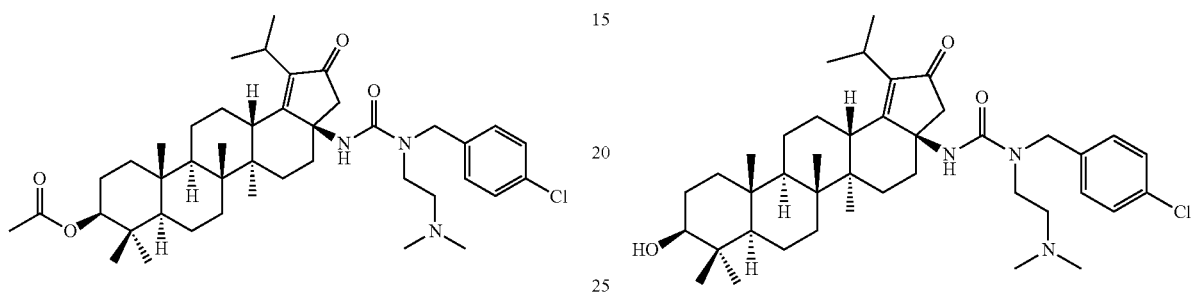

To a stirred solution of (3aR,5aR,5bR,7aR,9S,11aR,11bR, 13aS)-3a-isocyanato-1-isopropyl-5a,5b,8,8,11a-pentam- ethyl-2-oxo-3,3a,4,5,5a,5b,6,7,7a,8,9,10,11,11a,11b,12,13, 13a-octadecahydro-2H-cyclopenta[a]chrysen-9-yl acetate (Intermediate-1 11.0 g, 21.61 mmol, 1.0 eq) in THF (160 ml) at 0° C. was added DIPEA (11.15 g, 86.44 mmol, 4.0 eq) and N-(4-chlorobenzyl)-$N^2,N^2$-dimethylethane-1,2-diamine (In- termediate-3 9.16 g, 43.22 mmol, 2.0 eq). The reaction mixture was allowed to stir at room temperature for about 16 hours. TLC indicated starting material was consumed and the desired product was observed. The reaction mixture was evaporated under reduced pressure, diluted with water (100 ml) and extracted with DCM (3×200 ml). The combined organic extracts were washed with water (100 ml), dried over sodium sulfate, filtered and evaporated under reduced pressure. The residue was purified by silicagel column chromatography by using 5% MeOH:DCM as an eluent to obtain the desired product (11.0 g, 70% yield) as a white solid. $^1$H NMR (300 MHz, CDCl$_3$): δ ppm 8.28 (s, 1H), 7.28 (d, J=8.1 Hz, 2H), 7.17 (d, J=8.1 Hz, 2H), 4.53-4.34 (m, 3H), 3.35-3.25 (m, 1H), 3.20-2.98 (m, 3H), 2.69 (d, J=18.6 Hz, 1H), 2.63-2.56 (m, 1H), 2.40 (d, J=18.9 Hz, 1H), 2.33-2.27 (m, 2H), 2.17 (s, 6H), 2.05 (s, 3H), 2.02-1.57 (m, 8H), 1.51-1.20 (m, 13H), 1.13 (s, 3H), 1.09-1.01 (m, 1H), 0.95 (s, 3H), 0.92 (s, 3H), 0.86 (s, 3H), 0.85 (s, 3H), 0.81 (m, 1H); ESI-MS: m/z 744.54 (M+Na)$^+$.

To a stirred solution of (3aR,5aR,5bR,7aR,9S,11aR,11bR, 13aS)-3a-(3-(4-chloro benzyl)-3-(2-(dimethylamino)ethyl) ureido)-1-isopropyl-5a,5b,8,8,11a-pentamethyl-2-oxo-3,3a, 4,5,5a,5b,6,7,7a,8,9,10,11,11a,11b,12,13,13a- octadecahydro-2H-cyclopenta[a]chrysen-9-yl acetate (step 1, 11.0 g, 15.22 mmol, 1.0 eq) in THF (60 ml), MeOH (120 ml) and water (30 ml) at 0° C. was added NaOH (9.135 g, 228.38 mmol, 15.0 eq). The reaction mixture was allowed to stir at room temperature for about 6 hours. TLC indicated starting material was consumed and the desired product was observed. The reaction mixture was evaporated under reduced pressure, diluted with water (100 ml) and extracted with DCM (3×200 ml). The combined organic extracts were washed with water (100 ml), dried over sodium sulfate, filtered and evaporated under reduced pressure. The residue was purified by silicagel column chromatography by using 5% MeOH:DCM as an eluent to obtain the desired product (9.53 g, 92% yield) as a white solid. $^1$H NMR (300 MHz, CDCl$_3$): δ ppm 8.29 (s, 1H), 7.28 (d, J=8.4 Hz, 2H), 7.17 (d, J=8.4 Hz, 2H), 4.50, 4.38 (ABq, J$_{AB}$=15.5 Hz, 2H), 3.36- 2.97 (m, 5H), 2.70 (d, J=18.9 Hz, 1H), 2.64-2.54 (m, 1H), 2.40 (d, J=18.6 Hz, 1H), 2.33-2.27 (m, 2H), 2.17 (s, 6H), 2.05-1.85 (m, 3H), 1.80-1.72 (m, 1H), 1.71-1.64 (m, 2H), 1.56-1.28 (m, 8H), 1.27-1.18 (m, 7H), 1.13 (s, 3H), 1.08- 1.02 (m, 1H), 0.98 (s, 3H), 0.95 (s, 3H), 0.90 (s, 3H), 0.77 (s, 3H), 0.75-0.70 (m, 1H); ESI-MS: m/z 702.5 (M+Na)$^+$.

Step 3: Synthesis of 1-benzyl 3-(((3aR,5aR,5bR,7aR,9S,11aR,11bR,13aS)-3a-(3-(4-chloro benzyl)-3-(2-(dimethylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

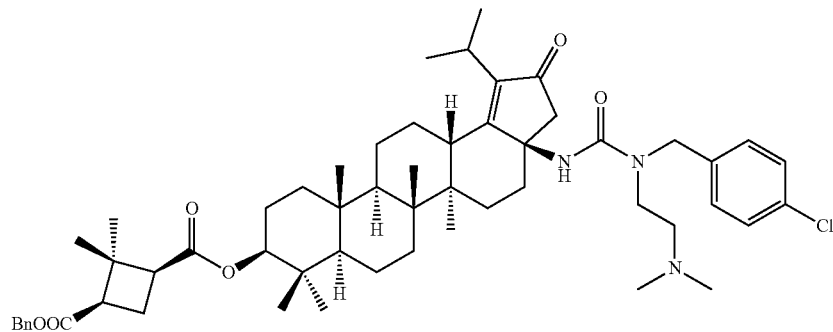

To a stirred solution of 1-(4-chlorobenzyl)-1-(2-(dimethylamino)ethyl)-3-((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysen-3a-yl) urea (step 2, 4.0 g, 5.891 mmol, 1.0 eq) and (1S,3R)-3-((benzyloxy)carbonyl)-2,2-dimethyl cyclobutane-1-carboxylicacid (prepared as described in WO/2011/007230 A2, 2.3 g, 8.836 mmol, 1.5 eq) in DCM (150 ml) at 0° C. was added triethyl amine (2.97 g, 29.455 mmol, 5.0 eq), DMAP (0.359 g, 2.945 mmol, 0.5 eq) and 2,4,6-trichlorobenzoyl chloride (2.874 g, 11.782 mmol, 2.0 eq). The reaction mixture was flushed with nitrogen and allowed to stir at room temperature for overnight. TLC indicated starting material was consumed and the desired product was observed. The reaction mixture was diluted with water (200 ml) and extracted with DCM (3×200 ml). The combined organic extracts were dried over $Na_2SO_4$, filtered and evaporated under reduced pressure. The residue was purified by silicagel column chromatography by using 4% MeOH:DCM as an eluent to obtain the desired product (4.5 g, 83.3% yield) as a white solid.

Step 4: Synthesis of (1R,3S)-3-((((3aR,5aR,5bR,7aR,9S,11aR,11bR,13aS)-3a-(3-(4-chloro benzyl)-3-(2-(dimethylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

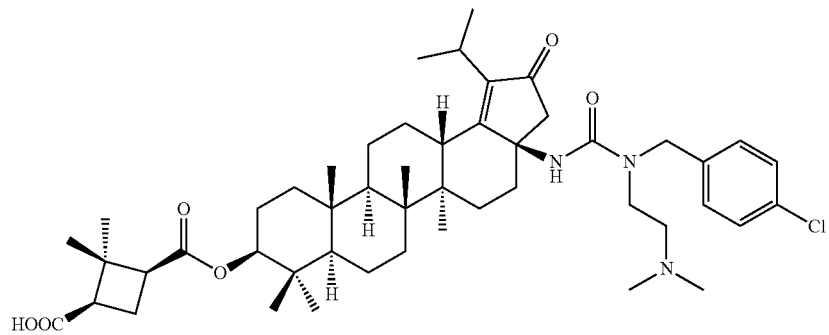

To a stirred solution of 1-benzyl 3-((3aR,5aR,5bR,7aR, 9S,11aR,11bR,13aS)-3a-(3-(4-chlorobenzyl)-3-(2-(dimethylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 3, 4.5 g, 4.87 mmol, 1.0 eq) in MeOH (60 ml), THF (45 ml) and water (45 ml) was added KOH (1.911 g, 34.12 mmol, 7.0 eq). The reaction mixture was stirred at room temperature for overnight. TLC indicated starting material was consumed and the desired product was observed. The reaction mixture was evaporated under reduced pressure, diluted with water (10 ml) and pH adjusted to 6.0 with 1N HCl and extracted with DCM (3×200 ml). The combined organic extracts were dried over sodium sulfate, filtered and evaporated under reduced pressure. The residue was purified by silicagel column chromatography by using 8% MeOH:DCM as an eluent to obtain the desired product (3.5 g, 87.5% yield) as a white solid. $^1$H NMR (300 MHz, DMSO-$d_6$): δ ppm 12.27 (br.s., 1H), 7.45 (d, J=8.1 Hz, 2H), 7.12 (d, J=7.2 Hz, 2H), 4.54 (m, 2H), 4.38-4.31 (m, 1H), 3.10-2.95 (m, 1H), 2.85-2.72 (m, 5H), 2.40-2.22 (m, 6H), 2.13 (s, 6H), 1.95-1.52 (m, 13H), 1.50-1.22 (m, 12H), 1.20-0.9 (m, 8H), 0.90-0.70 (m, 13H); ESI-MS: m/z 834.56 (M+H)$^+$.

Step 5: Synthesis of (1R,3S)-3-((((3aR,5aR,5bR,7aR,9S,11aR,11bR,13aS)-3a-(3-(4-chloro benzyl)-3-(2-(dimethylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride To a stirred solution of (1R,3S)-3-((((3aR,5aR,5bR,7aR, 9S,11aR,11bR,13aS)-3a-(3-(4-chlorobenzyl)-3-(2-(dimethylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (step 4, 2.0 g, 2.40 mmol, 1.0 eq) in 1,4-dioxane (10 ml) at 0° C. was added 1.5N HCl/1,4-dioxane (40 ml). After stirring at room temperature for overnight, the reaction mixture was evaporated to dryness. The residue was triturated with n-hexane and the solids that formed were collected by filtration were taken into MTBE (20 ml) and heated to reflux for about 20 minutes. The mixture was cooled to 0° C., filtered and dried under vacuum to obtain the desired product (1.6 g, 77% yield) as a white solid. $^1$H NMR (300 MHz, DMSO-$d_6$): δ ppm 12.15 (br.s., 1H), 10.20 (br.s., 1H), 7.43 (d, J=8.4 Hz, 2H), 7.21 (d, J=8.4 Hz, 2H), 6.33 (s, 1H), 4.68, 4.52 (ABq, J$_{AB}$=17.4 Hz, 2H), 4.38-4.31 (m, 1H), 3.78-3.65 (m, 1H), 3.55-3.40 (m, 2H), 3.21-3.13 (m, 3H), 2.83-2.60 (m, 4H), 2.75 (s, 6H), 2.37-2.25 (m, 1H), 2.10 (d, J=18.3 Hz, 1H), 1.93-1.80 (m, 2H), 1.80-1.38 (m, 7H), 1.38-1.20 (m, 8H), 1.17-0.97 (m, 10H), 0.91 (s, 3H), 0.86 (s, 3H), 0.84 (s, 3H), 0.80 (s, 6H), 0.64 (s, 3H); ESI-MS: m/z 834.63 (M-HCl+H)$^+$; HPLC: 93.62%.

Example 2: Preparation of (1R,3S)-3-(((((3aR,5aR,5bR,7aR,9S,11aR,11bR,13aS)-3a-((S)-2-(1-(2-(dimethylamino)ethyl)-5-phenyl-1H-imidazol-2-yl)pyrrolidine-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

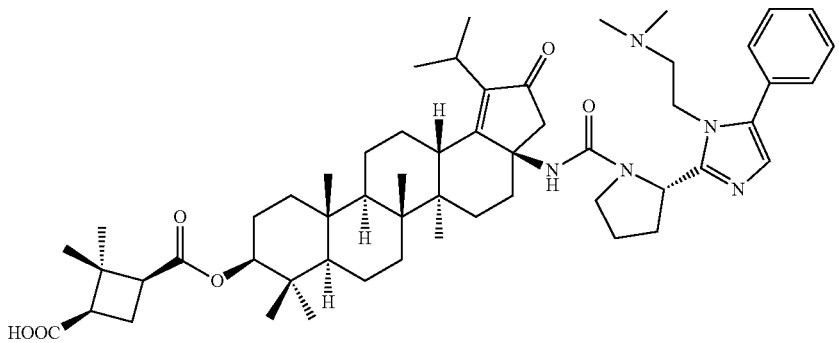

Step 1: Synthesis of (3aR,5aR,5bR,7aR,9S,11aR,11bR,13aS)-3a-((S)-2-(1-(2-(dimethyl amino)ethyl)-5-phenyl-1H-imidazol-2-yl)pyrrolidine-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

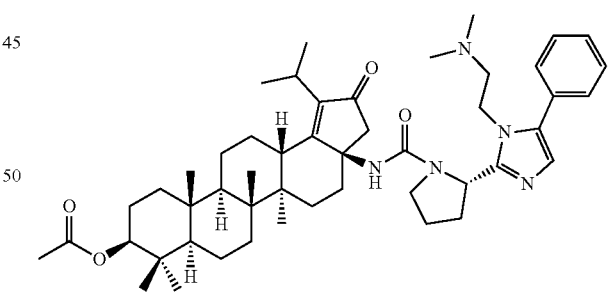

To a stirred solution of (3aR,5aR,5bR,7aR,9S,11aR,11bR,13aS)-3a-isocyanato-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Intermediate-1, 2.0 g, 3.929 mmol, 1.0 eq) in THF (20 ml) was added DIPEA (2.8 ml, 15.717 mmol, 4.0 eq) and (S)—N,N-dimethyl-2-(5-phenyl-2-(pyrrolidin-2-yl)-1H-imidazol-1-yl)ethan-1-amine (prepared as described in: WO 2016/001820 A1, 2.2 g, 7.85 mmol, 2.0 eq). The reaction mixture was stirred at room temperature for overnight. TLC indicated starting material was consumed and the desired product was observed. The reaction mixture was diluted with ethyl acetate (200 ml) and washed with water (2×100 ml). The organic layer was dried over sodium sulfate, filtered and evaporated under reduced pressure. The residue was purified by silicagel column chromatography by using 0-3% MeOH in DCM gradient to obtain the desired product (2.0 g, 64% yield) as a white solid; ESI-MS: m/z 816.6 (M+Na)+.

Step 2: Synthesis of (S)-2-(1-(2-(dimethylamino) ethyl)-5-phenyl-1H-imidazol-2-yl)-N-((3aR,5aR, 5bR,7aR,9S,11aR,11bR,13aS)-9-hydroxy-1-isopropyl-5a, 5b,8,8,11a-pentamethyl-2-oxo-2,3,4,5,5a,5b, 6,7,7a,8,9,10,11,11a,11b,12,13,13a-octadecahydro-3aH-cyclopenta[a]chrysen-3a-yl)pyrrolidine-1-carboxamide under reduced pressure. The residue was purified by silicagel column chromatography by using 0-4% MeOH in DCM gradient to obtain the desired product (1.8 g, 95% yield) as a white solid. 1H NMR (300 MHz, DMSO-$d_6$): δ ppm 7.68 (d, J=7.2 Hz, 2H), 7.52 (s, 1H), 7.35-7.25 (m, 2H), 7.20-7.10 (m, 1H), 5.82 (s, 1H), 5.10-5.0 (m, 1H), 4.20-4.03 (m, 2H), 3.70-3.60 (m, 1H), 3.50-3.38 (m, 1H), 3.10-2.92 (m, 2H), 2.88-2.78 (m, 1H), 2.70-2.60 (m, 2H), 2.43-2.40 (m, 1H), 2.30-2.10 (m, 9H), 2.09-1.75 (m, 6H), 1.70-1.55 (m, 2H), 1.55-1.40 (m, 3H), 1.40-1.20 (m, 6H), 1.20-1.10 (m, 7H), 1.0-0.90 (m, 4H), 0.87 (s, 3H), 0.83 (s, 3H), 0.75 (s, 3H), 0.65 (m, 4H); ESI-MS: m/z 774.41 (M+Na)+.

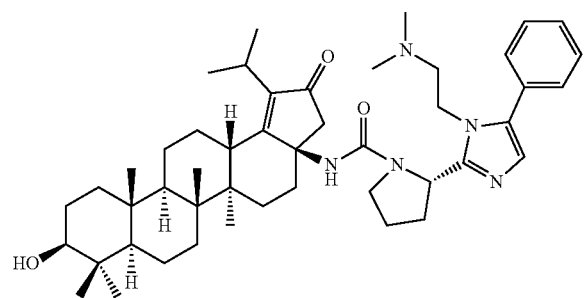

Step 3: Synthesis of 1-benzyl 3-((3aR,5aR,5bR, 7aR,9S,11aR,11bR,13aS)-3a-((S)-2-(1-(2-(di methylamino)ethyl)-5-phenyl-1H-imidazol-2-yl)pyrrolidine-1-carboxamido)-1-isopropyl-5a,5b,8,8,11a-pentamethyl-2-oxo-3,3a,4,5,5a,5b,6,7,7a,8,9,10,11a, 11b,12,13,13a-octadeca hydro-2H-cyclopenta[a] chrysen-9-yl) (1R,3S)-2,2-dimethylcyclobutane-1,3-dicarboxylate

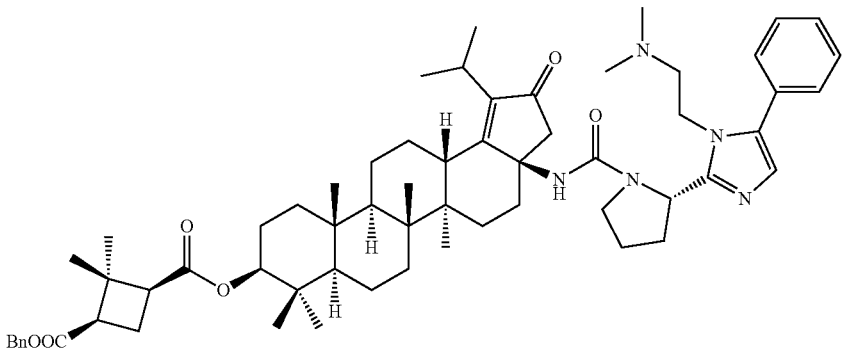

To a stirred solution of (3aR,5aR,5bR,7aR,9S,11aR,11bR, 13aS)-3a-((S)-2-(1-(2-(dimethylamino)ethyl)-5-phenyl-1H-imidazol-2-yl)pyrrolidine-1-carboxamido)-1-isopropyl-5a, 5b,8,8,11a-pentamethyl-2-oxo-3,3a,4,5,5a,5b,6,7,7a,8,9,10, 11,11a,11b,12,13,13a-octadeca hydro-2H-cyclopenta[a] chrysen-9-yl acetate (step 1, 2.0 g, 2.52 mmol, 1.0 eq) in MeOH (88 ml), THF (44 ml) and water (22 ml) at 0° C. was added NaOH (1.0 g, 25.2 mmol, 10.0 eq). The reaction mixture was allowed to stir at room temperature for overnight. TLC indicated starting material was consumed and the desired product was observed. The reaction mixture was evaporated under reduced pressure, diluted with DCM (100 ml) and was washed with water (2×100 ml). The organic layer was dried over sodium sulfate, filtered and evaporated To a stirred solution of (S)-2-(1-(2-(dimethylamino) ethyl)-5-phenyl-1H-imidazol-2-yl)-N-((3aR,5aR,5bR,7aR, 9S,11aR,11bR,13aS)-9-hydroxy-1-isopropyl-5a,5b,8,8,11a-penta methyl-2-oxo-2,3,4,5,5a,5b,6,7,7a,8,9,10,11,11a,11b, 12,13,13a-octadecahydro-3aH-cyclo penta[a]chrysen-3a-yl) pyrrolidine-1-carboxamide (step 2, 1.8 g, 2.4 mmol, 1.0 eq) and (1S,3R)-3-((benzyloxy)carbonyl)-2,2-dimethylcyclobutane-1-carboxylic acid (prepared as described in WO/2011/007230 A2, 0.94 g, 3.6 mmol, 1.5 eq) in DCM (20 ml) at 0° C. were added triethylamine (1.7 ml, 12.0 mmol, 5.0 eq), DMAP (0.146 g, 1.2 mmol, 0.5 eq) and 2,4,6-trichlorobenzoyl chloride (0.58 ml, 3.6 mmol, 1.5 eq). The reaction mixture was allowed to stir at room temperature for overnight. TLC indicated starting material was consumed and the desired product was observed. The reaction mixture was diluted with DCM (100 ml) and was washed with water (2×100 ml). The organic layer was dried over $Na_2SO_4$, filtered and evaporated under reduced pressure. The residue was purified by silicagel column chromatography by using 0-3% MeOH in DCM gradient to obtain the desired product (2.0 g, 84% yield) as a white solid. $^1$H NMR (300 MHz, CDCl$_3$): δ ppm 7.40-7.20 (m, 11H), 5.20-5.08 (m, 2H), 5.08-5.0 (m, 1H), 4.50-4.40 (m, 1H), 4.18-4.05 (m, 2H), 3.92-3.78 (m, 1H), 3.55-3.45 (m, 1H), 3.02-2.40 (m, 11H), 2.34 (s, 6H), 2.18-2.05 (m, 4H), 1.80-1.40 (m, 12H), 1.40-1.30 (m, 6H), 1.30-1.20 (m, 6H), 1.20-1.10 (m, 3H), 1.10-0.92 (m, 7H), 0.91 (s, 3H), 0.88-0.80 (m, 6H), 0.80-0.72 (m, 1H).

Step 4: Synthesis of (1R,3S)-3-(((((3aR,5aR,5bR,7aR,9S,11aR,11bR,13aS)-3a-((S)-2-(1-(2-(di methylamino)ethyl)-5-phenyl-1H-imidazol-2-yl)pyrrolidine-1-carboxamido)-1-isopropyl-5a,5b,8,8,11a-pentamethyl-2-oxo-3,3a,4,5,5a,5b,6,7,7a,8,9,10,11,11a,11b,12,13,13a-octadeca hydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR,9S,11aR,11bR,13aS)-3a-((S)-2-(1-(2-(dimethylamino) ethyl)-5-phenyl-1H-imidazol-2-yl)pyrrolidine-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 3, 2.0 g, 2.0 mmol, 1.0 eq) in MeOH (38 ml) and THF (38 ml) was added aqueous 2.5N KOH solution (6.4 ml, 15.09 mmol, 7.5 eq). The reaction mixture was stirred at room temperature for overnight. TLC indicated starting material was consumed and the desired product was observed. The reaction mixture was evaporated under reduced pressure, cooled to 0° C., acidified with 1N HCl to pH-6 and was extracted with DCM (100 ml). The organic layer was washed with water (2×100 ml), dried over sodium sulfate, filtered and evaporated under reduced pressure. The residue was purified by silicagel column chromatography by using 0-7% MeOH in DCM gradient. The fractions containing the expected product were combined and concentrated under reduced pressure to give the desired product (50 mg, 3% yield) as an off-white solid. $^1$H NMR (300 MHz, DMSO-d$_6$): δ ppm 12.17 (br.s., 1H), 7.68 (d, J=7.2 Hz, 2H), 7.53 (s, 1H), 7.35-7.27 (m, 2H), 7.19-7.14 (m, 1H), 5.86 (m, 1H), 5.09 (m, 1H), 4.49-4.30 (m, 1H), 4.25-4.08 (m, 2H), 3.70-3.60 (m, 1H), 3.12-3.0 (m, 3H), 2.87-2.70 (m, 3H), 2.70-2.10 (m, 10H), 2.0-1.80 (m, 8H), 1.75-1.42 (m, 6H), 1.40-1.30 (m, 3H), 1.30-1.18 (m, 7H), 1.17-1.03 (m, 9H), 1.01-0.89 (m, 4H), 0.89-0.75 (m, 13H); ESI-MS: m/z 906.68 (M+H)$^+$; HPLC: 92.04%.

Example 3: Preparation of (1R,3S)-3-(((((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

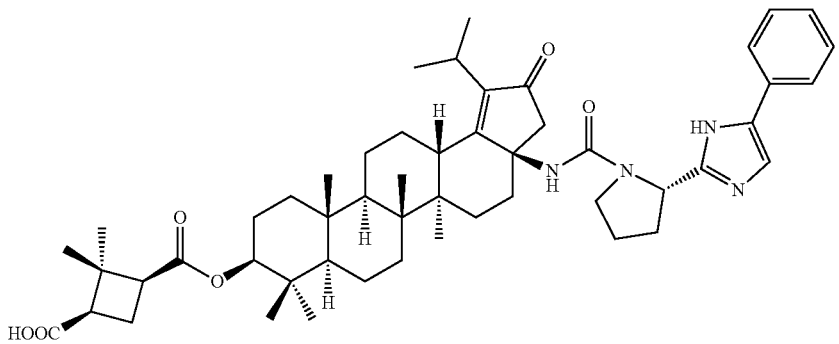

Step 1: Synthesis of (3aR,5aR,5bR,7aR,9S,11aR,11bR,13aS)-1-isopropyl-5a,5b,8,8,11a-penta methyl-2-oxo-3a-((S)-2-(5-phenyl-1H-imidazol-2-yl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl acetate

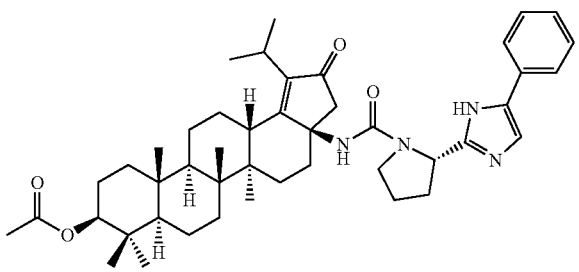

To a stirred solution of (3aR,5aR,5bR,7aR,9S,11aR,11bR,13aS)-3a-isocyanato-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Intermediate-1, 2.26 g, 4.44 mmol, 1.0 eq) in THF (22 ml) was added DIPEA (2.29 g, 17.76 mmol, 4.0 eq) and (S)-5-phenyl-2-(pyrrolidin-2-yl)-1H-imidazole (prepared as described in WO 2014/105926 A1, 1.89 g, 8.88 mmol, 2.0 eq). The reaction mixture was stirred at room temperature for overnight. TLC indicated starting material was consumed and the desired product was observed. The reaction mixture was evaporated under reduced pressure, diluted with water and extracted with DCM (2×100 ml). The combined organic extracts were washed with brine solution, dried over sodium sulfate, filtered and evaporated under reduced pressure. The residue was purified by silicagel column chromatography by using 0-5% methanol in DCM eluent to obtain the desired product (2.5 g, 78% yield) as a brown color solid. $^1$H NMR (300 MHz, CDCl$_3$): δ ppm 10.44 (br.s., 1H), 7.78-7.75 (m, 2H), 7.40-7.30 (m, 2H), 7.30-7.18 (m, 2H), 5.10-5.02 (m, 1H), 4.53-4.45 (m, 1H), 3.45-3.35 (m, 2H), 3.20-3.08 (m, 1H), 3.0-2.72 (m, 3H), 2.38-2.18 (m, 4H), 2.15-2.0 (m, 1H), 2.05 (s, 3H), 2.0-1.48 (m, 10H), 1.42-1.20 (m, 11H), 1.17-1.0 (m, 1H), 1.05 (s, 3H), 0.97-0.89 (m, 6H), 0.87-0.78 (m, 7H); ESI-MS: m/z 723.72 (M+H)$^+$.

Step 2: Synthesis of (S)—N-((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octadeca hydro-3aH-cyclopenta[a]chrysen-3a-yl)-2-(5-phenyl-1H-imidazol-2-yl)pyrrolidine-1-carboxamide

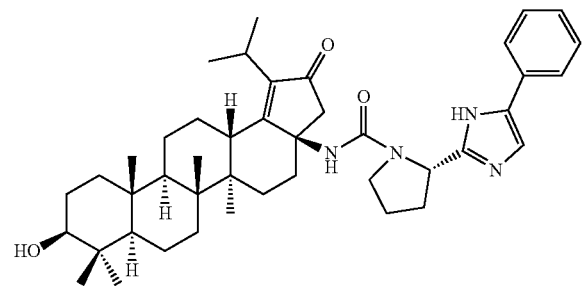

To a stirred solution of (3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl acetate (step 1, 2.5 g, 3.462 mmol, 1.0 eq) in MeOH (66.3 ml), THF (33.8 ml) and water (16.9 ml) at 0° C. was added NaOH (1.385 g, 34.62 mmol, 10.0 eq). The reaction mixture was allowed to stir at room temperature for overnight. TLC indicated starting material was consumed and the desired product was observed. The reaction mixture was evaporated under reduced pressure, diluted with DCM, washed with water and brine solution. The organic layer was dried over sodium sulfate, filtered and evaporated under reduced pressure. The residue was purified by silicagel column chromatography by using 0-5% MeOH in DCM gradient to obtain the desired product (1.3 g, 56.5% yield) as a white solid. $^1$H NMR (300 MHz, CDCl$_3$): δ ppm 10.36 (br.s., 1H), 7.80-7.68 (m, 2H), 7.42-7.30 (m, 2H), 7.30-7.12 (m, 2H), 5.10-5.0 (m, 1H), 3.47-3.35 (m, 2H), 3.25-3.08 (m, 2H), 2.90-2.75 (m, 3H), 2.37-2.20 (m, 3H), 2.20-2.02 (m, 2H), 2.0-1.85 (m, 3H), 1.85-1.75 (m, 3H), 1.60-1.48 (m, 3H), 1.48-1.12 (m, 12H), 1.05 (s, 3H), 1.0-0.85 (m, 1H), 1.0 (s, 3H), 0.97 (s, 3H), 0.87 (s, 3H), 0.76 (s, 3H), 0.72-0.67 (m, 1H); ESI-MS: m/z 703.5 (M+Na)$^+$.

Step 3: Synthesis of 1-benzyl 3-((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

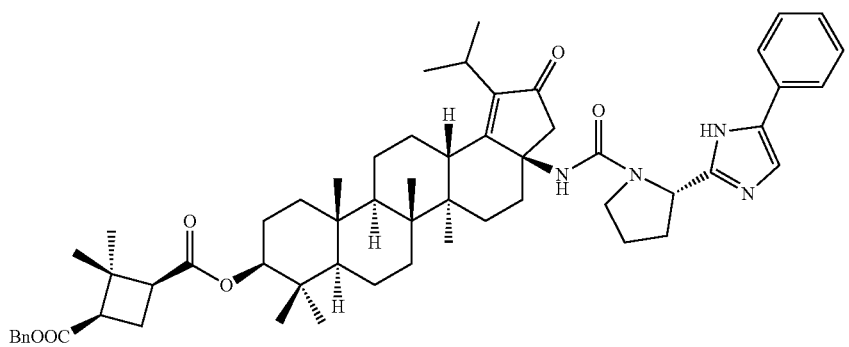

To a stirred solution of (S)—N-((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysen-3a-yl)-2-(5-phenyl-1H-imidazol-2-yl)pyrrolidine-1-carboxamide (step 2, 1.3 g, 1.911 mmol, 1.0 eq) and (1S,3R)-3-((benzyloxy)carbonyl)-2,2-dimethylcyclobutane-1-carboxylic acid (prepared as described in WO 2013/160810 A2, 0.751 g, 2.867 mmol, 1.5 eq) in DCM (13 ml) at 0° C. were added triethylamine (1.33 ml, 9.558 mmol, 5.0 eq), DMAP (0.116 g, 0.955 mmol, 0.5 eq) and 2,4,6- trichlorobenzoyl chloride (0.45 ml, 2.867 mmol, 1.5 eq). The reaction mixture was allowed to stir at room temperature for overnight. TLC indicated starting material was consumed and the desired product was observed. The reaction mixture was diluted with water (50 ml) and extracted with DCM (3×50 ml). The combined organic extracts were washed with brine solution (50 ml), dried over Na$_2$SO$_4$, filtered and evaporated under reduced pressure. The residue was purified by silicagel column chromatography by using 5% methanol in DCM as an eluent to obtain the desired product (0.87 g, 50.28% yield) as a brown color solid. $^1$H NMR (300 MHz, CDCl$_3$): δ ppm 7.75-7.72 (m, 2H), 7.40-7.30 (m, 7H), 7.30-7.20 (m, 2H), 5.15, 5.09 (ABq, J$_{AB}$=12.3 Hz, 2H), 5.07-5.0 (m, 1H), 4.44 (dd, J=11.1, 4.5 Hz, 1H), 3.45-3.35 (m, 2H), 3.20-3.08 (m, 1H), 3.0-2.60 (m, 5H), 2.40-2.20 (m, 5H), 2.20-1.90 (m, 4H), 1.90-1.20 (m, 22H), 1.10-0.78 (m, 20H).

Step 4: Synthesis of (1R,3S)-3-((((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR,9S,11aR,11bR,13aS)-1-iso propyl-5a,5b,8,8,11a-pentamethyl-2-oxo-3a-((S)-2-(5-phenyl-1H-imidazol-2-yl)pyrrolidine-1-carboxamido)-3,3a,4,5,5a,5b,6,7,7a,8,9,10,11,11a,11b,12,13,13a-octadecahydro-2H-cyclo penta[a]chrysen-9-yl) (1R,3S)-2,2-dimethylcyclobutane-1,3-dicarboxylate (step 3, 0.870 g, 0.957 mmol, 1.0 eq) in MeOH (17.4 ml) and THF (17.4 ml) was added aqueous 2.5N KOH solution (2.82 ml, 7.05 mmol, 7.5 eq). The reaction mixture was allowed to stir at room temperature for overnight. TLC indicated starting material was consumed and the desired product was observed. The organic phase was evaporated under reduced pressure, reaction mixture was diluted with water (50 ml), cooled to 0° C., acidified with 1N HCl to pH-5 and extracted with DCM (2×50 ml). The combined organic extracts were washed with water (50 ml), dried over sodium sulfate, filtered and evaporated under reduced pressure. The residue was purified by silicagel column chromatography by using 5% methanol in DCM as an eluent to obtain the desired product (0.23 g, 29.2% yield) as a brown color solid. $^1$H NMR (300 MHz, CDCl$_3$): δ ppm 12.04 (br.s., 1H), 7.72 (d, J=7.2 Hz, 2H), 7.54 (s, 1H), 7.38-7.28 (m, 2H), 7.20-7.10 (m, 1H), 6.37 (s, 1H), 4.90-4.82 (m, 1H), 4.40-4.28 (m, 1H), 3.52-3.40 (m, 2H), 3.10-2.96 (m, 1H), 2.84-2.70 (m, 3H), 2.38-2.22 (m, 3H), 2.20-2.0 (m, 4H), 2.0-1.30 (m, 12H), 1.30-1.23 (m, 4H), 1.23-1.16 (m, 3H), 1.15-0.98 (m, 8H), 0.91 (s, 3H), 0.87-0.73 (m, 16H); ESI-MS: m/z 835.56 (M+H)$^+$; HPLC: 94.9%.

Example 4: Preparation of (1R,3S)-3-((((3aR,5aR,5bR,7aR,9S,11aR,11bR,13aS)-3a-(3-(1-(4-chlorophenyl)cyclopropyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid

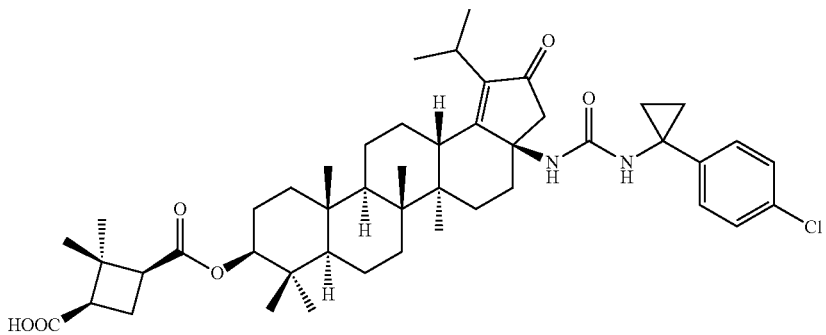

Step 1: Synthesis of 1-benzyl 3-((3aR,5aR,5bR, 7aR,9S,11aR,11bR,13aS)-3a-(3-(1-(4-chloro phenyl) cyclopropyl)ureido)-1-isopropyl-5a,5b,8,8,11a-pentamethyl-2-oxo-3,3a,4,5,5a,5b,6,7,7a,8,9,10,11,11a, 11b,12,13,13a-octadecahydro-2H-cyclopenta[a] chrysen-9-yl) (1R,3S)-2,2-dimethylcyclobutane-1,3-dicarboxylate

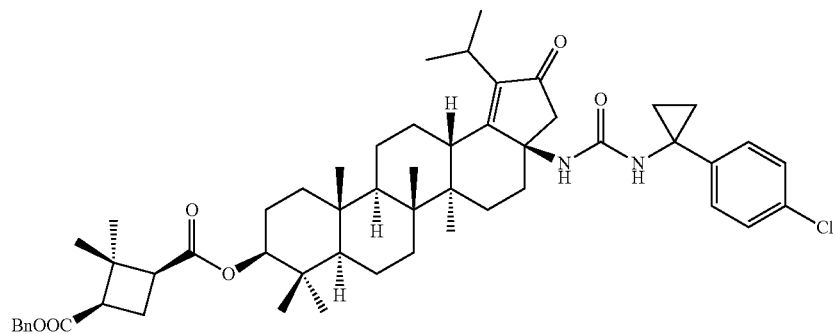

To a stirred solution of 1-benzyl 3-((3aR,5aR,5bR,7aR, 9S,11aR,11bR,13aS)-3a-iso cyanato-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclo butane-1,3-dicarboxylate (Intermediate-2, 3.0 g, 4.213 mmol, 1.0 eq) in THF (30 ml) was added DIPEA (2.16 ml, 12.64 mmol, 3.0 eq) followed by 1-(4-chlorophenyl)cyclopropan-1-amine (Intermediate-4, 0.847 g, 5.056 mmol, 1.2 eq). The reaction mixture was stirred at room temperature for about 16 hours. TLC indicated starting material was consumed and the desired product was observed. The reaction mixture was diluted with water (75 ml) and extracted with ethyl acetate (3×75 ml). The combined organic extracts were washed with water (75 ml) and brine solution (50 ml). The organic layer was dried over sodium sulfate, filtered and evaporated under reduced pressure. The residue was purified by silicagel column chromatography by using 0-2% methanol in dichloromethane gradient. The fractions containing the expected product were combined and concentrated under reduced pressure to give the desired product (3.0 g, 80.9% yield) as a white solid. $^1$H NMR (300 MHz, CDCl$_3$): δ ppm 7.37-7.34 (m, 5H), 7.30 (d, J=8.7 Hz, 2H), 7.13 (d, J=8.7 Hz, 2H), 5.16, 5.10 (ABq, J$_{AB}$=12.3 Hz, 2H), 5.09 (s, 1H), 4.76 (s, 1H), 4.44 (dd, J=11.4, 4.8 Hz, 1H), 3.18-3.07 (m, 1H), 2.87-2.57 (m, 5H), 2.20 (d, J=18.3 Hz, 1H), 2.14-1.98 (m, 2H), 1.91-1.80 (m, 2H), 1.80-1.61 (m, 4H), 1.56-1.39 (m, 4H), 1.39-1.25 (m, 6H), 1.34 (s, 3H), 1.22 (s, 3H), 1.19 (s, 3H), 1.17-1.0 (m, 4H), 0.97 (s, 3H), 0.91 (s, 3H), 0.88 (s, 3H), 0.85 (s, 6H), 0.79 (m, 1H), 0.75 (s, 3H); ESI-MS: m/z 901.46 (M+Na)$^+$.

Step 2: Synthesis of (1R,3S)-3-((((3aR,5aR,5bR, 7aR,9S,11aR,11bR,13aS)-3a-(3-(1-(4-chloro phenyl) cyclopropyl)ureido)-1-isopropyl-5a, 5b,8,8,11a-pentamethyl-2-oxo-3,3a, 4,5,5a, 5b,6,7,7a,8,9,10,11, 11a,11b,12,13,13a-octadecahydro-2H-cyclopenta[a] chrysen-9-yl)oxy) carbonyl)-2,2-dimethylcyclobutane-1-carboxylic acid To a stirred solution of 1-benzyl 3-((3aR,5aR,5bR,7aR, 9S,11aR,11bR,13aS)-3a-(3-(1-(4-chlorophenyl)cyclopropyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 3.0 g, 3.41 mmol, 1.0 eq) in MeOH (60 ml) and THF (60 ml) was added aqueous 2.5N KOH solution (10.23 ml, 25.579 mmol, 7.5 eq). The reaction mixture was stirred at room temperature for overnight. TLC indicated starting material was consumed and the desired product was observed. The organic phase was evaporated under reduced pressure. The reaction mixture was cooled to 0° C., diluted with water (25 ml), pH adjusted to 5.0 with 1N HCl and extracted with DCM (3×75 ml). The combined organic extracts were washed with water (75 ml), dried over sodium sulfate, filtered and evaporated under reduced pressure. The residue was purified by silicagel column chromatography by using 0-4% methanol in dichloromethane gradient. The fractions containing the expected product were combined and concentrated under reduced pressure to obtain the solid. To this resulting solid compound, methyl-tert-butyl ether:hexane (80 ml, 1:2) was added and heated to reflux for about 30 minutes, then slowly cooled to 0° C., filtered and dried under vacuum to obtain the desired product (1.74 g, 64.63% yield) as a white solid. $^1$H NMR (300 MHz, CDCl$_3$): δ ppm 7.29 (d, J=8.7 Hz, 2H), 7.15 (d, J=8.4 Hz, 2H), 5.63 (s, 1H), 4.97 (s, 1H), 4.48 (dd, J=11.1, 4.5 Hz, 1H), 3.18-3.07 (m, 1H), 2.87-2.68 (m, 3H), 2.68-2.53 (m, 2H), 2.20 (d, J=18.6 Hz, 1H), 2.12-2.02 (m, 2H), 1.90-1.80 (m, 2H), 1.73-1.65 (m, 4H), 1.50-1.40 (m, 3H), 1.40-1.30 (m, 5H), 1.38 (s, 3H), 1.30-1.07 (m, 10H), 1.09 (s, 3H), 1.07-0.75 (m, 15H), 0.70 (s, 3H); ESI-MS: m/z 789.4 (M+H)$^+$.

Example 5: Preparation of (1R,3S)-3-((((3aR,5aR, 5bR,7aR,9S,11aR,11bR,13aS)-3a-(3-(2-(4-chlorophenyl)propan-2-yl)ureido)-1-isopropyl-5a,5b,8,8, 11a-pentamethyl-2-oxo-3,3a,4,5,5a,5b,6,7,7a,8,9,10, 11,11a,11b,12,13,13a-octadecahydro-2H-cyclopenta [a]chrysen-9-yl)oxy) carbonyl)-2,2-dimethylcyclobutane-1-carboxylic acid

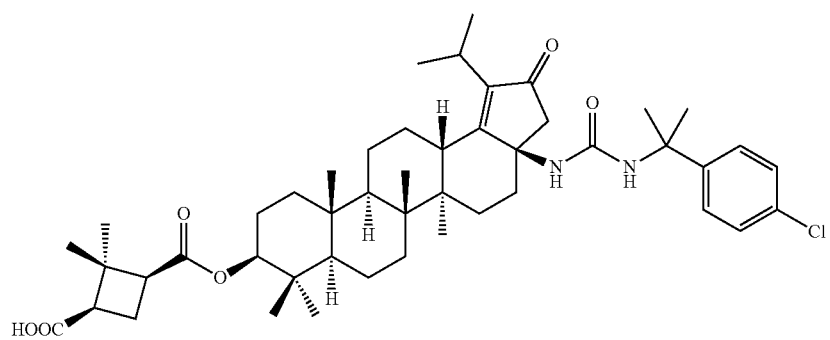

Step 1: Synthesis of 1-benzyl 3-((3aR,5aR,5bR, 7aR,9S,11aR,11bR,13aS)-3a-(3-(2-(4-chloro phenyl) propan-2-yl)ureido)-1-isopropyl-5a,5b,8,8,11a-pentamethyl-2-oxo-3,3a,4,5,5a,5b,6,7,7a,8,9,10,11,11a, 11b,12,13,13a-octadecahydro-2H-cyclopenta[a] chrysen-9-yl) (1R,3S)-2,2-dimethylcyclobutane-1,3-dicarboxylate

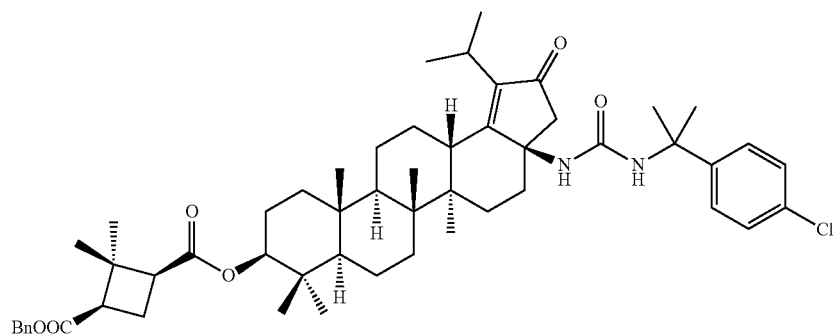

To a stirred solution of 1-benzyl 3-((3aR,5aR,5bR,7aR, 9S,11aR,11bR,13aS)-3a-iso cyanato-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclo butane-1,3-dicarboxylate (Intermediate-2, 1.0 g, 1.40 mmol, 1.0 eq) in THF (15 ml) was added DIPEA (0.72 g, 5.62 mmol, 4.0 eq) and 2-(4-chlorophenyl)propan-2-amine (Intermediate-5, 0.35 g, 2.1 mmol, 1.5 eq). The reaction mixture was stirred at room temperature for about 16 hours. TLC indicated starting material was consumed and the desired product was observed. The reaction mixture was diluted with water (50 ml) and extracted with ethyl acetate (3×60 ml). The combined organic extracts were dried over sodium sulfate, filtered and evaporated under reduced pressure. The residue was purified by silicagel column chromatography by using 50% ethyl acetate:hexane as an eluent to obtain the desired product (0.804 g, 65.0% yield) as a white solid. $^1$H NMR (300 MHz, CDCl$_3$): δ ppm 7.40-7.30 (m, 9H), 5.15, 5.10 (ABq, J$_{AB}$=12.3 Hz, 2H), 4.65 (s, 1H), 4.44 (dd, J=11.1, 4.8 Hz, 1H), 4.04 (s, 1H), 3.15-3.05 (m, 1H), 2.86-2.54 (m, 5H), 2.252 (d, J=18.9 Hz, 1H), 2.18-2.10 (m, 1H), 2.09-2.0 (m, 1H), 1.95-1.82 (m, 1H), 1.80-1.65 (m, 4H), 1.60 (s, 3H), 1.55 (s, 3H), 1.54-1.50 (m, 1H), 1.49-1.30 (m, 5H), 1.34 (s, 3H), 1.30-1.10 (m, 10H), 1.08-1.03 (m, 1H), 1.05 (s, 3H), 0.96 (s, 3H), 0.95 (s, 3H), 0.89-0.83 (m, 9H), 0.81-0.78 (m, 1H); ESI MS: m/z 903.6 (M+Na)$^+$.

Step 2: Synthesis of (1R,3S)-3-(((((3aR,5aR,5bR, 7aR,9S,11aR,11bR,13aS)-3a-(3-(2-(4-chloro phenyl) propan-2-yl)ureido)-1-isopropyl-5a,5b,8,8,11a-pentamethyl-2-oxo-3,3a,4,5,5a,5b,6,7,7a,8,9,10,11,11a, 11b,12,13,13a-octadecahydro-2H-cyclopenta[a] chrysen-9-yl)oxy) carbonyl)-2,2-dimethylcyclobutane-1-carboxylic acid To a stirred solution of 1-benzyl 3-((3aR,5aR,5bR,7aR, 9S,11aR,11bR,13aS)-3a-(3-(2-(4-chlorophenyl)propan-2-yl)ureido)-1-isopropyl-5a,5b,8,8,11a-pentamethyl-2-oxo-3, 3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 0.800 g, 0.908 mmol, 1.0 eq) in MeOH (20 ml) and THF (20 ml) was added aqueous 2.5N KOH solution (2.7 ml, 6.81 mmol, 7.5 eq). The reaction mixture was stirred at room temperature for about 16 hours. TLC indicated starting material was consumed and the desired product was observed. The organic phase was evaporated under reduced pressure, the reaction mixture was cooled to 0° C., diluted with water (10 ml), acidified with 1N HCl to pH 5.0 and extracted with DCM (3×50 ml). The combined organic extracts were dried over sodium sulfate, filtered and evaporated under reduced pressure. The residue was purified by silicagel column chromatography (eluent 8% MeOH:DCM), followed by recrystallization over acetonitrile gave the desired product (0.190 g, 26% yield) as a white solid. $^1$H NMR (300 MHz, DMSO-$d_6$): δ ppm 12.1 (br.s., 1H), 7.34 (d, J=8.7 Hz, 2H), 7.28 (d, J=8.4 Hz, 2H), 6.31 (s, 1H), 6.14 (s, 1H), 4.41-4.34 (m, 1H), 3.07-2.98 (m, 1H), 2.90-2.72 (m, 4H), 2.42-2.24 (m, 2H), 2.14-2.02 (m, 2H), 2.0-1.82 (m, 3H), 1.80-1.56 (m, 5H), 1.52 (s, 3H), 1.47-1.42 (m, 1H), 1.44 (s, 3H), 1.41-1.33 (m, 2H), 1.31-1.23 (m, 2H), 1.27 (s, 3H), 1.22-1.16 (m, 1H), 1.18 (s, 3H), 1.15-1.0 (m, 8H), 0.97-0.79 (m, 16H); ESI MS: m/z 791.5 (M+H)$^+$; HPLC: 98.3%.

Example 6: Preparation of (1R,3S)-3-(((((3aR,5aR, 5bR,7aR,9S,11aR,11bR,13aS)-3a-(3-((1-(4-chlorophenyl)cyclopropyl)methyl)-3-(2-(dimethylamino) ethyl)ureido)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a] chrysen-9-yl)oxy)carbonyl)-2,2-dimethylcyclobutane-1-carboxylic acid

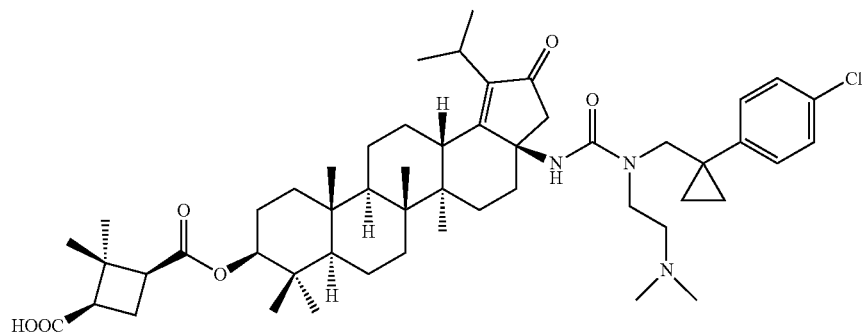

Step 1: Synthesis of 1-benzyl 3-((3aR,5aR,5bR,7aR,9S,11aR,11bR,13aS)-3a-(3-((1-(4-chloro phenyl)cyclopropyl)methyl)-3-(2-(dimethylamino)ethyl) ureido)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

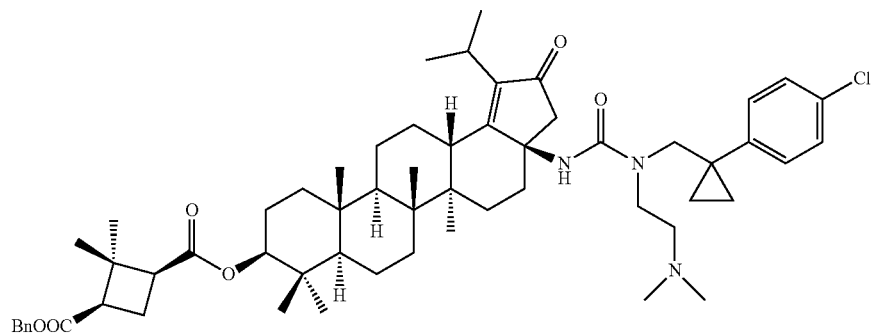

To a stirred solution of 1-benzyl 3-((3aR,5aR,5bR,7aR,9S,11aR,11bR,13aS)-3a-isocyanato-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclo butane-1,3-dicarboxylate (Intermediate-2, 1.0 g, 1.404 mmol, 1.0 eq) in THF (10 ml) was added DIPEA (0.96 ml, 5.616 mmol, 4.0 eq) and $N^1$-((1-(4-chlorophenyl)cyclopropyl)methyl)-$N^2$,$N^2$-dimethylethane-1,2-diamine (Intermediate-6, 0.7 g, 2.808 mmol, 2.0 eq). The reaction mixture was stirred at room temperature for about 16 hours. TLC indicated starting material was consumed and the desired product was observed. The reaction mixture was diluted with water (15 ml) and extracted with DCM (3×50 ml). The combined organic extracts were dried over sodium sulfate, filtered and evaporated under reduced pressure. The residue was purified by silicagel column chromatography by using 4% MeOH in DCM as an eluent to obtain the desired product (0.8 g, 59% yield) as a white solid. $^1$H NMR (300 MHz, CDCl$_3$): δ ppm 7.35 (m, 5H), 7.24 (m, 4H), 5.16, 5.10 (ABq, J$_{AB}$=12.3 Hz, 2H), 4.46 (dd, J=11.1, 4.5 Hz, 1H), 3.70-3.43 (m, 2H), 3.37-3.20 (m, 1H), 3.20-3.04 (m, 2H), 2.95-2.75 (m, 3H), 2.73-2.60 (m, 1H), 2.58-2.42 (m, 2H), 2.41-2.29 (m, 2H), 2.23-2.0 (m, 8H), 1.99-1.80 (m, 3H), 1.80-1.70 (m, 3H), 1.67-1.50 (m, 4H), 1.50-1.25 (m, 5H), 1.35 (s, 3H), 1.25-1.18 (m, 6H), 1.09 (s, 3H), 1.05 (m, 1H), 0.97 (s, 3H), 0.93 (s, 3H), 0.91 (s, 3H), 0.90-0.82 (m, 10H), 0.79 (m, 1H); ESI-MS: m/z 964.53 (M+H)$^+$.

Step 2: Synthesis of (1R,3S)-3-(((((3aR,5aR,5bR,7aR,9S,11aR,11bR,13aS)-3a-(3-((1-(4-chloro phenyl)cyclopropyl)methyl)-3-(2-(dimethylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR,9S,11aR,11bR,13aS)-3a-(3-((1-(4-chlorophenyl)cyclopropyl)methyl)-3-(2-(dimethylamino)ethyl)ureido)-1-isopropyl-5a,5b, 8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 0.8 g, 0.829 mmol, 1.0 eq) in MeOH (16 ml) and THF (16 ml) was added aqueous 2.5N KOH solution (2.5 ml, 6.21 mmol, 7.5 eq). The reaction mixture was stirred at room temperature for overnight. TLC indicated starting material was consumed and the desired product was observed. The organic phase was evaporated under reduced pressure, reaction mixture was diluted with water (15 ml), cooled to 0° C., pH adjusted to 6.0 with 1N HCl and extracted with DCM (3×30 ml). The combined organic extracts were washed with water (30 ml), dried over sodium sulfate, filtered and evaporated under reduced pressure. The residue was purified by silicagel column chromatography by using 0-6% methanol in dichloromethane gradient. The fractions containing the expected product were combined and concentrated under reduced pressure to obtain the solid. To this solid compound, MTBE (10 ml) was added and heated to reflux for about 30 minutes. The mixture was cooled to 0° C., filtered and was washed with n-hexane (5 ml) and dried under vacuum to obtain the desired product (0.12 g, 16.5% yield) as a white solid. $^1$H NMR (300 MHz, CDCl$_3$): δ ppm 7.24 (m, 4H), 4.48 (dd, J=11.1, 4.5 Hz, 1H), 3.60-3.24 (m, 3H), 3.23-3.05 (m, 2H), 2.92-2.72 (m, 3H), 2.62-2.38 (m, 4H), 2.26 (m, 1H), 2.20 (s, 6H), 2.08-1.92 (m, 2H), 1.88-1.67 (m, 4H), 1.65-1.47 (m, 4H), 1.45-1.35 (m, 2H), 1.37 (s, 3H), 1.33-1.18 (m, 4H), 1.22 (s, 3H), 1.20 (s, 3H), 1.14-0.98 (m, 2H), 1.08 (s, 3H), 1.06 (s, 3H), 0.96-0.78 (m, 17H); ESI-MS: m/z 874.51 (M+H)$^+$.

Example 7: Preparation of (1R,3S)-3-(((((3aR,5aR,5bR,7aR,9S,11aR,11bR,13aS)-3a-(3-(4-chlorobenzyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

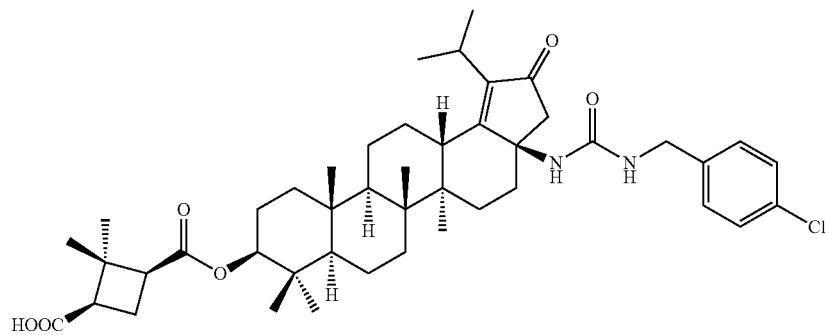

Step 1: Synthesis of 1-benzyl 3-((3aR,5aR,5bR, 7aR,9S,11aR,11bR,13aS)-3a-(3-(4-chloro benzyl) ureido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) (1R,3S)-2,2-dimethylcyclo butane-1,3-dicarboxylate

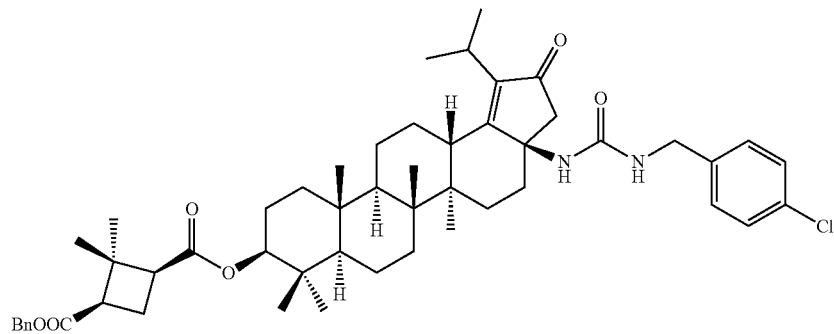

To a stirred solution of 1-benzyl 3-((3aR,5aR,5bR,7aR, 9S,11aR,11bR,13aS)-3a-isocyanato-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclo butane-1,3-dicarboxylate (Intermediate-2, 1.0 g, 1.40 mmol, 1.0 eq) in THF (20 ml) was added DIPEA (0.725 g, 5.62 mmol, 4.0 eq) and (4-chlorophenyl)methanamine (0.394 g, 2.812 mmol, 2.0 eq). The reaction mixture was stirred at room temperature for about 16 hours. TLC indicated starting material was consumed and the desired product was observed. The reaction mixture was diluted with water (50 ml) and extracted with DCM (3×100 ml). The combined organic extracts were dried over sodium sulfate, filtered and evaporated under reduced pressure. The residue was purified by silicagel column chromatography by using 6-8% methanol in DCM as an eluent to obtain the desired product (0.8 g, 67% yield) as a white solid. $^1$H NMR (300 MHz, CDCl$_3$): δ ppm 7.40-7.35 (m, 4H), 7.35-7.25 (m, 3H), 7.18 (d, J=8.4 Hz, 2H), 5.15, 5.09 (ABq, J$_{AB}$=12.6 Hz, 2H), 4.50-4.37 (m, 3H), 3.13-3.02 (m, 1H), 2.90-2.75 (m, 2H), 2.72-2.60 (m, 2H), 2.29 (d, J=15.6 Hz, 1H), 2.18-2.0 (m, 3H), 1.98-1.80 (m, 2H), 1.79-1.63 (m, 4H), 1.55-1.37 (m, 6H), 1.34 (s, 3H), 1.33-1.27 (m, 3H), 1.25 (s, 3H), 1.22-1.17 (m, 3H), 1.17-1.10 (m, 1H), 1.08 (s, 3H), 0.96 (s, 3H), 0.93 (s, 3H), 0.91 (s, 3H), 0.85 (s, 6H), 0.82-0.77 (m, 1H).

Step 2: Synthesis of (1R,3S)-3-((((3aR,5aR,5bR, 7aR,9S,11aR,11bR,13aS)-3a-(3-(4-chloro benzyl) ureido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen- 9-yl) oxy)carbonyl)-2,2-dimethyl cyclobutane-1-carboxylic acid To a stirred solution of 1-benzyl 3-((3aR,5aR,5bR,7aR,9S,11aR,11bR,13aS)-3a-(3-(4-chlorobenzyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethyl cyclobutane-1,3-dicarboxylate (step 1, 0.8 g, 0.938 mmol, 1.0 eq) in MeOH (15 ml) and THF (15 ml) was added aqueous 2.5N KOH solution (2.81 ml, 7.04 mmol, 7.5 eq). The reaction mixture was stirred at room temperature for overnight. TLC indicated starting material was consumed and the desired product was observed. The organic phase was evaporated under reduced pressure, reaction mixture was cooled to 0° C., acidified with 2N HCl and extracted with DCM (3×150 ml). The combined organic extracts were washed with water, dried over sodium sulfate, filtered and evaporated under reduced pressure. The residue was purified by silicagel column chromatography by using 0-3% MeOH in DCM gradient. The fractions containing the expected product were combined and concentrated under reduced pressure to obtain the desired product (0.19 g, 26.57% yield) as an off-white solid. $^1$H NMR (300 MHz, DMSO-$d_6$): δ ppm 12.2 (s, 1H), 7.35 (d, J=8.1 Hz, 2H), 7.24 (d, J=8.4 Hz, 2H), 6.32-6.23 (m, 2H), 4.42-4.32 (m, 1H), 4.27-4.15 (m, 2H), 3.12-3.02 (m, 1H), 2.85-2.72 (m, 3H), 2.46-2.42 (m, 2H), 2.38-2.25 (m, 1H), 2.17-2.08 (m, 2H), 2.0-1.83 (m, 3H), 1.75-1.30 (m, 9H), 1.27 (s, 3H), 1.23 (m, 2H), 1.20-1.07 (m, 8H), 1.05 (s, 3H), 0.93-0.87 (m, 9H), 0.82 (m, 7H); ESI-MS: m/z 785.46 (M+Na)+; HPLC: 98.4%.

Example 8: Preparation of (1R,3S)-3-((((3aR,5aR, 5bR,7aR,9S,11aR,11bR,13aS)-1-isopropyl-3a-((1R, 3S,5S)-3-(3-isopropyl-5-methyl-4H-1,2,4-triazol-4-yl)-8-azabicyclo[3.2.1]octane-8-carboxamido)-5a,5b, 8,8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl)oxy)carbonyl)-2,2-dimethylcyclobutane-1-carboxylic acid

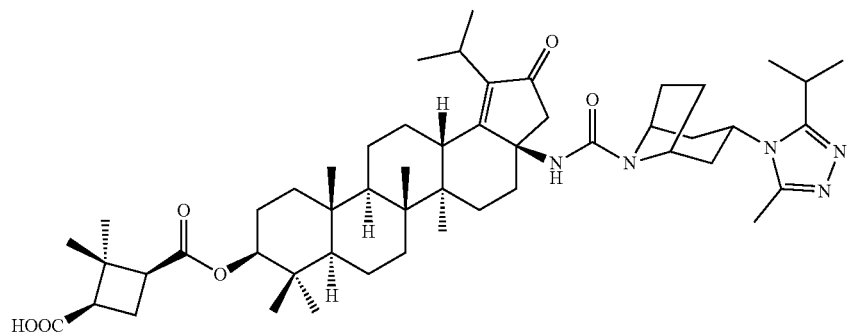

Step 1: Synthesis of 1-benzyl 3-((3aR,5aR,5bR,7aR,9S,11aR,11bR,13aS)-1-isopropyl-3a-((1R,3S,5S)-3-(3-isopropyl-5-methyl-4H—,2,4-triazol-4-yl)-8-azabicyclo[3.2.]octane-8-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

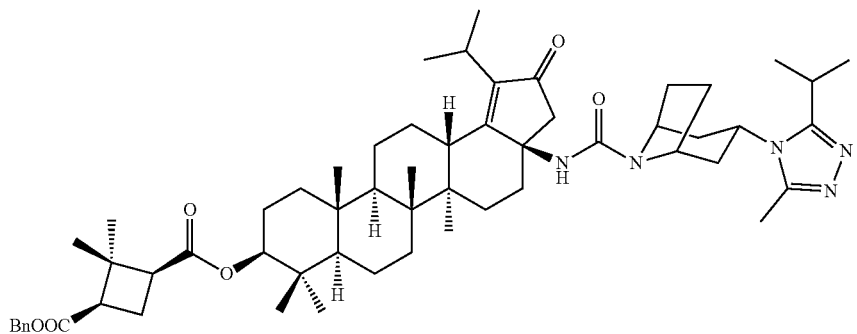

To a stirred solution of 1-benzyl 3-((3aR,5aR,5bR,7aR,9S,11aR,11bR,13aS)-3a-isocyanato-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclo butane-1,3-dicarboxylate (Intermediate-2, 1.0 g, 1.40 mmol, 1.0 eq) in THF (15 ml) was added DIPEA (0.722 g, 5.6 mmol, 4.0 eq) and (1R,3S,5S)-3-(3-isopropyl-5-methyl-4H-1,2,4-triazol-4-yl)-8-azabicyclo[3.2.1]octane (0.655 g, 2.8 mmol, 2.0 eq). The reaction mixture was stirred at room temperature for about 16 hours. After completion of the reaction (monitored by TLC), the reaction mixture was diluted with water (50 ml) and extracted with EtOAc (3×50 ml). The combined organic extracts were dried over sodium sulfate, filtered and evaporated under reduced pressure. The residue was purified by silicagel column chromatography by using 5% methanol in DCM as an eluent to obtain the desired product (0.65 g, 49% yield) as a white solid. $^1$H NMR (300 MHz, DMSO-$d_6$): δ ppm 7.36 (m, 5H), 6.49 (s, 1H), 5.12, 5.06 (ABq, 2H), 4.48-4.30 (m, 4H), 3.20-3.08 (m, 4H), 3.0-2.80 (m, 3H), 2.34 (s, 3H), 2.22-2.03 (m, 4H), 2.02-1.73 (m, 11H), 1.70-1.33 (m, 10H), 1.32-1.20 (m, 10H), 1.20-1.12 (m, 6H), 1.07-0.98 (m, 6H), 0.91 (s, 3H), 0.88-0.78 (m, 11H).

Step 2: Synthesis of (1R,3S)-3-((((3aR,5aR,5bR, 7aR,9S,11aR,11bR,13aS)-1-isopropyl-3a-((1R,3S, 5S)-3-(3-isopropyl-5-methyl-4H-1,2,4-triazol-4-yl)- 8-azabicyclo[3.2.1]octane-8-carboxamido)-5a,5b,8, 8,11a-pentamethyl-2-oxo-3,3a,4,5,5a,5b,6,7,7a,8,9, 10,11,11a,11b,12,13,13a-octadecahydro-2H- cyclopenta[a]chrysen-9-yl)oxy)carbonyl)-2,2- dimethylcyclo butane-1-carboxylic acid To a suspension of wet 10% Pd/C (1.0 g) in EtOAc (70 ml) was added 1-benzyl 3-((3aR,5aR,5bR,7aR,9S,11aR, 11bR,13aS)-1-isopropyl-3a-((1R,3S,5S)-3-(3-isopropyl-5-methyl-4H-1,2,4-triazol-4-yl)-8-azabicyclo[3.2.1]octane-8-carboxamido)-5a,5b,8,8,11a-penta methyl-2-oxo-3,3a,4,5, 5a,5b,6,7,7a,8,9,10,11,11a,11b,12,13,13a-octadecahydro-2H-cyclo penta[a]chrysen-9-yl) (1R,3S)-2,2-dimethylcyclobutane-1,3-dicarboxylate (step 1, 0.65 g, 0.68 mmol, 1.0 eq) in methanol (70 ml). To this stirred reaction mixture, ammonium formate (0.433 g, 6.87 mmol, 10.0 eq) was added portion wise and stirred for about 2 hours at room temperature. TLC indicated starting material was consumed and the desired product was observed. The reaction mixture was diluted with EtOAc and filtered through a pad of celite. The filtrate was washed with water; the organic layer was dried over $Na_2SO_4$, filtered and concentrated under reduced pressure. The crude compound was purified by silicagel column chromatography by using 10% methanol in DCM as an eluent to obtain the desired product (0.29 g, 49% yield) as a white solid. $^1$H NMR (300 MHz, DMSO-$d_6$): δ ppm 12.1 (br.s., 1H), 6.50 (s, 1H), 4.50-4.25 (m, 4H), 3.18-2.93 (m, 4H), 2.83-2.72 (m, 2H), 2.48-2.42 (m, 1H), 2.34 (s, 3H), 2.30-2.04 (m, 4H), 2.04-1.70 (m, 11H), 1.68-1.50 (m, 5H), 1.47-1.33 (m, 5H), 1.28-1.20 (m, 10H), 1.17-1.02 (m, 6H), 1.04 (s, 3H), 1.02-0.98 (m, 1H), 0.91 (s, 6H), 0.88-0.78 (m, 10H); ESI-MS: m/z 856.58 (M+H)$^+$; HPLC: 95.7%.

Example 9: Preparation of (1R,3S)-3-((((3aR,5aR, 5bR,7aR,9S,11aR,11bR,13aS)-3a-(3-(4-chloroben- zyl)-3-(2-(pyrrolidin-1-yl)ethyl)ureido)-1-isopropyl- 5a,5b,8,8,11a-pentamethyl-2-oxo-3,3a,4,5,5a,5b,6,7, 7a,8,9,10,11,11a,11b,12,13,13a-octadecahydro-2H- cyclopenta[a]chrysen-9-yl)oxy)carbonyl)-2,2- dimethylcyclobutane-1-carboxylic acid

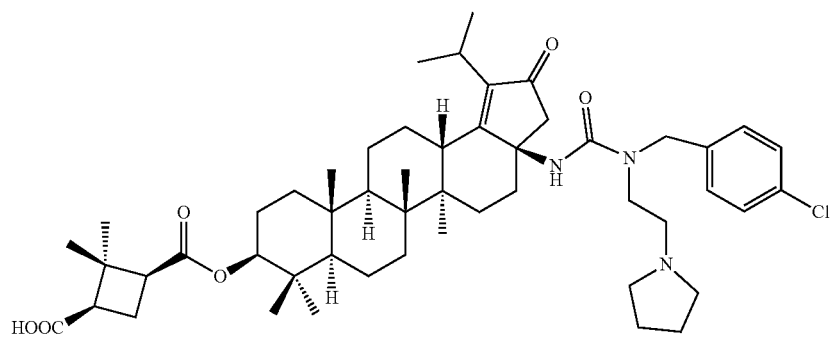

Step 1: Synthesis of 1-benzyl 3-((3aR,5aR,5bR, 7aR,9S,11aR,11bR,13aS)-3a-(3-(4-chloro benzyl)-3- (2-(pyrrolidin-1-yl)ethyl)ureido)-1-isopropyl-5a,5b, 8,8,11a-pentamethyl-2-oxo-3,3a,4,5,5a,5b,6,7,7a,8,9, 10,11,11a,11b,12,13,13a-octadecahydro-2H- cyclopenta[a]chrysen-9-yl) (1R,3S)-2,2- dimethylcyclobutane-1,3-dicarboxylate

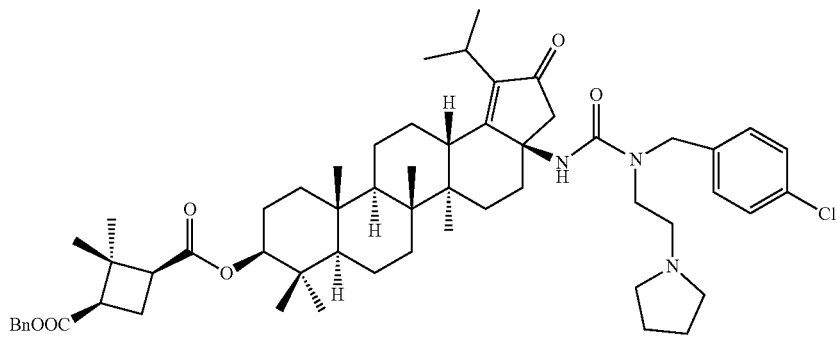

To a stirred solution of 1-benzyl 3-((3aR,5aR,5bR,7aR, 9S,11aR,11bR,13aS)-3a-isocyanato-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9- yl) (1R,3S)-2,2-dimethylcyclo butane-1,3-dicarboxylate (Intermediate-2, 1.0 g, 1.40 mmol, 1.0 eq) in THF (15 ml) was added N-(4-chlorobenzyl)-2-(pyrrolidin-1-yl)ethan-1- amine (Intermediate-7, 0.67 g, 2.81 mmol, 2.0 eq), followed by DIPEA (0.722 g, 5.62 mmol, 4.0 eq). The reaction mixture was stirred at room temperature for about 16 hours. TLC indicated starting material was consumed and the desired product was observed. The reaction mixture was diluted with water (50 ml) and extracted with EtOAc (3×50 ml). The combined organic extracts were dried over sodium sulfate, filtered and evaporated under reduced pressure. The residue was purified by silicagel column chromatography by using 6% methanol in DCM as an eluent to obtain the desired product (0.5 g, 37% yield) as a white solid. $^1$H NMR (300 MHz, CDCl$_3$): δ ppm 7.40-7.25 (m, 7H), 7.17 (d, J=7.1 Hz, 2H), 5.18-5.08 (m, 2H), 4.52-4.42 (m, 3H), 3.60-3.25 (m, 3H), 3.20-3.02 (m, 2H), 3.0-2.57 (m, 8H), 2.48-2.28 (m, 2H), 2.10-2.0 (m, 2H), 2.0-1.80 (m, 5H), 1.80-1.50 (m, 7H), 1.50-1.0 (m, 17H), 0.94 (s, 3H), 0.92-0.87 (m, 9H), 0.85 (m, 6H), 0.79 (m, 1H); ESI-MS: m/z 950.65 (M+H)$^+$.

Step 2: Synthesis of (1R,3S)-3-((((3aR,5aR,5bR, 7aR,9S,11aR,11bR,13aS)-3a-(3-(4-chloro benzyl)-3-(2-(pyrrolidin-1-yl)ethyl)ureido)-1-isopropyl-5a,5b, 8,8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR, 9S,11aR,11bR,13aS)-3a-(3-(4-chlorobenzyl)-3-(2-(pyrrolidin-1-yl)ethyl)ureido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) (1R,3S)-2,2-dimethylcyclobutane-1,3-dicarboxylate (step 1, 0.5 g, 0.526 mmol, 1.0 eq) in THF (10 ml) and MeOH (10 ml) was added aqueous 2.5N KOH solution (1.57 ml, 3.95 mmol, 7.5 eq). The reaction mixture was stirred at room temperature for about 16 hours. TLC indicated starting material was consumed and the desired product was observed. The organic phase was evaporated under reduced pressure, reaction mixture was neutralized with 1N HCl and extracted with DCM (3×50 ml). The combined organic extracts were dried over sodium sulfate, filtered and evaporated under reduced pressure. The residue was purified by silicagel column chromatography by using 0-10% MeOH in DCM gradient. The fractions containing the expected product were combined and concentrated under reduced pressure to give the desired product (0.06 g, 13% yield) as a white solid. $^1$H NMR (300 MHz, DMSO-$d_6$): δ ppm 7.37 (d, J=8.4 Hz, 2H), 7.21 (d, J=8.4 Hz, 2H), 4.44-4.32 (m, 3H), 3.43-3.36 (m, 2H), 3.20-3.03 (m, 3H), 2.88-2.72 (m, 3H), 2.57-2.40 (m, 7H), 2.37-2.07 (m, 6H), 2.0-1.83 (m, 3H), 1.80-1.52 (m, 9H), 1.52-1.31 (m, 5H), 1.27 (s, 3H), 1.26-1.21 (m, 1H), 1.17-1.08 (m, 7H), 0.96 (s, 3H), 0.93-0.89 (m, 4H), 0.86 (s, 3H), 0.84-0.79 (m, 6H); ESI-MS: m/z 860.57 (M+H)$^+$; HPLC: 96.8%.

Example 10: Preparation of (1R,3S)-3-((((3aR,5aR, 5bR,7aR,9S,11aR,11bR,13aS)-1-iso propyl-5a,5b,8, 8,11a-pentamethyl-2-oxo-3a-(3-(2-(5-phenyl-1H-imidazol-2-yl)propan-2-yl) ureido)-3,3a,4,5,5a,5b,6, 7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

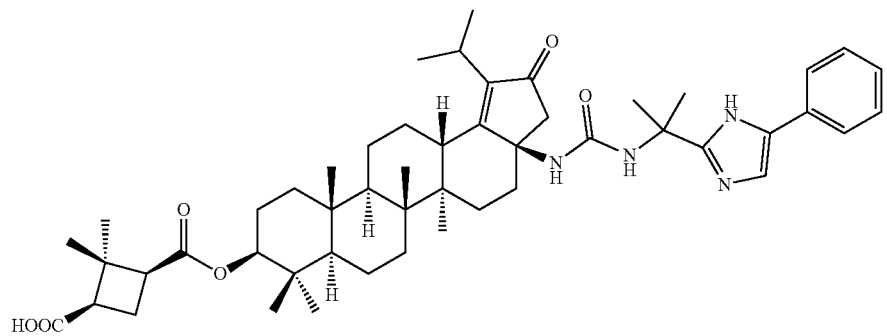

Step 1: Synthesis of 1-benzyl 3-((3aR,5aR,5bR, 7aR,9S,11aR,11bR,13aS)-1-isopropyl-5a,5b,8,8,11a-pentamethyl-2-oxo-3a-(3-(2-(5-phenyl-1H-imidazol-2-yl)propan-2-yl)ureido)-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

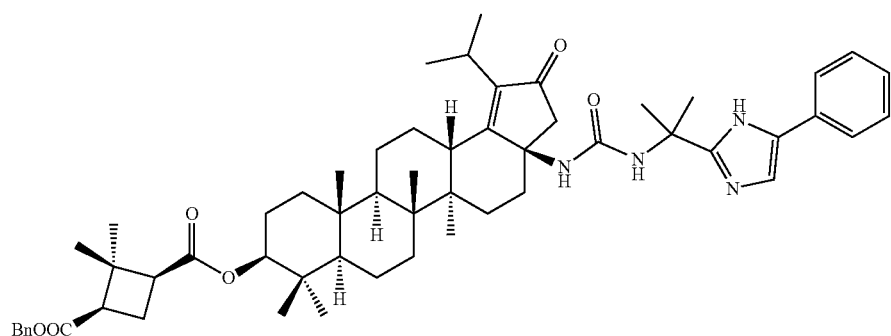

To a stirred solution of 1-benzyl 3-((3aR,5aR,5bR,7aR, 9S,11aR,11bR,13aS)-3a-isocyanato-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclo butane-1,3-dicarboxylate (Intermediate-2, 0.8 g, 1.124 mmol, 1.0 eq) in THF (30 ml) was added DIPEA (1.39 ml, 7.871 mmol, 7.0 eq) and 2-(5-phenyl-1H-imidazol-2-yl)propan-2-amine (Intermediate-8, 0.452 g, 2.249 mmol, 2.0 eq). The reaction mixture was stirred at room temperature for overnight. TLC indicated starting material was consumed and the desired product was observed. The reaction mixture was diluted with water (200 ml) and extracted with DCM (3×200 ml). The combined organic extracts were dried over sodium sulfate, filtered and evaporated under reduced pressure. The residue was purified by silicagel column chromatography by using 2% methanol in DCM as an eluent to obtain the desired product (0.4 g, 40% yield) as a white solid. $^1$H NMR (300 MHz, CDCl$_3$): δ ppm 7.68-7.60 (m, 1H), 7.40-7.31 (m, 5H), 7.29-7.24 (m, 4H), 7.22 (s, 1H), 5.15, 5.09 (ABq, J$_{AB}$=12.3 Hz, 2H), 4.48-4.39 (m, 1H), 3.18-3.08 (m, 1H), 2.83-2.72 (m, 3H), 2.70-2.53 (m, 2H), 2.28-2.10 (m, 3H), 1.98-1.77 (m, 5H), 1.74 (s, 3H), 1.70 (s, 3H), 1.68-1.36 (m, 7H), 1.34 (s, 3H), 1.33-1.18 (m, 6H), 1.17-1.10 (m, 7H), 1.05 (s, 3H), 0.96 (s, 3H), 0.89 (s, 3H), 0.84 (s, 3H), 0.83 (s, 3H), 0.78 (m, 1H).

Step 2: Synthesis of (1R,3S)-3-((((3aR,5aR,5bR,7aR,9S,11aR,11bR,13aS)-1-isopropyl-5a,5b,8,8,11a-pentamethyl-2-oxo-3a-(3-(2-(5-phenyl-1H-imidazol-2-yl)propan-2-yl)ureido)-3,3a,4,5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid To a suspension of wet 10% Pd/C (0.2 g) in EtOAc (10 ml) was added 1-benzyl 3-((3aR,5aR,5bR,7aR,9S,11aR,11bR,13aS)-1-isopropyl-5a,5b,8,8,11a-pentamethyl-2-oxo-3a-(3-(2-(5-phenyl-1H-imidazol-2-yl)propan-2-yl)ureido)-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclo butane-1,3-dicarboxylate (step 1, 0.4 g, 0.438 mmol, 1.0 eq) dissolved in MeOH (10 ml). To this stirred reaction mixture, ammonium formate (0.138 g, 2.192 mmol, 5.0 eq) was added portion wise and stirred at room temperature for about 4 hours. TLC indicated starting material was consumed and the desired product was observed. The reaction mixture was filtered through a pad of celite and was washed with EtOAc. The filtrate was evaporated under reduced pressure and purified by silicagel column chromatography by using 3% methanol in DCM as an eluent to obtain the desired product (0.025 g, 7% yield) as a white solid. $^1$H NMR (300 MHz, CD$_3$OD): δ ppm 7.65 (d, J=7.5 Hz, 2H), 7.40-7.21 (m, 4H), 4.42 (m, 1H), 3.10 (m, 1H), 2.93-2.75 (m, 3H), 2.66-2.40 (m, 2H), 2.22-2.13 (m, 2H), 2.07-1.89 (m, 4H), 1.84-1.75 (m, 2H), 1.70 (s, 3H), 1.69 (s, 3H), 1.67-1.39 (m, 7H), 1.38-1.20 (m, 3H), 1.34 (s, 3H), 1.20-1.13 (m, 6H), 1.12-1.06 (m, 3H), 1.01 (s, 3H), 0.98-0.93 (m, 4H), 0.91 (s, 3H), 0.88 (s, 6H), 0.87-0.83 (m, 1H); ESI-MS: m/z 823.52 (M+H)$^+$; HPLC: 94.9%.

Example 11: Preparation of (1R,3S)-3-((((3aR,5aR,5bR,7aR,9S,11aR,11bR,13aS)-3a-(3-(4-chlorobenzyl)-3-(2-(piperidin-1-yl)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride

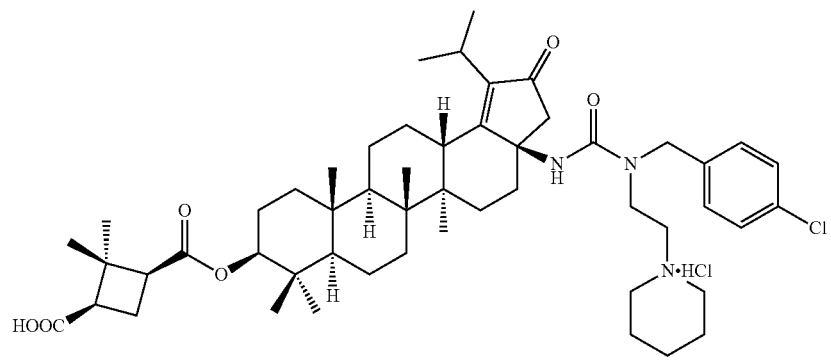

Step 1: Synthesis of 1-benzyl 3-((3aR,5aR,5bR, 7aR,9S,11aR,11bR,13aS)-3a-(3-(4-chloro benzyl)-3-(2-(piperidin-1-yl)ethyl)ureido)-1-isopropyl-5a,5b,8, 8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl) (1R,3S)-2,2-dimethylcyclobutane-1,3-dicarboxylate

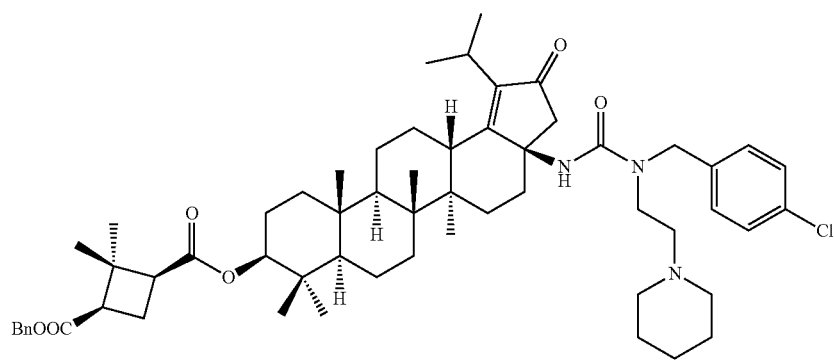

To a stirred solution of 1-benzyl 3-((3aR,5aR,5bR,7aR, 9S,11aR,11bR,13aS)-3a-isocyanato-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclo butane-1,3-dicarboxylate (Intermediate-2, 1.0 g, 1.4 mmol, 1.0 eq) in THF (10 ml) was added DIPEA (1.23 ml, 7.0 mmol, 5.0 eq) and N-(4-chlorobenzyl)-2-(piperidin-1-yl)ethan-1-amine (Intermediate-9, 0.531 g, 2.1 mmol, 1.5 eq). The reaction mixture was stirred at room temperature for about 14 hours. TLC indicated starting material was consumed and the desired product was observed. The reaction mixture was evaporated under reduced pressure, diluted with water (20 ml) and extracted with DCM (3×20 ml). The combined organic extracts were washed with brine solution (20 ml), dried over sodium sulfate, filtered and evaporated under reduced pressure. The residue was purified by silicagel column chromatography by using 5% methanol in DCM as an eluent to obtain the desired product (0.7 g, 53.8% yield) as a brown color semi solid. $^1$H NMR (300 MHz, CDCl$_3$): δ ppm 7.38-7.22 (m, 7H), 7.17 (d, J=8.4 Hz, 2H), 5.18-5.08 (m, 2H), 4.50-4.40 (m, 3H), 3.40-3.30 (m, 1H), 3.20-3.08 (m, 2H), 3.05-2.90 (m, 1H), 2.90-2.60 (m, 5H), 2.50-2.25 (m, 7H), 2.12-1.90 (m, 7H), 1.83-1.68 (m, 3H), 1.50-1.0 (m, 22H), 1.0-0.82 (m, 18H), 0.82-0.79 (m, 1H).

Step 2: Synthesis of (1R,3S)-3-((((3aR,5aR,5bR, 7aR,9S,11aR,11bR,13aS)-3a-(3-(4-chloro benzyl)-3- (2-(piperidin-1-yl)ethyl)ureido)-1-isopropyl-5a,5b,8, 8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl) oxy)carbonyl)-2,2-dimethylcyclobutane-1-carboxylic acid hydrochloride To a stirred solution of 1-benzyl 3-((3aR,5aR,5bR,7aR, 9S,11aR,11bR,13aS)-3a-(3-(4-chlorobenzyl)-3-(2-(piperidin-1-yl)ethyl)ureido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) (1R,3S)- 2,2-dimethylcyclobutane-1,3-dicarboxylate (step 1, 0.7 g, 0.7 mmol, 1.0 eq) in MeOH (6 ml), THF (4 ml) and water (2 ml) was added potassium hydroxide (0.274 g, 4.9 mmol, 7.0 eq). The reaction mixture was stirred at room temperature for about 14 hours. TLC indicated starting material was consumed and the desired product was observed. The reaction mixture was evaporated under reduced pressure, cooled to 0° C., acidified with 1N HCl to pH-4 and extracted with DCM (3×20 ml). The combined organic extracts were dried over sodium sulfate, filtered and evaporated under reduced pressure. The residue was purified by silicagel column chromatography by using 0-10% MeOH in DCM gradient. The fractions containing the expected product were combined and concentrated under reduced pressure to obtain the solid. To this solid compound, 1N HCl in 1,4-dioxane (5 ml) was added and stirred at room temperature for about 14 hours. The reaction mixture was evaporated under reduced pressure and dried under vacuum to obtain the desired product (0.2 g, 31% yield) as a white solid; $^1$H NMR (300 MHz, DMSO-$d_6$): δ ppm 12.1 (br.s., 1H), 9.70 (br.s., 1H), 7.44 (d, J=8.1 Hz, 2H), 7.22 (d, J=8.1 Hz, 2H), 6.37 (s, 1H), 4.66, 4.55 (ABq, 2H), 4.40-4.30 (m, 1H), 3.80-3.68 (m, 1H), 3.50-3.40 (m, 3H), 3.18-3.10 (m, 2H), 2.92-2.60 (m, 5H), 2.42-2.05 (m, 3H), 1.97-1.50 (m, 13H), 1.50-1.0 (m, 22H), 0.91 (s, 3H), 0.90-0.78 (m, 12H), 0.67 (s, 3H); ESI-MS: m/z 874.6 (M-HCl+H)$^+$.

Example 12: Preparation of (1R,3S)-3-((((3aR,5aR, 5bR,7aR,9S,11aR,11bR,13aS)-1-iso propyl-3a-(4- (2-(3-isopropyl-5-methyl-4H-1,2,4-triazol-4-yl) ethyl)piperazine-1-carboxamido)-5a,5b,8,8,11a- pentamethyl-2-oxo-3,3a,4,5,5a,5b,6,7,7a,8,9,10,11, 11a,11b,12,13,13a-octadecahydro-2H-cyclopenta[a] chrysen-9-yl)oxy)carbonyl)-2,2- dimethycyclobutane-1-carboxylic acid

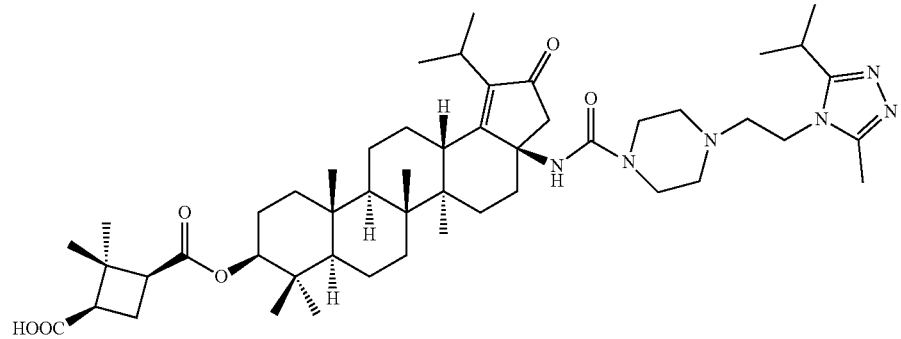

Step 1: Synthesis of 1-benzyl 3-((3aR,5aR,5bR,7aR,9S,11aR,11bR,13aS)-1-isopropyl-3a-(4-(2-(3-isopropyl-5-methyl-4H-1,2,4-triazol-4-yl)ethyl)piperazine-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

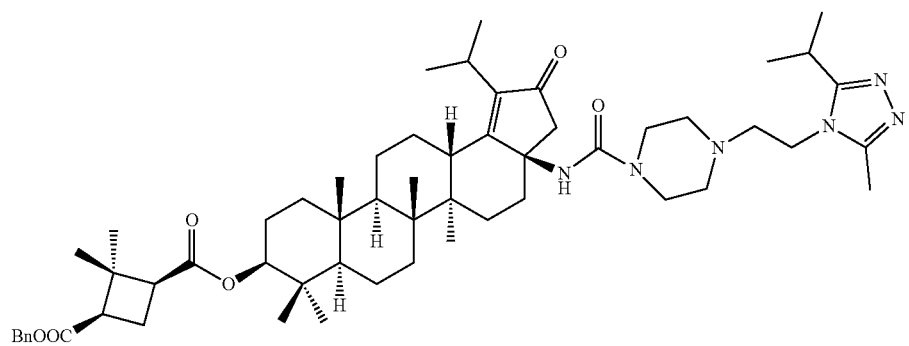

To a stirred solution of 1-benzyl 3-((3aR,5aR,5bR,7aR,9S,11aR,11bR,13aS)-3a-isocyanato-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclo butane-1,3-dicarboxylate (Intermediate-2, 1.0 g, 1.40 mmol, 1.0 eq) in THF (20 ml) was added DIPEA (1.23 ml, 5.625 mmol, 4.0 eq) and 1-(2-(3-isopropyl-5-methyl-4H-1,2,4-triazol-4-yl)ethyl)piperazine (Intermediate-10, 0.66 g, 2.81 mmol, 2.0 eq). The reaction mixture was stirred at room temperature for overnight. TLC indicated starting material was consumed and the desired product was observed. The reaction mixture was evaporated under reduced pressure, diluted with water (50 ml) and extracted with DCM (2×100 ml). The combined organic extracts were washed with brine solution (50 ml), dried over sodium sulfate, filtered and evaporated under reduced pressure. The residue was purified by silicagel column chromatography by using 5% methanol in DCM as an eluent to obtain the desired product (0.9 g, 69.2% yield) as a brown color solid. $^1$H NMR (300 MHz, CDCl$_3$): δ ppm 7.35 (m, 5H), 5.15, 5.09 (ABq, J$_{AB}$=12.3 Hz, 2H), 4.47-4.42 (m, 1H), 3.96-3.87 (m, 2H), 3.46-3.30 (m, 4H), 3.18-3.08 (m, 3H), 3.0-2.73 (m, 7H), 2.70-2.57 (m, 2H), 2.52-2.43 (m, 3H), 2.40-2.20 (m, 2H), 2.10-2.03 (m, 1H), 2.0-1.82 (m, 3H), 1.80-1.58 (m, 5H), 1.58-1.20 (m, 17H), 1.20-1.15 (m, 3H), 1.10 (s, 3H), 1.08-1.0 (m, 1H), 0.98-0.80 (m, 19H); ESI-MS: m/z 949.7 (M+H)$^+$.

Step 2: Synthesis of (1R,3S)-3-((((3aR,5aR,5bR, 7aR,9S,11aR,11bR,13aS)-1-isopropyl-3a-(4-(2-(3-isopropyl-5-methyl-4H-1,2,4-triazol-4-yl)ethyl)piperazine-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR,9S,11aR,11bR,13aS)-1-iso propyl-3a-(4-(2-(3-isopropyl-5-methyl-4H-1,2,4-triazol-4-yl)ethyl)piperazine-1-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 0.900 g, 0.948 mmol, 1.0 eq) in MeOH (18 ml) and THF (18 ml) was added aqueous 2.5N KOH solution (2.84 ml, 7.11 mmol, 7.5 eq). The reaction mixture was stirred at room temperature for overnight. TLC indicated starting material was consumed and the desired product was observed. The organic phase was evaporated under reduced pressure, the reaction mixture was diluted with water (50 ml), cooled to 0° C., acidified with 1N HCl to pH-6 and extracted with DCM (3×50 ml). The combined organic extracts were washed with water (50 ml), dried over sodium sulfate, filtered and evaporated under reduced pressure. The residue was purified by silicagel column chromatography by using 10% methanol in DCM as an eluent to obtain the desired product (30 mg, 3.6% yield) as a brown color solid. $^1$H NMR (300 MHz, DMSO-$d_6$): δ ppm 6.31 (s, 1H), 4.40-4.30 (m, 1H), 4.0-3.90 (m, 2H), 3.30-3.22 (m, 4H), 3.12-2.98 (m, 3H), 2.95-2.70 (m, 7H), 2.45-2.30 (m, 8H), 2.0-1.83 (m, 3H), 1.80-1.50 (m, 5H), 1.48-1.35 (m, 5H), 1.32-1.20 (m, 11H), 1.20-1.10 (m, 7H), 1.10-0.98 (m, 4H), 0.95-0.79 (m, 16H); ESI-MS: m/z 859.71 (M+H)$^+$.

Example 13: Preparation of (1R,3S)-3-((((3aR,5aR,5bR,7aR,9S,11aR,11bR,13aS)-1-iso propyl-5a,5b,8,8,11a-pentamethyl-2-oxo-3a-((S)-2-(pyrrolidin-1-ylmethyl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

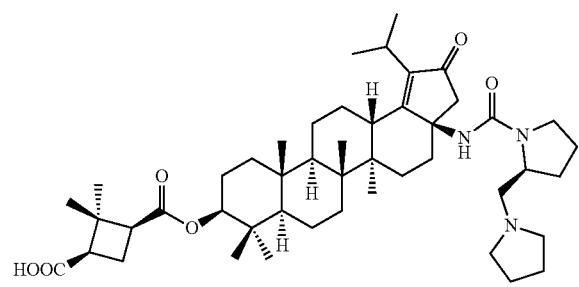

Step 1: Synthesis of 1-benzyl 3-((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

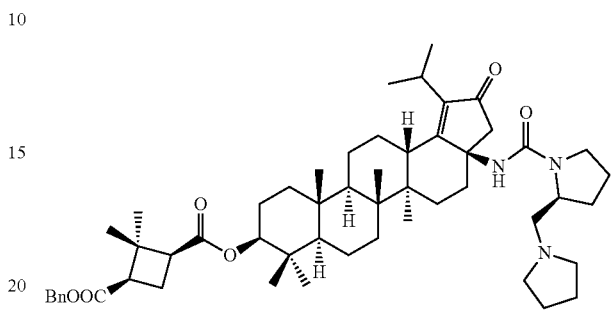

To a stirred solution of 1-benzyl 3-((3aR,5aR,5bR,7aR,9S,11aR,11bR,13aS)-3a-iso cyanato-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclo butane-1,3-dicarboxylate (Intermediate-2, 1.0 g, 1.405 mmol, 1.0 eq) in THF (20 ml) at 0° C. was added (S)-1-(pyrrolidin-2-ylmethyl)pyrrolidine 2,2,2-trifluoroacetate (Intermediate-11, 1.697 g, 6.325 mmol, 4.5 eq) and N,N-diisopropylethylamine (2.44 ml, 14.05 mmol, 10.0 eq). The reaction mixture was stirred at room temperature for overnight. TLC indicated starting material was consumed and the desired product was observed. The reaction mixture was diluted with water (200 ml) and extracted with ethyl acetate (3×200 ml). The combined organic extracts were dried over sodium sulfate, filtered and evaporated under reduced pressure. The residue was purified by silicagel column chromatography by using 0-4% methanol in dichloromethane gradient. The fractions containing the expected product were combined and concentrated under reduced pressure to obtain the desired product (1.058 g, 87% yield) as a white solid. $^1$H NMR (300 MHz, CDCl$_3$): δ ppm 7.35 (m, 5H), 5.15, 5.09 (ABq, 2H), 4.50-4.42 (m, 1H), 3.72-3.61 (m, 1H), 3.50-3.25 (m, 2H), 3.20-3.05 (m, 2H), 3.0-2.88 (m, 1H), 2.87-2.70 (m, 3H), 2.70-2.60 (m, 2H), 2.50-2.20 (m, 3H), 2.20-2.0 (m, 3H), 1.80-1.50 (m, 10H), 1.50-1.40 (m, 6H), 1.40-1.20 (m, 17H), 1.13 (s, 3H), 1.10-1.0 (m, 1H), 0.96 (s, 3H), 0.94 (s, 3H), 0.92 (s, 3H), 0.87 (s, 3H), 0.85 (s, 3H), 0.85 (m, 1H); ESI-MS: m/z 866.70 (M+H)$^+$.

Step 2: Synthesis of (1R,3S)-3-((((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR,9S,11aR,11bR,13aS)-1-iso propyl-5a,5b,8,8,11a-pentamethyl-2-oxo-3a-((S)-2-(pyrrolidin-1-ylmethyl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 0.350 g, 0.40 mmol, 1.0 eq) in MeOH (7 ml) and THF (7 ml)

was added aqueous 2.5N KOH solution (1.2 ml, 3.03 mmol, 7.5 eq). The reaction mixture was stirred at room temperature for about 16 hours. TLC indicated starting material was consumed and the desired product was observed. The organic phase was evaporated under reduced pressure, the reaction mixture was neutralized with 1N HCl and extracted with DCM (3×50 ml). The combined organic extracts were washed with water, dried over sodium sulfate, filtered and evaporated under reduced pressure. The residue was purified by silicagel column chromatography by using 0-10% methanol in DCM gradient. The fractions containing the expected product were combined and concentrated under reduced pressure to obtain the desired product (0.090 g, 28% yield) as a white solid. $^1$H NMR (300 MHz, CDCl$_3$): δ ppm 12.2 (br.s., 1H), 7.70 (s, 1H), 4.36 (m, 1H), 3.85-3.75 (m, 1H), 3.50-3.35 (m, 4H), 3.20-3.05 (m, 2H), 3.0-2.91 (m, 1H), 2.83-2.70 (m, 2H), 2.70-2.58 (m, 2H), 2.45-2.20 (m, 5H), 2.0-1.82 (m, 4H), 1.82-1.53 (m, 12H), 1.53-1.30 (m, 6H), 1.26 (s, 3H), 1.25-1.20 (m, 2H), 1.18-1.10 (m, 9H), 1.08-1.0 (m, 2H), 0.91 (s, 3H), 0.90 (s, 3H), 0.88 (s, 3H), 0.82 (s, 3H), 0.81 (s, 3H); ESI-MS: m/z 776.68 (M+H)$^+$; HPLC: 97.0%.

Pharmacological Activity

The compounds described herein can be tested for their antiviral activity following procedures known to a person of ordinary skill in the art. For example, the following protocols can be employed for testing the compounds. These protocols are illustrative and do not limit to the scope of the invention.

Example 14: Evaluation of Compounds Antiviral Activity

MT2 cells were infected with HIV-1 strain 92HT599 (10 TCID 50/30000 cells). The infected cells were plated at the concentration of ~30,000 cells per well in 96 well plate. Test compound was added to the micro plate in defined format with the final concentration of DMSO (vehicle) is not more than 1%. Incubation was carried out in CO$_2$ incubator for ~96 hours for viral infection. At the end of incubation period an aliquot from each well was taken for p24 estimation. The quantitation of p24 is an index for antiviral activity of the compound. Percent inhibition was calculated with reference to control values (vehicle controls).

P-24 estimation was carried out using Advance biosciences kit as per the procedure detailed by supplier.
Results:
For 0% serum binding assay, wherein "A" refers to an IC$_{50}$ value of less than 5 nM, "B" refers to IC$_{50}$ value in range of 5.01-10 nM, and "C" refers to IC$_{50}$ values greater than 10 nM;

For 40% serum binding assay, wherein "A" values refers to an IC$_{50}$ value of less than 30 nM, "B" refers to IC$_{50}$ value in range of 30.01-50 nM, and "C" refers to IC$_{50}$ values greater than 50 nM. The IC$_{50}$ (nM) values are set forth in Table-2.

TABLE 1A

| Example No. | 92HT599-Antiviral activity IC$_{50}$ (nM) | |
|---|---|---|
| | 0% | 40% |
| 1 | A | C |
| 2 | A | A |
| 3 | B | B |

TABLE 1A-continued

| Example No. | 92HT599-Antiviral activity IC$_{50}$ (nM) | |
|---|---|---|
| | 0% | 40% |
| 4 | A | C |
| 5 | A | A |
| 6 | A | B |
| 7 | B | B |
| 8 | B | C |
| 10 | A | A |
| 11 | A | B |
| 12 | C | C |
| 13 | A | C |

REFERENCES

1. Antiviral methods and protocols (Eds: D Kinchington and R. F. Schinazi) Humana Press Inc., 2000.
2. HIV protocols (Eds: N. L. Michael and J. H. Kim) Humana Press Inc, 1999.
3. DAIDS Virology manual from HIV laboratories, Publication NIH-97-3838, 1997.
4. HIV-1 p$^{24}$ antigen capture assay, enzyme immunoassay for detection of Human immunodeficiency Virus Type 1 (HIV-1) p24 in tissue culture media—Advanced bio science laboratories, Inc kit procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

We claim:
1. The compound of the formula (I):

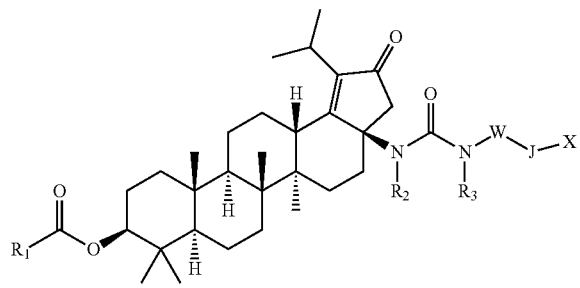

Formula (I)

wherein,

R₁ is

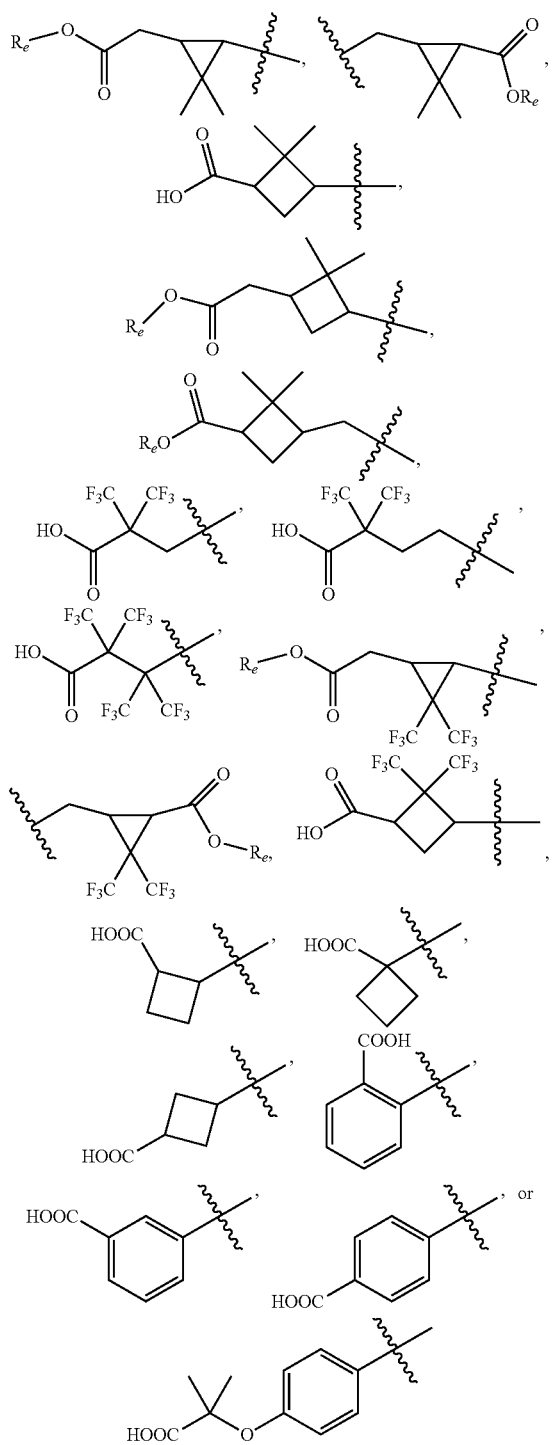

(wherein $R_e$ is hydrogen, substituted or unsubstituted alkyl, or substituted or unsubstituted cycloalkyl);

$R_2$ is hydrogen or substituted or unsubstituted alkyl;

$R_3$ is hydrogen, substituted or unsubstituted alkyl, substituted or unsubstituted amino alkyl, substituted or unsubstituted alkoxylalkoxy, substituted or unsubstituted alkoxylalkyl, substituted or unsubstituted arylalkyl, substituted or unsubstituted cycloalkylalkyl, substituted or unsubstituted heterocyclylalkyl or substituted or unsubstituted heteroarylalkyl; wherein the substituents are alkyl, halo or hydroxyl;

W is $(CR_aR_b)_n$;

$R_a$ and $R_b$ are independently hydrogen or substituted or unsubstituted alkyl, or $R_a$ and $R_b$ are taken together with the carbon to which they are attached to form 3-6 membered cycloalkyl;

W and $R_3$ are taken together with the nitrogen to which they are attached to form substituted or unsubstituted 4-10 membered heterocyclyl; wherein the substituents are alkyl, halo or hydroxyl;

J is absent, $(CR_cR_d)_{1-2}$ or $NR_g$;

$R_c$ and $R_d$ are independently hydrogen or $R_c$ and $R_d$ are taken together with the carbon to which they are attached to form 3-6 membered cycloalkyl;

$R_g$ is hydrogen or substituted or unsubstituted alkyl;

$R_3$ and $R_g$ are taken together with the nitrogen atoms to which they are attached to form substituted or unsubstituted 4-10 membered heterocyclyl; wherein the substituents are alkyl, halo or hydroxyl;

X is absent, substituted or unsubstituted alkyl, substituted or unsubstituted cycloalkyl, substituted or unsubstituted aryl, substituted or unsubstituted heterocyclyl or substituted or unsubstituted heteroaryl; wherein the substituent is one or more $R_f$;

$R_f$ is independently halogen, hydroxyl, alkyl, alkoxy, aryl, O-heterocyclyl, —O-aminoalkyl or aminoalkyl; and 'n' is 1 to 4;

or pharmaceutically acceptable salts, pharmaceutically acceptable solvates, pharmaceutically acceptable hydrates, tautomers, stereoisomers, ester prodrugs, or combination thereof.

2. The compound according to claim 1, is a compound of the formula (IA):

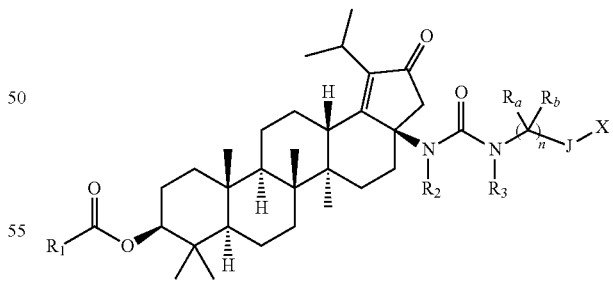

Formula (IA)

wherein, $R_1$, $R_2$, $R_3$, $R_a$, $R_b$, J, X and 'n' are same as defined in claim 1; or pharmaceutically acceptable salts, pharmaceutically acceptable solvates, pharmaceutically acceptable hydrates, tautomers, stereoisomers, prodrugs, or combination thereof.

3. The compound according to claim 1, is a compound of the formula (IB):

Formula (IB)

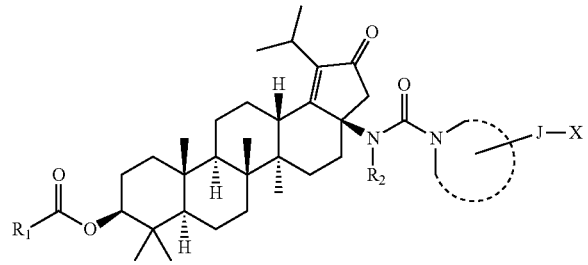

wherein,

R₁, R₂, J and X are same as defined in claim 1 and

is substituted or unsubstituted 4-7 membered heterocyclyl; or pharmaceutically acceptable salts, pharmaceutically acceptable solvates, pharmaceutically acceptable hydrates, tautomers, stereoisomers, prodrugs, or combination thereof.

4. The compound of formula

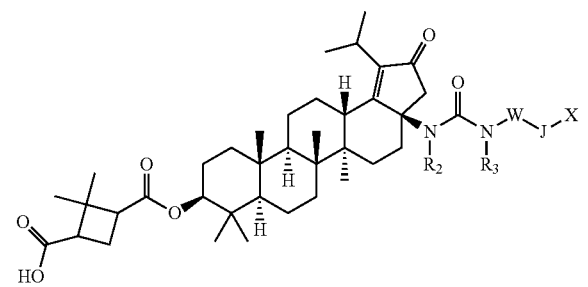

wherein,

R2 is hydrogen or substituted or unsubstituted alkyl;

R3 is hydrogen, substituted or unsubstituted alkyl, substituted or unsubstituted amino alkyl, substituted or unsubstituted alkoxylalkoxy, substituted or unsubstituted alkoxylalkyl, substituted or unsubstituted arylalkyl, substituted or unsubstituted cycloalkylalkyl, substituted or unsubstituted heterocyclylalkyl or substituted or unsubstituted heteroarylalkyl; wherein the substituents are alkyl, halo or hydroxyl;

W is $(CR_aR_b)_n$;

$R_a$ and $R_b$ are independently hydrogen or substituted or unsubstituted alkyl, or $R_a$ and $R_b$ are taken together with the carbon to which they are attached to form 3-6 membered cycloalkyl;

W and R₃ are taken together with the nitrogen to which they are attached to form substituted or unsubstituted 4-10 membered heterocyclyl; wherein the substituents are alkyl, halo or hydroxyl;

J is absent, $(CR_cR_d)_{1-2}$ or $NR_g$;

$R_c$ and $R_d$ are independently hydrogen or $R_c$ and $R_d$ are taken together with the carbon to which they are attached to form 3-6 membered cycloalkyl;

$R_g$ is hydrogen or substituted or unsubstituted alkyl;

R₃ and $R_g$ are taken together with the nitrogen atoms to which they are attached to form substituted or unsubstituted 4-10 membered heterocyclyl; wherein the substituents are alkyl, halo or hydroxyl;

X is absent, substituted or unsubstituted alkyl, substituted or unsubstituted cycloalkyl, substituted or unsubstituted aryl, substituted or unsubstituted heterocyclyl or substituted or unsubstituted heteroaryl; wherein the substituent is one or more $R_f$;

$R_f$ is independently halogen, hydroxyl, alkyl, alkoxy, aryl, —O-heterocyclyl, —O-aminoalkyl or aminoalkyl; and 'n' is 1 to 4;

or pharmaceutically acceptable salts, pharmaceutically acceptable solvates, pharmaceutically acceptable hydrates, tautomers, stereoisomers, ester prodrugs, or combination thereof.

5. The compound according to claim 1, wherein R₂ is hydrogen.

6. The compound according to claim 1, wherein "J" is absent or —$NR_g$.

7. The compound according to claim 1, wherein R₃ is hydrogen, substituted or unsubstituted alkyl, substituted or unsubstituted amino alkyl, or substituted or unsubstituted heterocyclylalkyl; wherein the substituents are alkyl, halo or hydroxyl.

8. A compound selected from the group consisting of:
(1R,3S)-3-((((3aR,5aR,5bR,7aR,9S,11aR,11bR,13aS)-3a-(3-(4-chlorobenzyl)-3-(2-(dimethylamino)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride, (1R,3S)-3-((((3aR,5aR,5bR,7aR,9S,11aR,11bR,13aS)-3a-((S)-2-(1-(2-(dimethyl amino)ethyl)-5-phenyl-1H-imidazol-2-yl)pyrrolidine-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(1-(4-chlorophenyl) cyclopropyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(2-(4-chlorophenyl) propan-2-yl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-((1-(4-chlorophenyl) cyclopropyl)methyl)-3-(2-(dimethylamino)ethyl)ureido)-1-isopropyl-5a,5b,8,8,11a-penta methyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(4-chlorobenzyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-3a-((1R,3S,5S)-3-(3-isopropyl-5-methyl-4H-1,2,4-triazol-4-yl)-8-azabicyclo[3.2.1]octane-8-carboxamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(4-chlorobenzyl)-3-(2-(pyrrolidin-1-yl)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-(3-(2-(5-phenyl-1H-imidazol-2-yl)propan-2-yl)ureido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(3-(4-chlorobenzyl)-3-(2-(piperidin-1-yl)ethyl)ureido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride, (1R,3S)-3-((((3aR,5aR,5bR,7aR,9S,11aR,11bR,13aS)-1-isopropyl-3a-(4-(2-(3-iso propyl-5-methyl-4H-1,2,4-triazol-4-yl)ethyl)piperazine-1-carboxamido)-5a,5b,8,8,11a-penta methyl-2-oxo-3,3a,4,5,5a,5b,6,7,7a, 8,9,10,11,11a,11b,12,13,13a-octadecahydro-2H-cyclo penta[a]chrysen-9-yl)oxy)carbonyl)-2,2-dimethylcyclobutane-1-carboxylic acid, and (1R,3S)-3-((((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carboxamido)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, or pharmaceutically acceptable salts, pharmaceutically acceptable solvates, pharmaceutically acceptable hydrates, tautomers, stereoisomers, ester prodrugs, or combination thereof.

9. A pharmaceutical composition comprising a compound according to claim 1 and at least one pharmaceutically acceptable excipient.

10. The pharmaceutical composition according to claim 9, wherein the pharmaceutically acceptable excipient is a carrier or diluent.

11. A pharmaceutical composition comprising a compound according to claim 8 and at least one pharmaceutically acceptable excipient.

\* \* \* \* \*